US008987377B2

(12) United States Patent
Barrett et al.

(10) Patent No.: US 8,987,377 B2
(45) Date of Patent: Mar. 24, 2015

(54) POLY(AMIDE) POLYMERS FOR THE DELIVERY OF OLIGONUCLEOTIDES

(75) Inventors: Stephanie E. Barrett, Perkasie, PA (US); Marina Busuek, Center Valley, PA (US); Steven L. Colletti, Princeton Junction, NJ (US); Robert M. Garbaccio, Lansdale, PA (US); Erin N. Guidry, Cranford, NJ (US); Robert A. Kowtoniuk, Glenside, PA (US); Jing Liao, Livingston, NJ (US); Craig A. Parish, Tenafly, NJ (US); Rubina G. Parmar, Harleysville, PA (US); Tao Pei, Holmdel, NJ (US); Kevin M. Schlosser, North Wales, PA (US); David M. Tellers, Lansdale, PA (US); Sandra C. Tobias, Lansdale, PA (US); Quang T. Truong, Morganville, NJ (US); Jacob H. Waldman, Metuchen, NJ (US); Weimin Wang, Churchville, PA (US); J. Michael Williams, Hillsborough, NJ (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/885,737

(22) PCT Filed: Nov. 16, 2011

(86) PCT No.: PCT/US2011/060893
§ 371 (c)(1),
(2), (4) Date: Jun. 13, 2013

(87) PCT Pub. No.: WO2012/068187
PCT Pub. Date: May 24, 2012

(65) Prior Publication Data
US 2013/0253135 A1 Sep. 26, 2013

Related U.S. Application Data

(60) Provisional application No. 61/415,546, filed on Nov. 19, 2010.

(51) Int. Cl.
A61K 47/48 (2006.01)
C08G 73/02 (2006.01)
C08L 79/02 (2006.01)

(52) U.S. Cl.
CPC ........ *A61K 47/48092* (2013.01); *C08G 73/028* (2013.01); *C08L 79/02* (2013.01)
USPC .......... 525/54.1; 525/54.2; 525/420; 525/435; 530/300; 530/324; 530/325; 530/326; 530/327; 530/328; 530/329; 530/330; 530/350; 536/22.1; 536/23.1

(58) Field of Classification Search
CPC ....... A61K 38/02; A61K 38/03; C08G 69/08; C08G 69/10; C07K 4/00; C07K 5/04; C07K 7/04; C07K 2319/80
USPC ........ 525/54.1, 54.2, 420, 435; 530/300, 324, 530/325, 326, 327, 328, 329, 330, 350; 536/22.1, 23.1
See application file for complete search history.

(56) References Cited

U.S. PATENT DOCUMENTS

| 5,574,142 A * | 11/1996 | Meyer et al. ................. 536/23.1 |
| 2004/0132958 A1* | 7/2004 | Deming et al. ............... 528/328 |
| 2009/0232762 A1 | 9/2009 | Xiong et al. |
| 2011/0060123 A1 | 3/2011 | Kataoka et al. |

FOREIGN PATENT DOCUMENTS

WO 2009133968 A1 11/2009

OTHER PUBLICATIONS

Yang, J., et al.; Journal of the American Chemical Society, 1998, p. 10646-10652.*
Costantino, P., et al.; Biopolymers, 1979, p. 9-24.*
Zhu, T., et al.; Antisense Research and Development, 1993, p. 265-275.*

* cited by examiner

*Primary Examiner* — Robert Jones, Jr.
(74) *Attorney, Agent, or Firm* — Jeffrey N. Townes; LeClairRyan

(57) ABSTRACT

The present invention provides poly(amide) polymers, polyconjugates, compositions and methods for the delivery of oligonucleotides for therapeutic purposes.

18 Claims, 17 Drawing Sheets

| ID | siRNA Conjugation Efficiency | Masking Efficiency |
|---|---|---|
| Polyconjugate 1 | 86 | 42 |

| ID | siRNA Conjugation Efficiency | Masking Efficiency |
|---|---|---|
| Polyconjugate 2 | 89 | 59 |

FIG. 1C

Polyconjugate 1:

| ID | bDNA IC50 (nM) *in vitro* | MTS IC50 (nM) *in vitro* |
|---|---|---|
| Polyconjugate 1 | >300 | >300 |

FIG.4A

Polyconjugate 2:

| ID | bDNA IC50 (nM) *in vitro* | MTS IC50 (nM) *in vitro* |
|---|---|---|
| Polyconjugate 2 | 60 | >300 |

FIG.4B

POLY(AMIDE) POLYMERS FOR THE DELIVERY OF OLIGONUCLEOTIDES

REFERENCE TO SEQUENCE LISTING SUBMITTED ELECTRONICALLY

The sequence listing of the present application is being submitted electronically via EFS-Web as an ASCII formatted sequence listing with a file name "MRLMIS00042USPCT-SEQTXT-15MAY2013.txt", creation date of May 15, 2013 and a size of 4.78 KB. This sequence listing submitted via EFS-Web is part of the specification and is herein incorporated by reference in its entirety.

BACKGROUND OF THE INVENTION

Oligonucleotides conjugated to polymers are known. Further, the delivery of oligonucleotides conjugated to polymers (polyconjugates) for therapeutic purposes is also known. See WO2000/34343; WO2008/022309; and Rozema et al. PNAS (2008) 104, 32: 12982-12987.

Poly(amide) polymers are known. Duksin et al. (1970) P.N.A.S. 67, 185-192; Bichowsky-Slomnicki et al. (1956) Archives of Biochemistry and Biophysics 65, 400-413; Duksin et al. (1975) FEBS Letters 60, 21-25; Yang et al. (1998) J. Am. Chem. Soc. 120, 10646-10652; Miyata et al. (2008) J. Am. Chem. Soc. 130, 16287-16294; Sato et al. (2010) Biol. Pharm. Bull. 33(7), 1246-1249); WO2008/070141 and U.S. 2009/0232762.

Herein, we disclose and describe novel endosomolytic poly(amide) polymers and polyconjugates useful for the delivery of oligonucleotides for therapeutic purposes. The poly(amide) polymers of the instant invention are novel and contain both cationic and aliphatic functional moieties.

SUMMARY OF THE INVENTION

The present invention provides poly(amide) polymers, polyconjugates, compositions and methods for the delivery of oligonucleotides for therapeutic purposes.

BRIEF DESCRIPTION OF THE FIGURES

FIG. 4. Mouse In Vitro Data of Masked Polyconjugates from Polymers 1 and 2.

DETAILED DESCRIPTION OF THE INVENTION

Figure 1A:
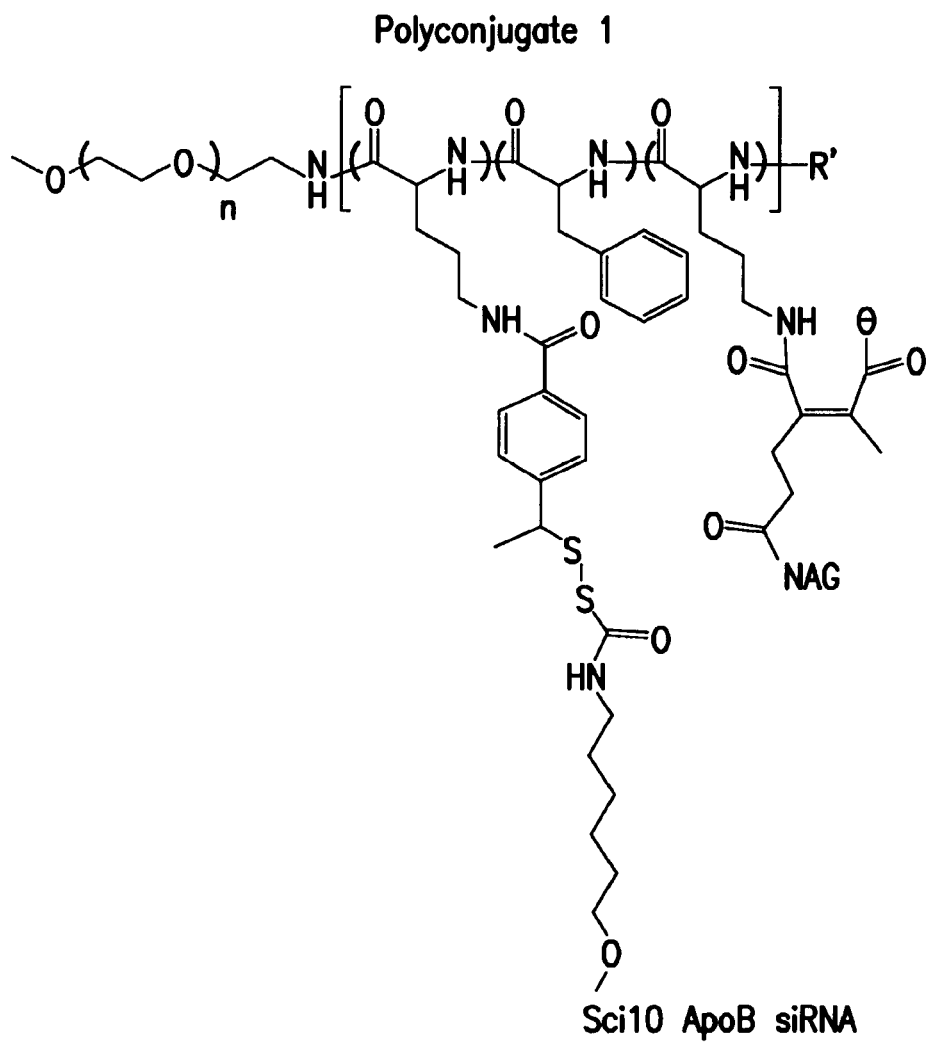
FIG. 1. Analytical Results from Polyconjugates 1 and 2.

In a first embodiment of the instant invention is a polymer comprising Formula Z:

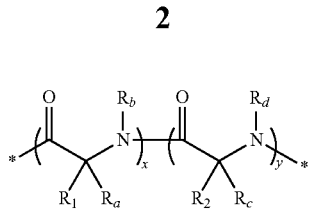

wherein:
x is 2 to 1000;
y is 2 to 1000;
$R_1$ is a cationic component;
$R_2$ is an aliphatic component or hydrogen;
$R_a$ is independently selected from $R_1$ and $R_2$
$R_b$ is independently selected from $R_1$ and $R_2$
$R_c$ is independently selected from $R_1$ and $R_2$; and
$R_d$ is independently selected from $R_1$ and $R_2$; or stereoisomer thereof.

In a second embodiment of the instant invention is a polymer comprising Formula Z':

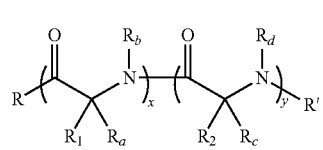

wherein:
x is 2 to 1000;
y is 2 to 1000;
R is an initiator;
R' is an end group;
$R_1$ is a cationic component;
$R_2$ is an aliphatic component or hydrogen;
$R_a$ is independently selected from $R_1$ and $R_2$
$R_b$ is independently selected from $R_1$ and $R_2$
$R_c$ is independently selected from $R_1$ and $R_2$; and
$R_d$ is independently selected from $R_1$ and $R_2$; or stereoisomer thereof.

In a third embodiment of the instant invention is a polymer comprising Formula Z":

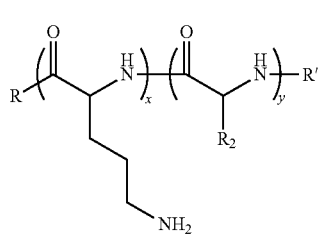

wherein:
x is 2 to 250;
y is 2 to 250;
R is an initiator;
R' is an end group; and
$R_2$ is an aliphatic component or hydrogen; or stereoisomer thereof.

In another embodiment of the instant invention is a polymer conjugate composition comprising a polymer of Formula Z, Z' or Z", a linker and an oligonucleotide.

In another embodiment of the instant invention is the polymer conjugate composition above further comprising a masking agent.

In another embodiment of the instant invention is the polymer conjugate composition above further comprising a masking agent, wherein the masking agent is selected from PEG 0.5 kDa and/or PEG 2 kDa and/or CDM-PEG 0.5 kDa and/or CDM-PEG 2 kDa.

In another embodiment of the instant invention is the polymer conjugate composition above further comprising a targeting ligand.

In another embodiment of the instant invention is the polymer conjugate composition above further comprising a targeting ligand, wherein the targeting ligand is selected from GalNAc and/or tri-GalNAc and/or CDM-GalNAc and/or CDM-tri-GalNAc.

In another embodiment of the instant invention is the polymer conjugate composition above further comprising a masking agent and a targeting ligand.

In another embodiment of the instant invention is the polymer conjugate composition above further comprising a masking agent, wherein the masking agent is selected from PEG 0.5 kDa and/or PEG 2 kDa and/or CDM-PEG 0.5 kDa and/or CDM-PEG 2 kDa; and a targeting ligand, wherein the targeting ligand is selected from GalNAc and/or tri-GalNAc and/or CDM-GalNAc and/or CDM-tri-GalNAc.

In another embodiment of the instant invention is the polymer conjugate composition above further comprising a masking agent and a targeting ligand, wherein the targeting ligand to masking agent ratio is about 1:1.

In another embodiment of the instant invention is the polymer conjugate composition above further comprising a masking agent and a targeting ligand, wherein the targeting ligand to masking agent ratio is about 1:3.

In another embodiment of the instant invention is a polymer conjugate composition made by the 1) synthesis of an activated polymer comprising Formula Z, Z' or Z"; 2) synthesis of an activated oligonucleotide; and 3) conjugation of the activated polymer with the activated oligonucleotide; optionally including the addition of a masking agent and/or a targeting ligand.

In an embodiment of the instant invention is a polymer conjugate composition comprising a polymer of Formula Z", and a masking agent and a targeting ligand, wherein the targeting ligand to masking agent ratio is about 1:3.

In an embodiment of the instant invention is a polymer conjugate composition comprising a polymer of Formula Z", and CDM-PEG 0.5 kDa and CDM-GalNAc wherein the targeting ligand to masking agent ratio is about 1:3.

In another embodiment of the instant invention is a method of treating a disease in a patient by administering a polymer conjugate composition of the instant invention.

Definitions

"Aliphatic component" means a compound composed of carbon and hydrogen. Aliphatic compounds can be cyclic, like cyclohexane, or acyclic, like hexane. Aliphatic compounds can be saturated, like hexane, or unsaturated, like hexene. Aliphatic compounds can be straight chains, branched chains, or non-aromatic rings (in which case they are called alicyclic), Aliphatic compounds can be joined by single bonds (alkanes), double bonds (alkenes), or triple bonds (alkynes). An aliphatic component includes aromatic components and steroids. "Amine (primary, secondary, tertiary or quaternary)" means organic compounds and functional groups that contain a basic nitrogen atom with a lone pair. Amines are derivatives of ammonia, wherein one or more hydrogen atoms have been replaced by a substituent such as an alkyl or aryl group. The amines of the instant invention are optionally substituted with OH, or halogen.

"Aromatic component" means a compound composed of hydrocarbon with a conjugated cyclic molecular structure. The aromatic components of the instant invention are optionally substituted with OH, ethers, or amines.

"Cationic component" means a chemical moiety that can carry a positive charge. A cationic component includes amines, and nitrogen heterocycles. The cationic components of the instant invention are optionally substituted with OH, or halogen.

"Disease" means a disorder or incorrectly functioning organ, part, structure, or system of the body resulting from the effect of genetic or developmental errors, infection, poisons, nutritional deficiency or imbalance, toxicity, or unfavorable environmental factors; illness; sickness; ailment. An example of a disease is cancer.

"End group" means the last unit in a polymer chain, at the opposite end from the initiator. In an embodiment, an end group is a hydrogen, carboxylate or other end group as discussed and disclosed in Deming, T., J. Polym. Sci. Part A: Polym. Chem. (2000) 38:3011-3018.

"Halogen" means fluorine (F), bromine (Br), Iodine (I) and Chlorine (Cl).

"Initiator" means a reactive moiety which facilitates polymer synthesis including an amine, alcohol, water, alkali halide, alkoxide, hydroxide, or a transition metal initiator. See Hadjichristidis, N. Chem. Rev. (2009) 109:5528-5578 for a more detailed review of initators. Further, initiators include amines selected from a diamine, a bisamine, a monoprotected diamine, and a dendrimer having multiple amines as end groups. One utility of a protecting group, such as a monoprotected diamine, is to allow directed end placement of, for example, an oligonucleotide, a linker, a masking agent or a targeting ligand or combinations thereof, as illustrated below:

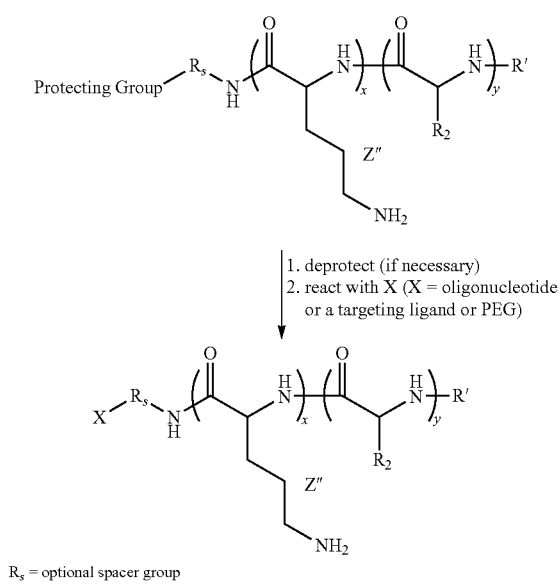

$R_s$ = optional spacer group

"Linker" means a chemical moiety that physically conjugates the oligonucleotide with the polymer of Formula Z, Z' or Z".

"Masking agent" means a molecule which, when linked to a polymer, shields, inhibits or inactivates one or more properties (biophysical or biochemical characteristics) of the polymer. See WO2008/022309 for a more detailed description of masking agents. A masking agent can be labile or non-labile. A labile masking agent can be an acid sensitive CDM-PEG, wherein the PEG molecular weight can range between 200 and 5000. A non-labile masking agent can be PEG, wherein the PEG molecular weight can range between 200 and 5000.

"Nitrogen heterocycle" means an organic compound containing at least one atom of carbon and at least one atom of nitrogen within a ring structure. These structures may comprise either simple aromatic rings or non-aromatic rings. The nitrogen heterocycles of the instant invention are optionally substituted with OH, or halogen.

"Oligonucleotide" means deoxyribonucleic acid (DNA) and ribonucleic acid (RNA) and combinations of DNA, RNA and other natural and synthetic nucleotides, including protein nucleic acid (PNA). DNA maybe in form of cDNA, in vitro polymerized DNA, plasmid DNA, parts of a plasmid DNA, genetic material derived from a virus, linear DNA, vectors (P1, PAC, BAC, YAC, and artificial chromosomes), expression vectors, expression cassettes, chimeric sequences, recombinant DNA, chromosomal DNA, anti-sense DNA, or derivatives of these groups. RNA may be in the form of messengerRNA (mRNA), in vitro polymerized RNA, recombinant RNA, transfer RNA (tRNA), small nuclear RNA (snRNA), ribosomal RNA (rRNA), chimeric sequences, anti-sense RNA, interfering RNA, small interfering RNA (siRNA), microRNA (miRNA), ribozymes, external guide sequences, small non-messenger RNAs (snmRNA), untranslatedRNA (utRNA), snoRNAs (24-mers, modified snmRNA that act by an anti-sense mechanism), tiny non-coding RNAs (tncRNAs), small hairpin RNA (shRNA), or derivatives of these groups. In addition, DNA and RNA may be single, double, triple, or quadruple stranded. Double, triple, and quadruple stranded polynucleotide may contain both RNA and DNA or other combinations of natural and/or synthetic nucleic acids. Oligonucleotides can be chemically modified. The use of chemically modified oligonucleotides can improve various properties of the oligonucleotides including, but not limited to: resistance to nuclease degradation in vivo, cellular uptake, activity, and sequence-specific hybridization. Non-limiting examples of such chemical modifications include: phosphorothioate internucleotide linkages, LNA, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. These chemical modifications, when used in various oligonucleotide constructs, are shown to preserve oligonucleotide activity in cells while at the same time, dramatically increasing the serum stability of these compounds. Chemically modified siRNA can also minimize the possibility of activating interferon activity in humans. See WO2008/022309 for a more detailed description of oligonucleotides.

"Patient" means a mammal, typically a human, in need of treatment for a disease.

"Polymer" means a molecule built up by repetitive smaller units called monomers. A polymer can be linear, branched, network, star, comb, or ladder type. A polymer of the instant invention is a copolymer in which two or more different monomers are used. Copolymers may by alternating, random (statistical), gradient, block and graft (comb). The monomers in statistical copolymers have no definite order or arrangement along any given chain. The general compositions of such polymers are reflective of the ratio of input monomers. However, the exact ratio of one monomer to another may differ between chains. The distribution of monomers may also differ along the length of a single polymer. Also, the chemical properties of a monomer may affect its rate of incorporation into a statistical copolymer and its distribution within the polymer. Thus, while the ratio of monomers in a statistical polymer is dependent on the input ratio of monomer, the input ratio may not match exactly the ratio of incorporated monomers. See WO2008/022309 for a more detailed description of polymers.

An example of a statistical polymer of the instant invention is:

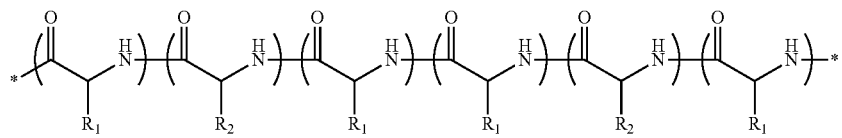

An example of a block polymer of the instant invention is:

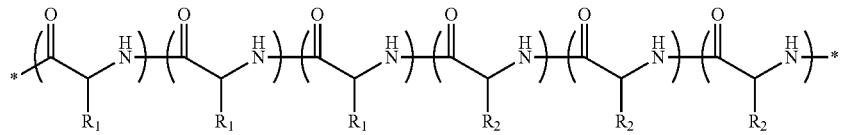

"Steroid" includes, for example, cholesterol. The steroids of the instant invention are optionally substituted with OH, halogen, acids, ethers, or amines.

"Targeting ligand", also refered to as "targeting agent", means an agent that can deliver a polymer or polyconjugate to target cells or tissues, or specific cells types. Targeting ligands enhance the association of molecules with a target cell. Thus, targeting ligands can enhance the pharmacokinetic or biodistribution properties of a polyconjugate to which they are attached to improve cellular distribution and cellular uptake of the conjugate. Targeting ligands can either be labile or non-labile. Labile targeting ligands can include an acid sensitive CDM-GalNAc. A non-labile targeting ligand can include mono GalNAc or preferably tri-GalNAc. See WO2008/022309 for a more detailed description of targeting ligands.

In an embodiment of Formula Z, Z' or Z", x and y are independently 2 to 750.

In another embodiment of Formula Z, Z' or Z", x and y are independently 2 to 500.

In another embodiment of Formula Z, Z' or Z", x and y are independently 2 to 250.

In another embodiment of Formula Z, Z' or Z", x and y are independently 2 to 150.

In another embodiment of Formula Z, Z' or Z", x and y are independently 25 to 150.

In another embodiment of Formula Z, Z' or Z", x and y are independently 50 to 125.

In another embodiment of Formula Z, Z' or Z", x and y are independently 75 to 100.

In another embodiment of Formula Z, Z' or Z", x is about 25 and y is about 25.

In another embodiment of Formula Z, Z' or Z", x is about 50 and y is about 50.

In another embodiment of Formula Z, Z' or Z", x is about 75 and y is about 75.

In another embodiment of Formula Z, Z' or Z", x is about 100 and y is about 100.

In another embodiment of Formula Z, Z' or Z", x is about 95 and y is about 5.

In another embodiment of Formula Z, Z' or Z", x is about 90 and y is about 10.

In another embodiment of Formula Z, Z' or Z", x is about 85 and y is about 15.

In another embodiment of Formula Z, Z' or x is about 80 and y is about 20.

In another embodiment of Formula Z, Z' or Z", x is about 75 and y is about 25.

In another embodiment of Formula Z, Z' or Z", x is about 70 and y is about 30.

In another embodiment of Formula Z, Z' or Z", x is about 65 and y is about 35.

In another embodiment of Formula Z, Z' or Z", x is about 60 and y is about 40.

In another embodiment of Formula Z, Z' or Z", x is about 55 and y is about 45.

In another embodiment of Formula Z, Z' or Z", x is about 50 and y is about 50.

In another embodiment of Formula Z, Z' or Z", x and y are in a ratio of about 16:1 or about 8:1 or about 4:1 or about 3:1 or about 2:1 or about 1:1.

In an embodiment, R is an initiator selected from an amine, alcohol, water, alkali halide, alkoxide, hydroxide, or a transition metal initiator.

In an embodiment, R is an initiator selected from an amine, sodium methoxide, sodium hydroxide, lithium chloride, transition metal complexes from nickel, cobalt, or iron. For example, zero valent nickel complex bipyNi(COD) (bipy 2,2'-bipyridyl, COD=1,5-cyclooctadiene).

In an embodiment, R is an amine.

In an embodiment, R is an amine selected from a diamine, a bisamine, a monoprotected diamine, and a dendrimer having multiple amines as end groups.

In another embodiment, R is an amine selected from, n-butylamine, n-heptadecane, mPEG 2K amine, mPEG 5K amine, mPEG 12K amine, O,O'-bis(2-aminoethyl)polyethylene glycol, ethylene diamine, 1,6-hexanediamine, 2-(2-aminoethoxy)ethyl 2-(acetylamino)-2-deoxy-β-D-galactopyranoside, N-Boc-ethylenediamine, L-aspartic acid β-benzyl ester, cholesterol-C8-amine, INF7-amine terminated, DSPE amine, and poly(amido amine) (PAMAM) dendimers with surface amino groups.

In another embodiment, R is an amine selected from, n-butylamine and mPEG 2K amine.

In another embodiment, R is n-butylamine.

In another embodiment, R' is H or carboxylate.

In another embodiment, R' is H.

In an embodiment, $R_1$ is independently selected from an amine and a nitrogen heterocycle.

In another embodiment, $R_1$ is independently selected from methyl amine, ethyl amine, propyl amine, butylamine, pentyl amine, hexyl amine, heptyl amine, octyl amine, nonyl amine, decyl amine, undecyl amine, dodecyl amine, tridecyl amine, tetradecyl amine, pentadecyl amine, hexadecyl amine, heptadecyl amine, octadecyl amine, 2-(2-aminoethoxy)ethyl, 2-(1H-imidazol-4-yl)ethyl, 2-[2-(2-aminoethoxy)ethoxy]ethyl, 3-amino-2-hydroxypropyl, 2-aminoethyl, 4-aminobutyl, 6-aminohexyl, 8-aminooctyl, 10-aminodecyl and 1-methyl-2-imidazole modified ornithine.

In another embodiment, $R_1$ is independently selected from methyl amine, ethyl amine, propyl amine, butylamine, pentyl amine, hexyl amine, heptyl amine, octyl amine, nonyl amine, decyl amine, undecyl amine, dodecyl amine, tridecyl amine, tetradecyl amine, pentadecyl amine, hexadecyl amine, heptadecyl amine and octadecyl amine.

In another embodiment, $R_1$ is independently selected from, 2-(2-aminoethoxy)ethyl, 2-(1H-imidazol-4-yl)ethyl, 2-[2-(2-aminoethoxy)ethoxy]ethyl, 3-amino-2-hydroxypropyl, 2-aminoethyl, 4-aminobutyl, 6-aminohexyl, 8-aminooctyl and 10-aminodecyl.

In another embodiment, $R_1$ is independently selected from 2-(2-aminoethoxy)ethyl and 2-(1H-imidazol-4-yl)ethyl.

In another embodiment, $R_1$ is 3-aminopropyl.

In an embodiment, $R_2$ is independently selected from steroids, an alkyl group, an alkenyl group and an alkynyl group, all of which may be branched or cyclic or acyclic or aromatic.

In another embodiment, $R_2$ is independently selected from H, methyl, ethyl, propyl, butyl, hexyl, heptyl, octyl, nonyl, decyl, undecyl, dodecyl, tridecyl, tetradecyl, pentadecyl, hexadecyl, heptadecyl, octadecyl, cholesterol, lipid chains, benzyl, benzyl propanoate, benzyl acetate, isopropyl, 2-methylpropane, 2-methylbutane, isobutyl, 2-n-butyl, benzyl, 4-methyl phenol, ethylbenzene, 1-fluoro-4-methylbenzene, 4-methylbiphenyl, 2-methylnaphthalene, 1-methylnaphthalene, 5-ethyl-1-H-imidazole, 4-methyl imidazole and 2-methyl indole.

In another embodiment, $R_2$ is independently selected from H, methyl, ethyl, propyl, butyl, hexyl, heptyl, octyl, nonyl, decyl, undecyl, dodecyl, tridecyl, tetradecyl, pentadecyl, hexadecyl, heptadecyl, octadecyl, cholesterol, lipid chains and benzyl.

In another embodiment, $R_2$ is independently selected from butyl, dodecyl, octyl and octadecyl.

In another embodiment, $R_2$ is independently selected from H, methyl, isopropyl, isobutyl, 2-n-butyl, benzyl, 4-methyl phenol, 4-methyl imidazole and 2-methyl indole.

In an embodiment, $R_a$, $R_b$, $R_c$ and $R_d$ are independently selected from hydrogen, steroids, an alkyl group, an alkenyl group and an alkynyl group, all of which may be branched or cyclic or acyclic or aromatic, methyl amine, ethyl amine, propyl amine, butylamine, pentyl amine, hexyl amine, heptyl amine, octyl amine, nonyl amine, decyl amine, undecyl amine, dodecyl amine, tridecyl amine, tetradecyl amine, pentadecyl amine, hexadecyl amine, heptadecyl amine, octadecyl amine, 2-(2-aminoethoxy)ethyl, 2-(1H-imidazol-4-yl)ethyl, 2-[2-(2-aminoethoxy)ethoxy]ethyl and 3-amino-2-hydroxypropyl.

In another embodiment, $R_a$, $R_b$, $R_c$ and $R_d$ are independently selected from hydrogen, an alkyl group, an alkenyl group and an alkynyl group, all of which may be branched or cyclic or acyclic or aromatic, methyl amine, ethyl amine, propyl amine, butylamine, pentyl amine, hexyl amine, heptyl amine, octyl amine, nonyl amine, decyl amine, 2-(2-aminoethoxy)ethyl, 2-(1H-imidazol-4-yl)ethyl, 2-[2-(2-aminoethoxy]ethoxy]ethyl and 3-amino-2-hydroxypropyl.

In another embodiment, $R_a$, $R_b$, $R_c$ and $R_d$ are independently selected from hydrogen, an alkyl group, methyl amine, ethyl amine, propyl amine, butylamine, pentyl amine and hexyl amine.

In another embodiment, $R_a$, $R_b$, $R_c$ and $R_d$ are independently selected from hydrogen, an alkyl group, methyl amine, ethyl amine, propyl amine and butylamine.

In another embodiment, $R_a$, $R_b$, $R_c$ and $R_d$ are hydrogen.

In an embodiment, a linker is the chemical moiety which is made by the conjugation of a derivative of (4-succinimidyloxycarbonyl-{-methyl-{-[2-pyridyldithio]toluene; SMPT) and a derivative of N-Succinimidyl-S-acetylthioacetate (SATA).

In an embodiment, a linker is the chemical moiety which is made by the conjugation of a derivative of (N-Succinimidyl 3-(2-pyridyldithio)-propionate; SPDP) and a derivative of N-Succinimidyl-S-acetylthioacetate (SATA).

In an embodiment, a linker is the chemical moiety which is made by the conjugation of a derivative of carboxydimethylmaleic anhydride-linked siRNA.

In an embodiment, a masking agent is selected from a maleic anhydride derivative.

In an embodiment, a masking agent is selected from a disubstituted maleic anhydride derivative.

In an embodiment, a masking agent is selected from CDM-PEG 0.5 kDa.

In an embodiment, a masking agent is selected from CDM-PEG 2 kDa.

In an embodiment, a targeting ligand is selected from compounds with affinity to cell surface molecules, cell receptor ligands, and antibodies, antibody fragments, and antibody mimics with affinity to cell surface molecules.

In another embodiment, a targeting ligand is selected from carbohydrates, glycans, saccharides (including, but not limited to: galactose, galactose derivatives, mannose, and mannose derivatives), vitamins, folate, biotin, aptamers, and peptides (including, but not limited to: RGD-containing peptides, insulin, EGF, and transferrin).

In another embodiment, a targeting ligand is selected from N-acetylgalactosamine (GalNAc), mannose and glucose.

In another embodiment, a targeting ligand is selected from N-acetylgalactosamine (GalNAc). GalNAc may also be referred to as NAG.

In another embodiment, a targeting ligand is selected from CDM-N-acetylgalactosamine (GalNAc).

In another embodiment, a targeting ligand is selected from tri-N-acetylgalactosamine (GalNAc).

In another embodiment, a targeting ligand is selected from CDM-tri-N-acetylgalactosamine (GalNAc).

In an embodiment, an oligonucleotide is selected from siRNA, miRNA and antisense. In another embodiment, an oligonucleotide is an siRNA.

In an embodiment, the polymers comprising Formulas Z, Z' or Z" are copolymers.

In an embodiment, the polymers comprising Formulas Z, Z' or Z" are copolymers which are statistical.

In an embodiment, the polymers comprising Formulas Z, Z' or Z" are copolymers which are gradient.

In an embodiment, the polymers comprising Formulas Z, Z' or Z" are copolymers which are block.

Formulation

The polyconjugate (composition of the polymer comprising Formula Z, Z' or Z" and an oligonucleotide) is formed by covalently linking the oligonucleotide to the polymer. Conjugation of the oligonucleotide to the polymer can be performed in the presence of excess polymer. Because the oligonucleotide and the polymer may be of opposite charge during conjugation, the presence of excess polymer can reduce or eliminate aggregation of the polyconjugate. Excess polymer can be removed from the polyconjugate prior to administration of the polyconjugate to a patient. Alternatively, excess polymer can be co-administered with the polyconjugate to the patient.

Similarly, the polymer can be conjugated to a masking agent in the presence of an excess of polymer or masking agent. Because the oligonucleotide and the polymer may be of opposite charge during conjugation, the presence of excess polymer can reduce or eliminate aggregation of the polyconjugate. Excess polymer can be removed from the polyconjugate prior to administration of the polyconjugate to a patient. Alternatively, excess polymer can be co-administered with the polyconjugate to the patient. The polymer can be modified prior to or subsequent to conjugation of the oligonucleotide to the polymer.

Parenteral routes of administration include intravascular (intravenous, interarterial), intramuscular, intraparenchymal, intradermal, subdermal, subcutaneous, intratumor, intraperitoneal, intrathecal, subdural, epidural, and intralymphatic injections that use a syringe and a needle or catheter. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, bile ducts, and ducts of the salivary or other exocrine glands. The intravascular route includes delivery through the blood vessels such as an artery or a vein. The blood circulatory system provides systemic spread of the pharmaceutical. An administration route involving the mucosal membranes is meant to include nasal, bronchial, inhalation into the lungs, or via the eyes. Intraparenchymal includes direct injection into a tissue such as liver, lung, heart, muscle (skeletal muscle or diaphragm), spleen, pancreas, brain (including intraventricular), spinal cord, ganglion, lymph nodes, adipose tissues, thyroid tissue, adrenal glands, kidneys, prostate, and tumors. Transdermal routes of administration have been affected by patches and iontophoresis. Other epithelial routes include oral, nasal, respiratory, rectum, and vaginal routes of administration.

The polyconjugates can be injected in a pharmaceutically acceptable carrier solution. Pharmaceutically acceptable refers to those properties and/or substances which are acceptable to the patient from a pharmacological/toxicological point of view. The phrase pharmaceutically acceptable refers to molecular entities, compositions, and properties that are physiologically tolerable and do not typically produce an allergic or other untoward or toxic reaction when administered to a patient. Preferably, as used herein, the term pharmaceutically acceptable means approved by a regulatory agency of the Federal or a state government or listed in the U.S. Pharmacopeia or other generally recognized pharmacopeia for use in animals, and more particularly in humans.

Utility

The polyconjugates (compositions of a polymer comprising Formula Z, Z' or Z" and an oligonucleotide) of the instant invention may be used for research purposes or to produce a change in a cell that can be therapeutic. The use of polyconjugates for therapeutic purposes is known. See WO2000/34343; WO2008/022309; and Rozema et al. PNAS (2008) 104, 32: 12982-12987.

EXAMPLES

Examples and schemes provided are intended to assist in a further understanding of the invention. Particular materials employed, species and conditions are intended to be further illustrative of the invention and not limitative of the reasonable scope thereof.

Monomer Synthesis

Boc-L-ornithine N-carboxyanhydride (NCA) (Scheme 1):

To a slurry of boc-L-ornithine (35 g, 151 mmol) in 1.2 L of tetrahydrofuran (THF) under nitrogen was charged a solution of triphosgene (16.9 g, 55.8 mmol) in 240 mL of THF. The reaction was heated at 50-55° C. for 1 h then cooled to ambient temperature. The remaining solid was removed by filtration washing with 100 mL of THF. The filtrate was concentrated by vacuum distillation to 350 mL and the solvent was switched to cyclopentylmethyl ether (CPME). The resulting slurry was cooled to ambient temperature and stirred under nitrogen overnight. The solid was isolated by filtration washing with 70 mL of CPME and vacuum dried to give 35.0 g (90% yield) of white crystalline product. $^1$H NMR (500 MHz, DMSO-$d_6$): δ 9.08 (s, 1 H); 6.86 (s, 1 H); 4.44 (t, J=6.15 Hz, 1 H); 2.92 (q, J=6.41 Hz, 2 H); 1.75-1.67 (m, 1 H); 1.65-1.57 (m, 1 H); 1.51-1.30 (m, 2 H); 1.38 (s, 9H).

L-Phenylalanine N-carboxyanhydride (NCA) (Scheme 2):

A 1 L round bottom was dried in an oven prior to use (oven temp=120 ° C.). The glassware was cooled under an inert nitrogen atmosphere. Phenylalanine (50.0 g, 303 mmol) was added to the flask. Anhydrous THF (600 mL, 0.5 M) was charged to give a suspension of white solid. The mixture was heated to 50° C. and triphosgene (35.9 g, 121 mmol) was added as a solid. The suspension was stirred until the reaction was clear (~30 min). The reaction mixture was concentrated to an oil and then was slowly poured into 3 L of hexanes with rapid stirring to yield a white precipitate. The resulting suspension was capped using aluminum foil and placed in the freezer for a minimum of 3 h. The white precipitate was then filtered via vacuum filtration while maintaining an inert environment. The white solid was rinsed with hexanes (3×20 mL) to give the product. The white solid was collected and dried overnight under vacuum. $^1$H NMR (500 MHz, CHCl$_3$-d): δ 7.37-7.30 (3 H, m); 7.18 (2 H, d, J=7.21 Hz); 6.23 (1 H, s); 4.53 (1 H, dd, J=8.18, 4.21 Hz); 3.27 (1 H, dd, J=14.14, 4.20 Hz); 3.00 (1 H, dd, J=14.13, 8.17 Hz).

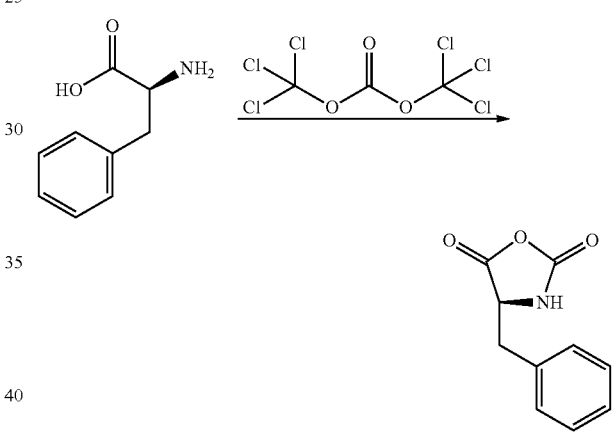

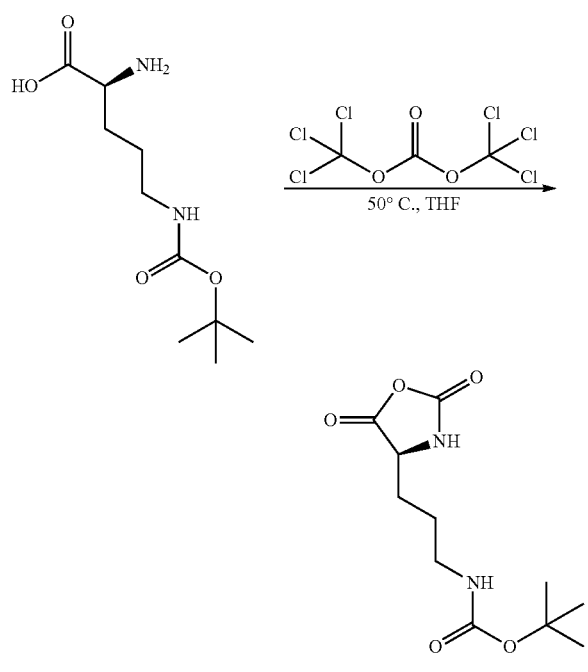

Polymer Synthesis (Scheme 3)

Statistical Copolymer—Polymer 1

L-Boc-ornithine-N-carboxyanhydride (2.5 g) and the phenylalanine-N-carboxyanhydride (1.9 g) was placed in a round-bottom flask and was purged with an atmosphere of nitrogen. Following this, 40 mL of anhydrous DMA was added. The solution was stirred until it became clear. Then mPEG-2K amine was added to the roundbottom as a solution (0.39g in 1 mL of DMA). The entire flask was put under vacuum (<10$^{-6}$ mmHg). The solution bubbled, assuming the release of CO$_2$. The solution continued to stir at room temperature overnight. The next day, the solution was clear. The mixture was precipitated in water (1L) and then filtered. The collected precipitate was frozen and placed on the lyophilizer for 48 hours to dry the product. Deprotection of the amines was carried out (see below for procedure). GPC analysis of the deprotected polymer followed, giving a polymer with a $M_n$=10,500 g/mol and a PDI of 1.1.

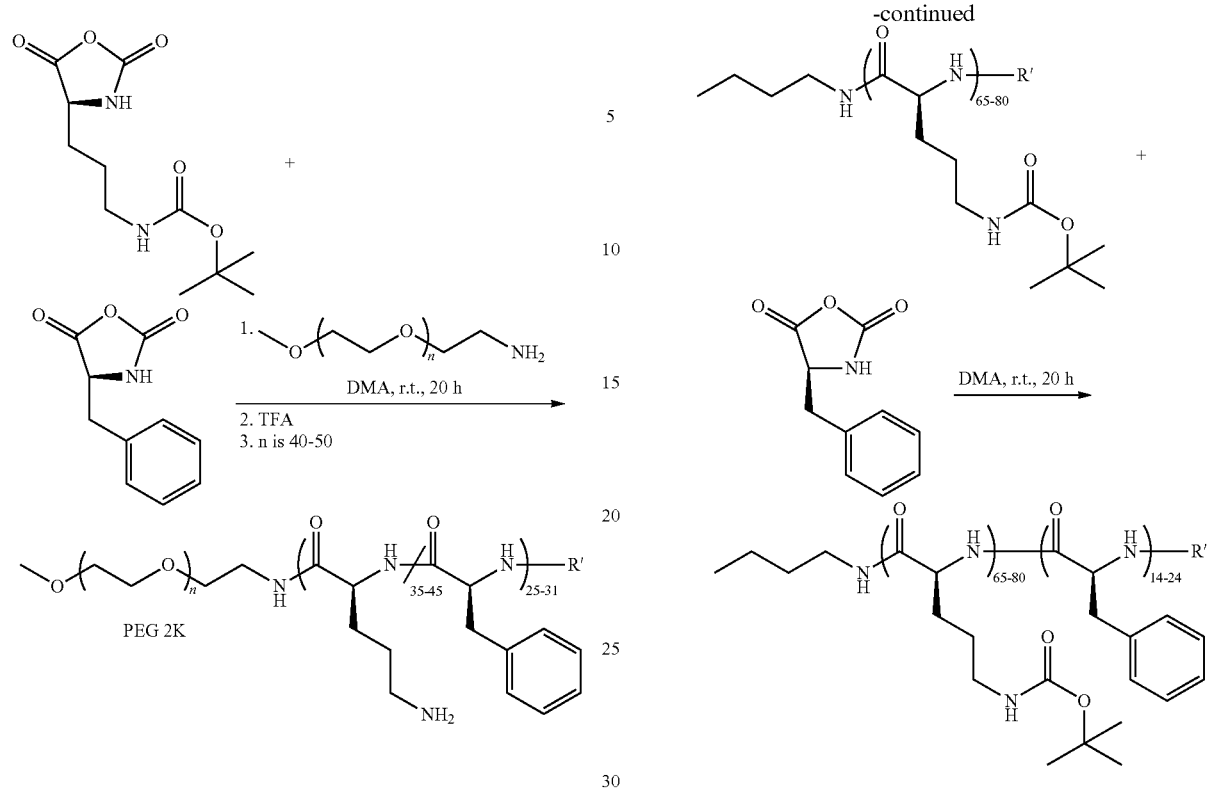

wherein R' is an end group selected from: a hydrogen or carboxylate.

Block Copolymer—Polymer 2

L-Boc-ornithine-N-carboxyanhydride (12 g) was placed in a round-bottom flask and was purged with an atmosphere of nitrogen. Following this, 40 mL of anhydrous DMA was added. The solution was stirred until it became clear. Then n-butylamine (0.138 mL) was added to the roundbottom. The entire flask was put under vacuum (<$10^{-6}$ mmHg). The solution bubbled, assuming the release of $CO_2$. The solution continued to stir at room temperature overnight (and a sample was collected for gel permeation chromatography, $M_n$-16,400 g/mol, PDI=1.1). The next day, the phenylalanine-N-carboxyanhydride (2 g) was added to the flask and allowed to react for an additional 8 hours. The solvent was removed using a Genevac®, and the resulting oil was precipitated in water and then filtered. The collected precipitate was dried under vacuum overnight. GPC analysis followed, giving a polymer with a $M_n$=18,000 g/mol and a PDI of 1.12.

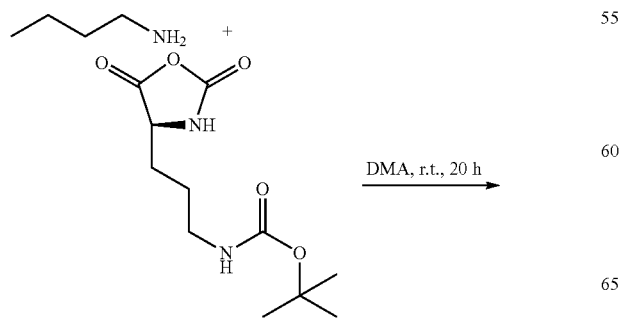

wherein R' is an end group selected from: a hydrogen or carboxylate.

Deprotection:

The protected polymer was added to a roundbottom and dissolved in dichloromethane (35 mg/mL polymer). The solid dissolved readily to give a hazy solution. The solution was stirred at room temperature under nitrogen. Next, trifluoroacetic acid was added to the solution (1:1 dichloromethane (DCM):trifluoroacetic acid (TFA) by volume). The solution became clear immediately and was allowed to react for 20 minutes. The deprotected polymer was obtained after the solvent and volatile byproducts were removed by vacuum.

Shown Below for Polymer 2:

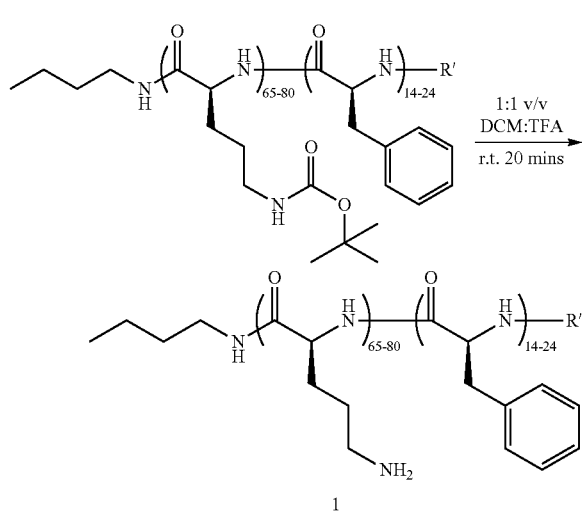

H spectra were recorded on Varian spectrometer operating at 500 MHz with a relaxation delay of 0.5 s. $^1$H NMR spectra were in full accordance with the expected structures. All NMR spectra were taken in deuterated DMSO.

Figure 7:
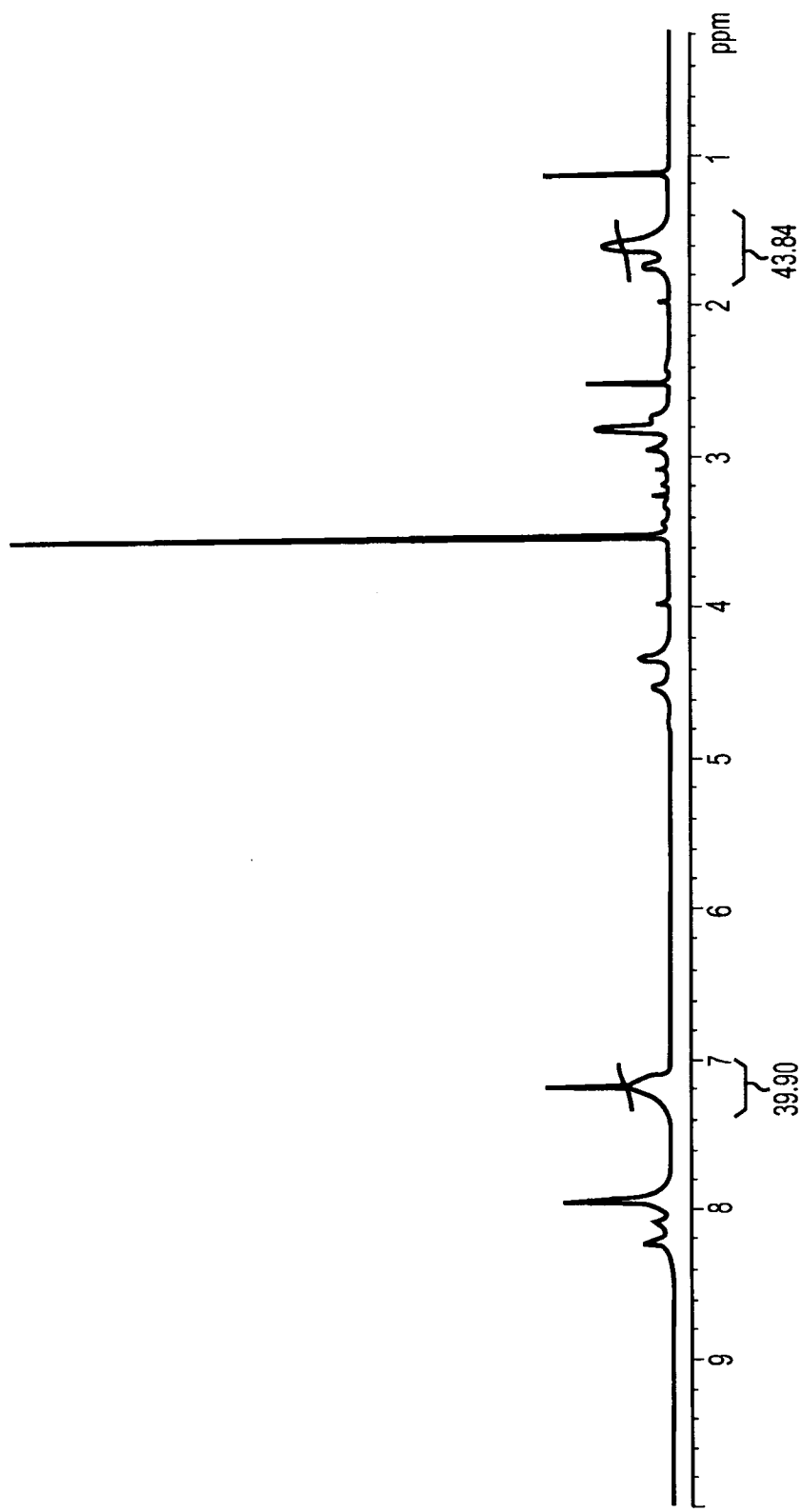
FIG. 7. $^1$H NMR spectra for Polymer 1.

$^1$H of Polymer 1:

See FIG. 7 for $^1$H NMR spectra of Polymer 1.

The ornithine:phenylalanine ratio was determined by looking at the signals between 1.4 -1.8 ppm (equivalent to 4 protons, a) for ornithine and the signals from 7-7.4 ppm for the phenylalanine (equivalent to 5 protons, b). For polymer 1, the average ratio was determined to be 38 ornithine to 28 phenylalanine units per polymer chain.

Calculations:

Number of hydrogens associated with ornithine = intergration from 1.4-1.8 ppm/number of protons associated with the signal = 43.6/4 = 10.9

Number of hydrogens associated with phenylalanine = intergration from 7-7.4 ppm/number of protons associated with that signal = 39.9/5 = 8.0

Ratio of ornithine:phenylalanine = number of hydrogens associated with ornithine/ number of hydrogens associated with phenylalanine = 10.9/8.0 = 1.4

Therefore, there are 1.4× more ornithine units in the polymer backbone than phenylalanine units.

The molecular weight obtained by organic GPC of the deprotected polymer was 10,500 g/mol, which is 8,500 g/mol consisting of ornithine and phenylalanine and 2,000 g/mol for the PEG 2 K initiator.

The number of phenylalanine units =8,500 g/mol/(molecular weight of the ornithine repeat unit×NMR ratio of ornithine to phenylalanine+the molecular weight of the phenylalanine repeat unit) =8,500 g/mol/(114 g/mol×1.4+147 g/mol) =28 Phenylalanine units Since there are 1.4× more orthine units in the polymer backbone than phenylalanine units, there are 38 units of ornithine (28×1.4).

$^1$H of Polymer 2:

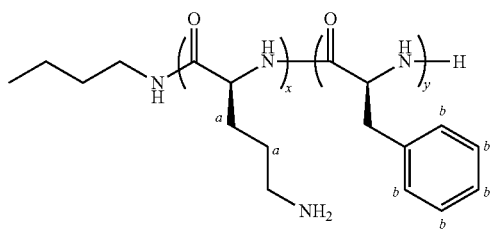

Figure 8:
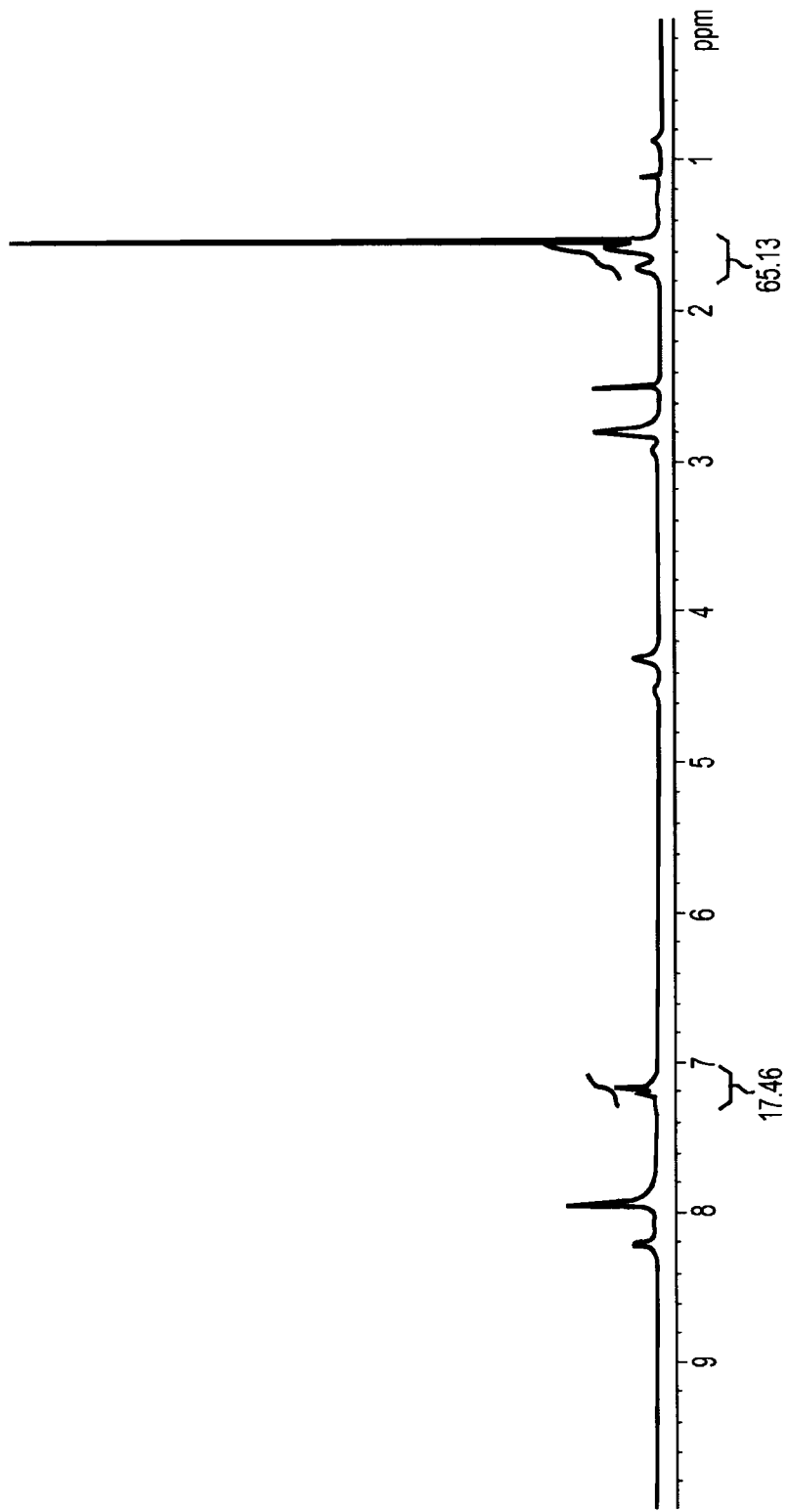
FIG. 8. $^1$H NMR spectra for Polymer 2.

See FIG. 8 for $^1$H NMR spectra of Polymer 2.

The ornithine:phenylalanine ratio was determined by looking at the signals between 1.4 -1.8 ppm (equivalent to 4 protons, a) for ornithine and the signals from 7-7.4 ppm for the phenylalanine (equivalent to 5 protons, b). For polymer 2, the average ratio was determined to be 73 ornithine to 16 phenylalanine units per polymer chain.

Calculations:

Number of hydrogens associated with ornithine = intergration from 1.4-1.8 ppm/number of protons associated with the signal = 65.13/4 = 16.3

Number of hydrogens associated with phenylalanine = intergration from 7-7.4 ppm/number of protons associated with that signal = 17.46/5 = 3.5

Ratio of ornithine:phenylalanine = number of hydrogens associated with ornithine/ number of hydrogens associated with phenylalanine = 16.3/3.5 = 4.7

Therefore, there are 4.6× more orthine units in the polymer backbone than phenylalanine units.

The molecular weight obtained by organic GPC of the protected polymer was 18,000 g/mol.

The number of phenylalanine units =

18,000 g/mol/(molecular weight of the *boc*-protected ornithine repeat unit× NMR ratio of ornithine to phenylalanine+ the molecular weight of the phenylalanine repeat unit) =

18,000 g/mol/(214 g/mol×4.7 + 147 g/mol) = 16 Phenylalanine units

Since there are 4.7× more ornithine units in the polymer backbone than phenylalanine units, there are 73 units of ornithine (16×4.7).

Molecular weight and molecular weight distributions were estimated using a gel-permeation chromatography (GPC) (Waters Alliance 2695 Separations Module) system equipped with a TOSOH TSKgel Alpha 3000 column and a Waters 2414 refractive index detector. The columns were eluted with dimethylformamide (DMF) containing lithium chloride (10 mM) (0.5 mL/min) at 40° C. The molecular weights and molecular weight distributions of poly(amide) polymers were compared to poly(styrene) standards (Sigma-Aldrich).

Figure 9:
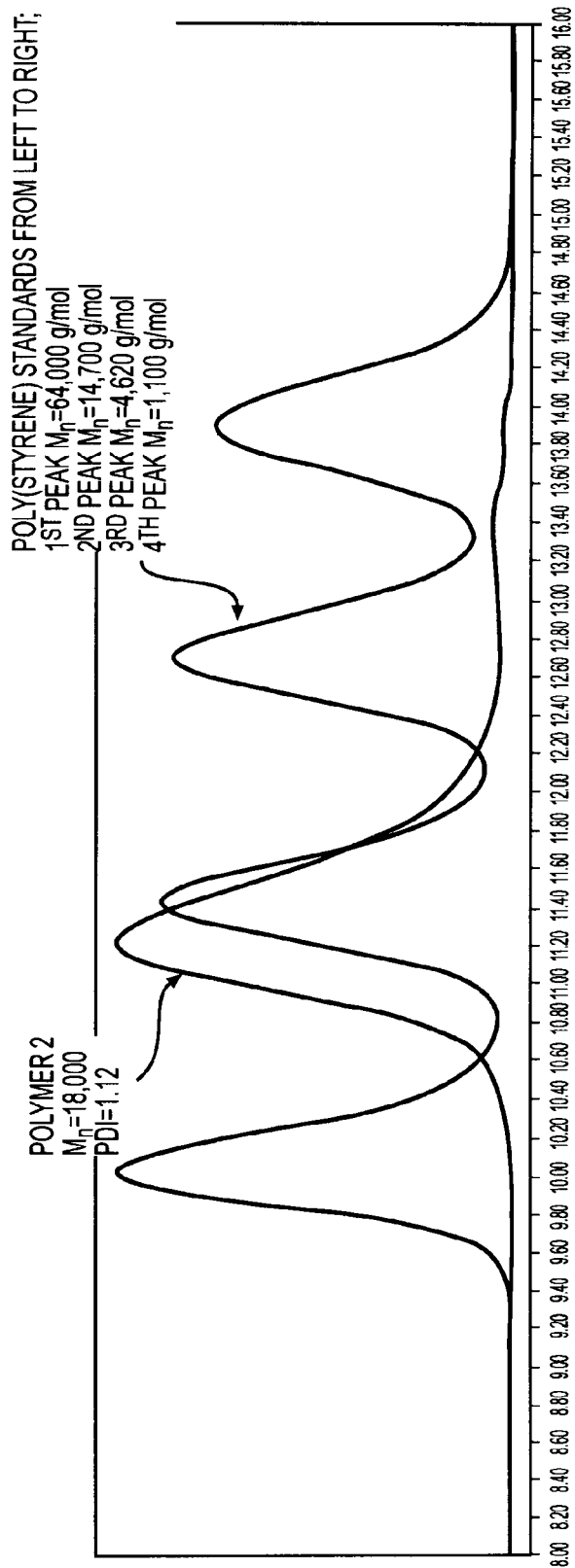
FIG. 9. A typical GPC trace of poly(amide) polymers as compared to poly(styrene) standards.

A typical GPC trace is shown in FIG. 9.

Polymers

Exemplary polymers of the instant invention made by the Schemes above include:

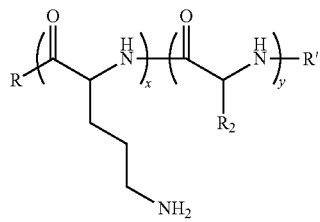

wherein x and y are independently 2 to 100, R is n-butylamine or mPEG-amine (where the PEG molecular weight can range from 500 g/mol to 12,000 g/mol), R' is an end group selected from: a hydrogen or carboxylate;

and $R_2$ is one of the following:

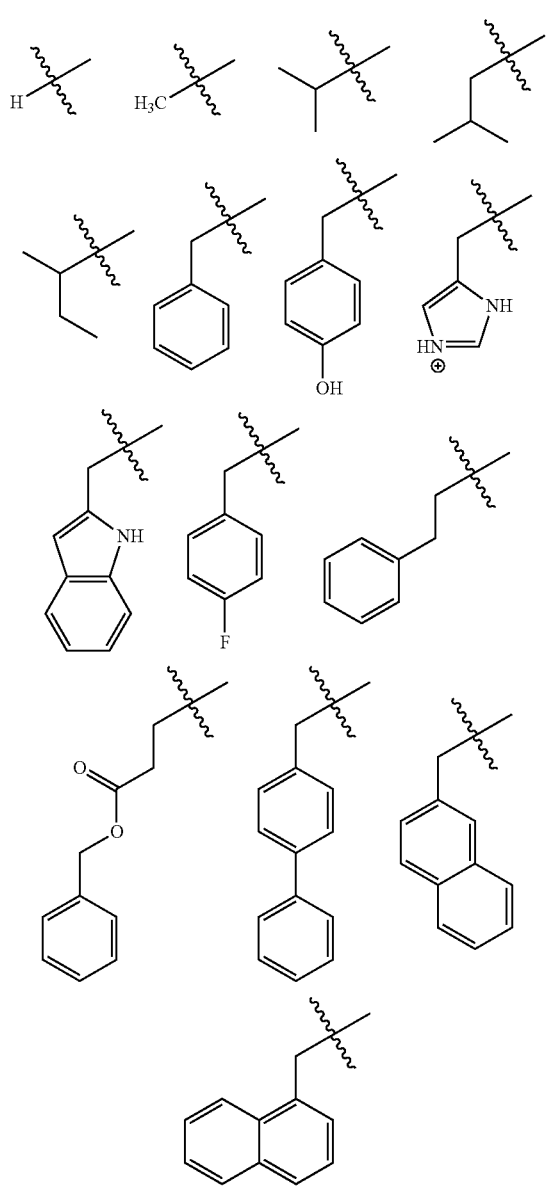

Polymer 1

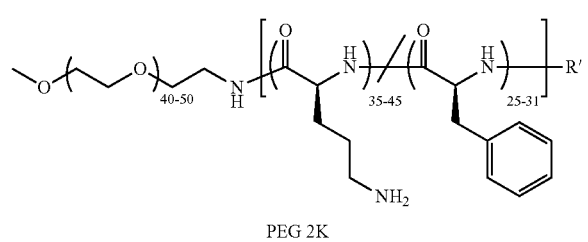
PEG 2K

R' is an end group selected from: a hydrogen or carboxylate;

and more specifically:

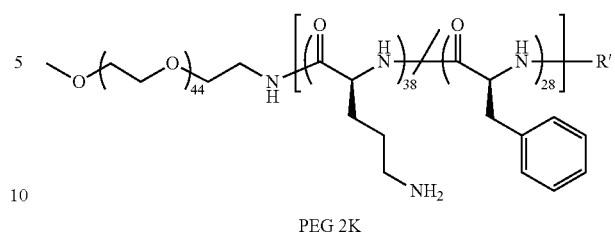
PEG 2K

R' is an end group selected from: a hydrogen or carboxylate.

Polymer 2

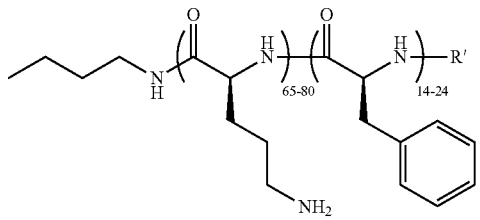

R' is an end group selected from: a hydrogen or carboxylate; and more specifically:

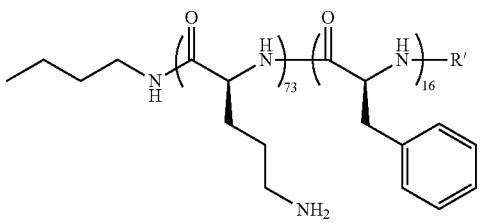

R' is an end group selected from: a hydrogen or carboxylate.

Within the schemes and examples provided, polymers with randomly oriented repeating units are denoted by round brackets with a forward slash between repeating units. For example, a statistical copolymer of monomer A and monomer B will be represented by the formula

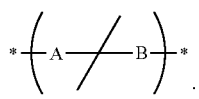

In contrast, a block copolymer having m repeating units of monomer A and n repeating units of monomer B will be represented by the following formula

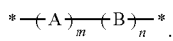

Conjugation (Scheme 4)

The polymers comprising Formula Z, Z' or Z" and the specific examples shown above were synthesized for use in the following conjugation steps to ultimately create the polyconjugates of the instant invention. The polymers comprising Formula Z, Z' or Z" and the specific examples disclosed are useful in the preparation of polyconjugates which are, in turn, useful for the delivery of oligonucleotides, specifically the delivery of siRNA. Other methods for the synthesis of polyconjugates are described in WO2008/022309.

Polymer 1 (Scheme 4A)

Step 1: Activation of Polymer

Approximately 19.05 mg of polymer is added into a 4 mL vial along with ~603 µL of DMSO. The solution is heated to 50° C. and mixed until the polymer is completely dissolved (approximately 20 minutes). Next, 27.15 µL of a solution of SMPT in DMSO (1 mg/100 µL) is added (corresponding to 1.5 wt % with respect to the polymer weight).

Step 2: Activation of Oligonucleotide

Oligonucleotide (1 g, 0.0714 mmol) is dissolved in 0.1M sodium bicarbonate buffer (20 ml, 50 mg/mL) in a vial with magnetic stir bar and cooled to 0-5° C. in an ice water bath. In a separate vial, SATA (83 mg, 0.357 mmol, 5 equivalents) is dissolved in 0.78 ml DMSO. The SATA solution is added over 1 min and the clear, colorless reaction mixture stirred at 0-5° C. for 2 h. After 2 h, the reaction mixture is sampled and analyzed by UPLC or HPLC for completion of the conjugation. If >5% oligonucleotide remains unreacted, another charge of SATA in DMSO (2.0 equivalents) is added and the reaction aged at 0-5° C. for completion of the SATA conjugation (confirmation by HPLC or UPLC; column=Dionex DNApac). When there is <5% unreacted oligonucleotide remaining by UPLC or HPLC, the reaction mixture is purified by TFF dialysis using water (~2 L) or PD10 column to remove any remaining SATA/succinimides. The recovered purified solution is lyophilized to a white fluffy solid. The recovery is typically around 95% and the purity is greater than 70% by UPLC.

Step 3: Polymer-oligonucleotide Conjugation

The activated polymer is diluted with 100 mM TRIS, 5% glucose, buffer at pH=9 resulting in a final polymer concentration of ~2.7 mg/mL. About 1.35 mg of oligonucleotide is added to the activated polymer solution and allowed to react at room temperature for one hour until the final masking step.

Step 4: Masking of Polymer Conjugate

In a separate vial, 20.8 mg of carboxydimethylmaleic anhydride-N-acetylgalactosamine (CDM-GalNAc) is weighed out. The siRNA-polymer conjugate solution is then transferred into this vial containing CDM-GalNAc and stirred for 10 minutes at room temperature. The polyconjugate solution is stored at −20 ° C. until use.

Step 5: Purification of the Polymer Conjugate (Optional)

Tangential flow filtration (TFF) process was used to purify polymer conjugate formulations of un-incorporated components and to exchange buffer to pharmaceutically acceptable formulation vehicle. The TFF filter material was made of either modified polyethersulfone (PBS) or regenerated cellulose. The selection of molecular weight cutoff for these membranes was done with efficiency of purification and retention of polymer conjugate in mind. The processing parameters, including but not limited to feed pressure, retentate pressure, crossflow rate and filtrate flux, were set to allow reproducibility from batch to batch and linear scaling of the process. Using the difiltration mode of TFF, the reaction impurities were filtered out into the permeate and the buffer for the retained polymer conjugate is exchanged. After TFF, the final product was concentrated to 0.4-2.0 mg/mL of siRNA and sterile filtered using a 0.2 µm PES syringe filter and stored at −20° C. until use.

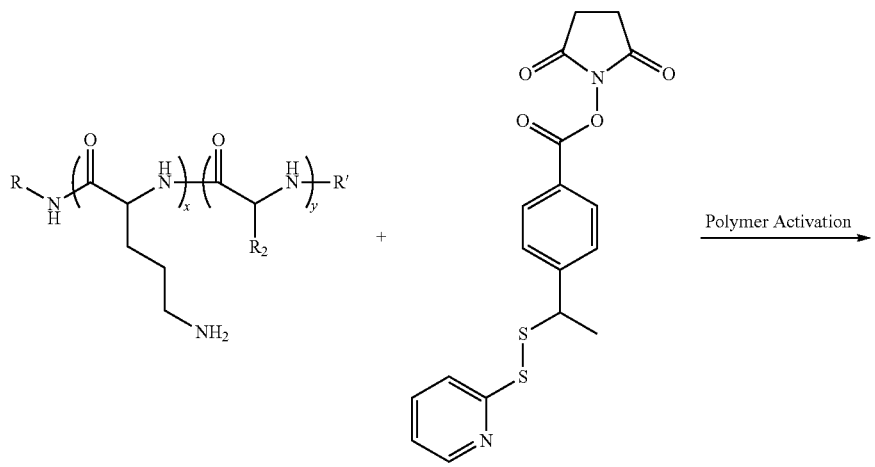

-continued
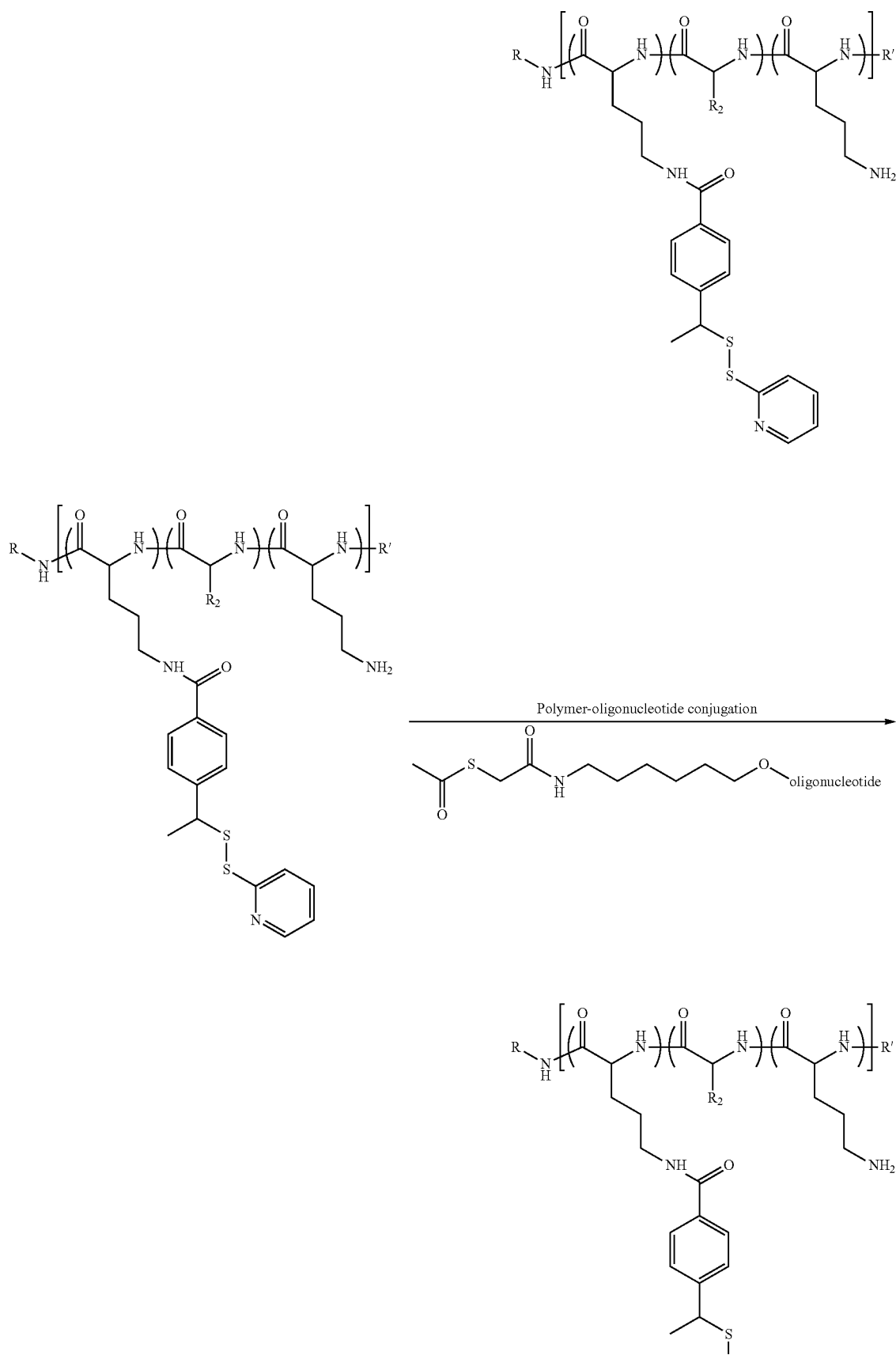

-continued
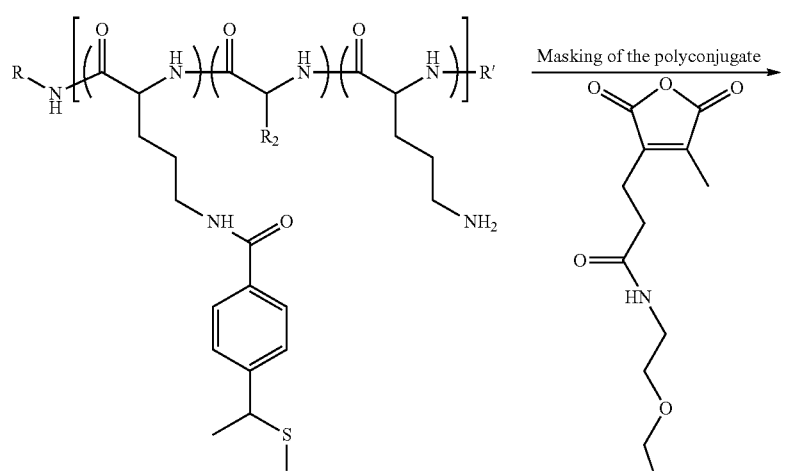
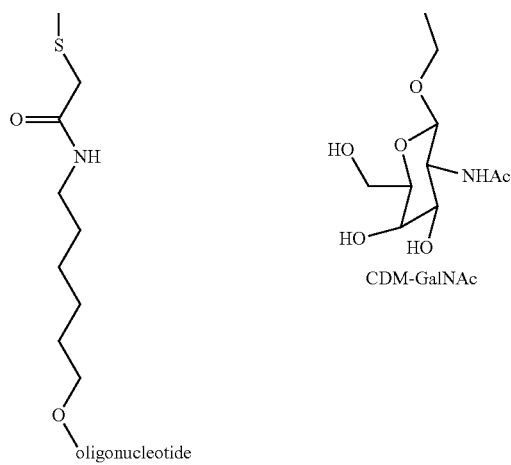

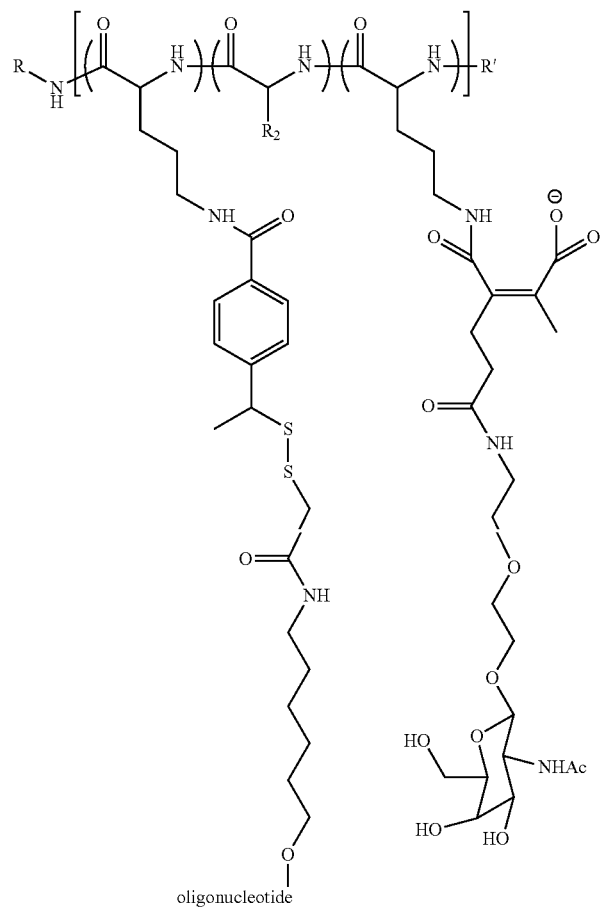
Polymer Conjugate (Scheme 5A)
Exemplary polymer conjugates of the instant invention made by the Scheme above include:
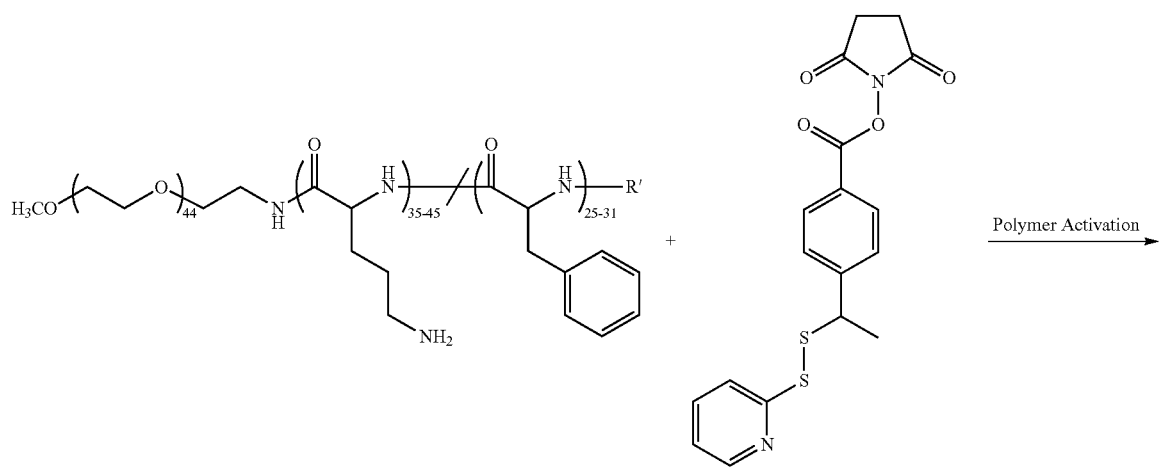

-continued
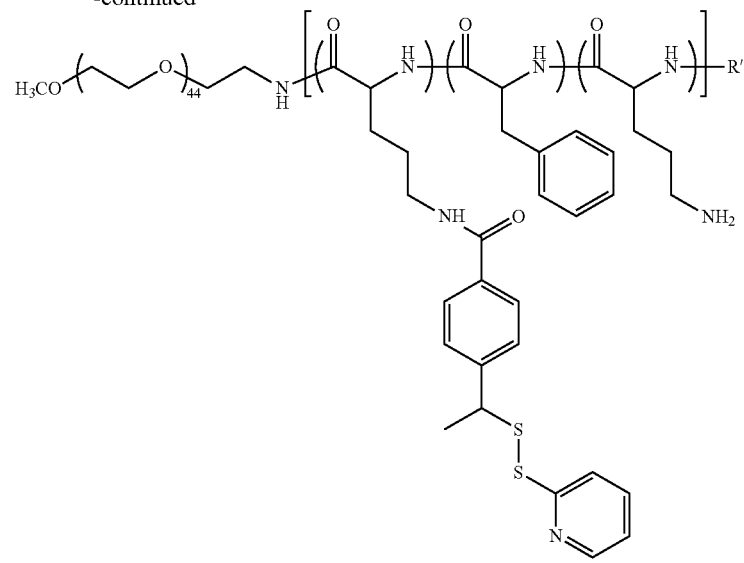
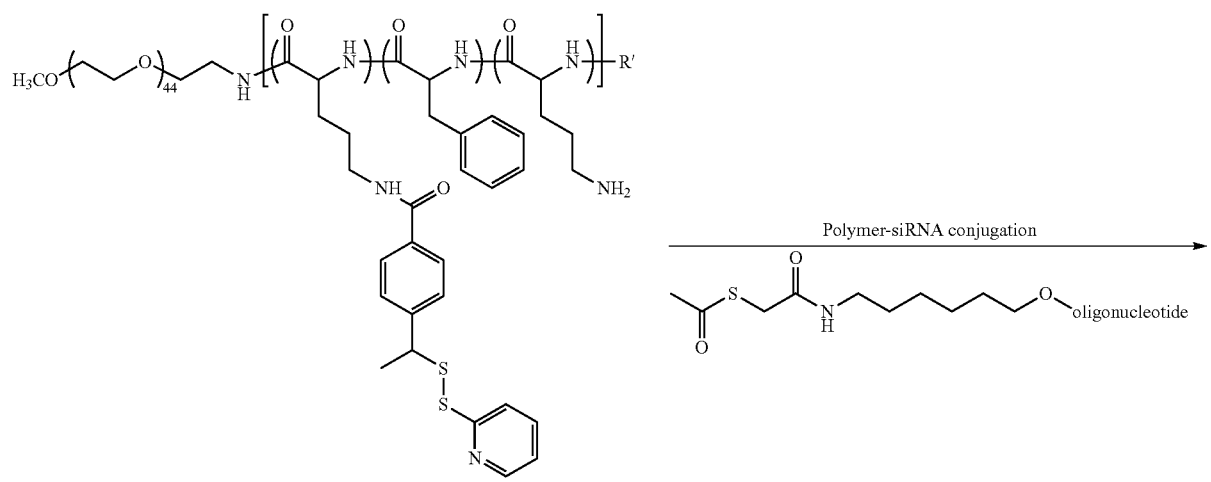
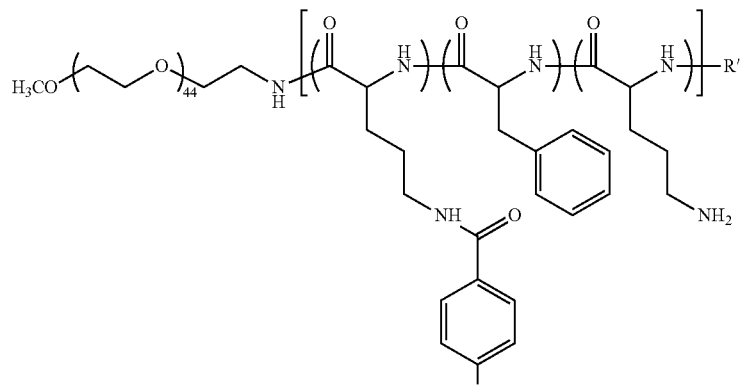

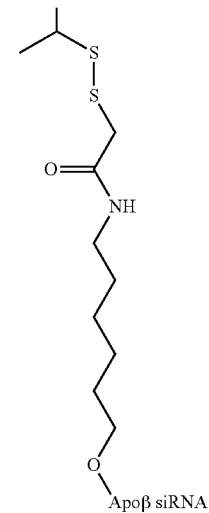
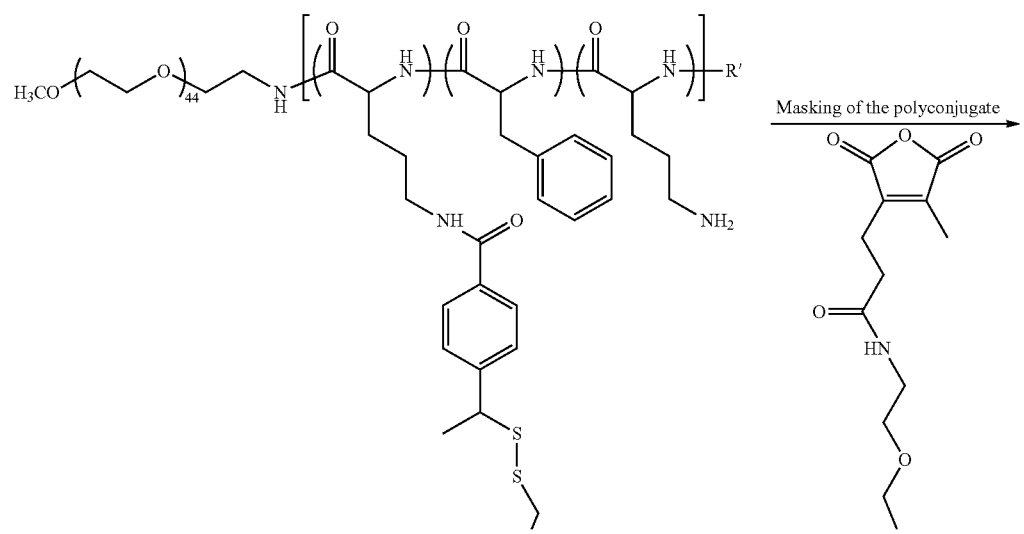
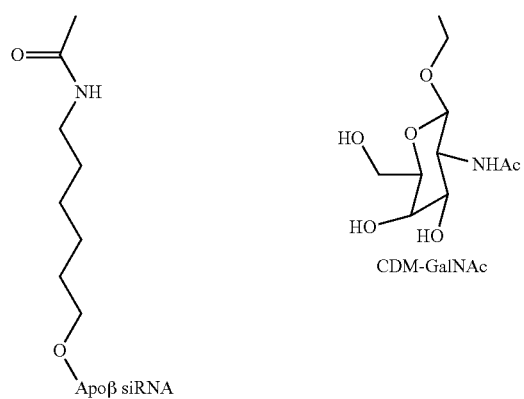

-continued
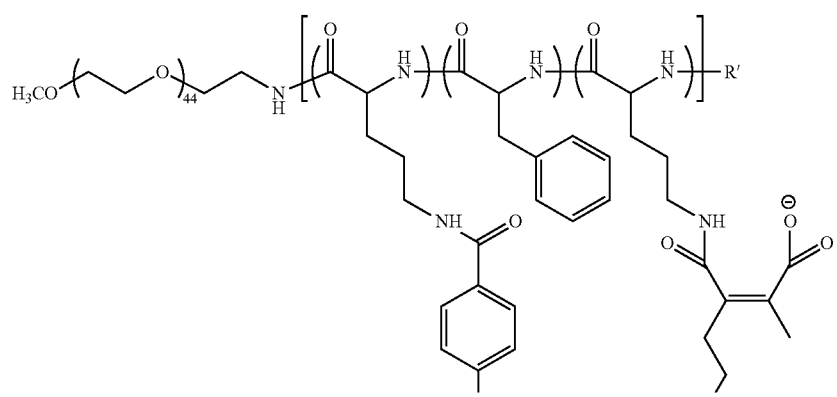
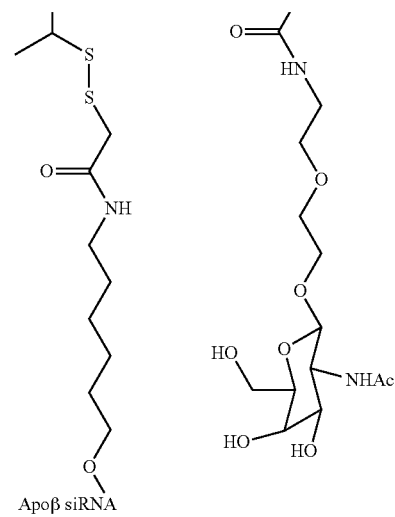
R' is an end group selected from: a hydrogen or carboxylate; and more specifically:
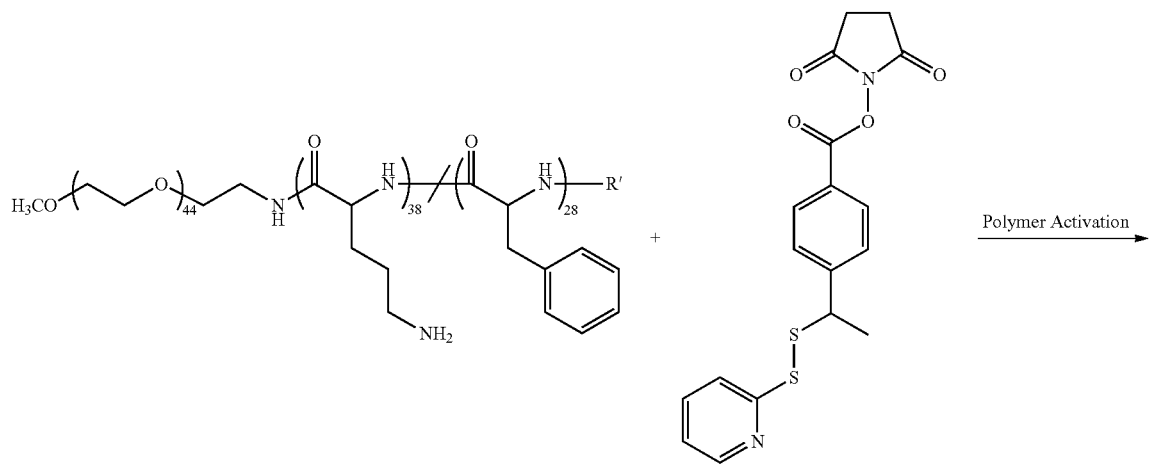

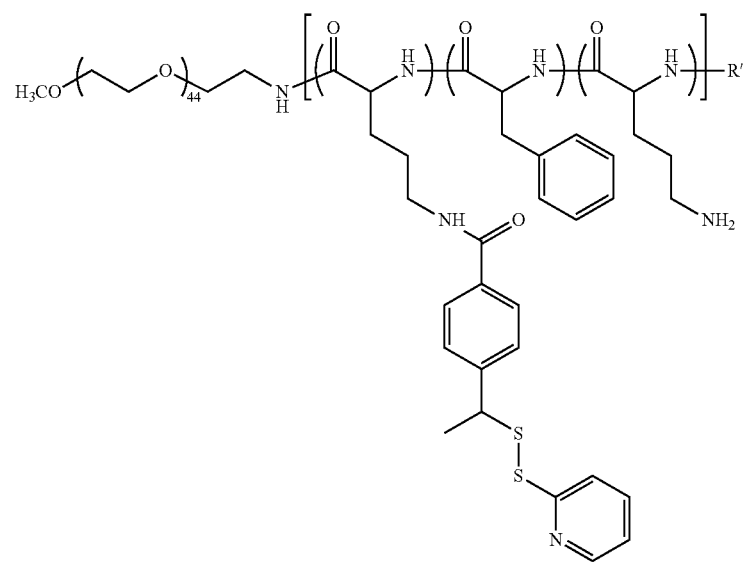
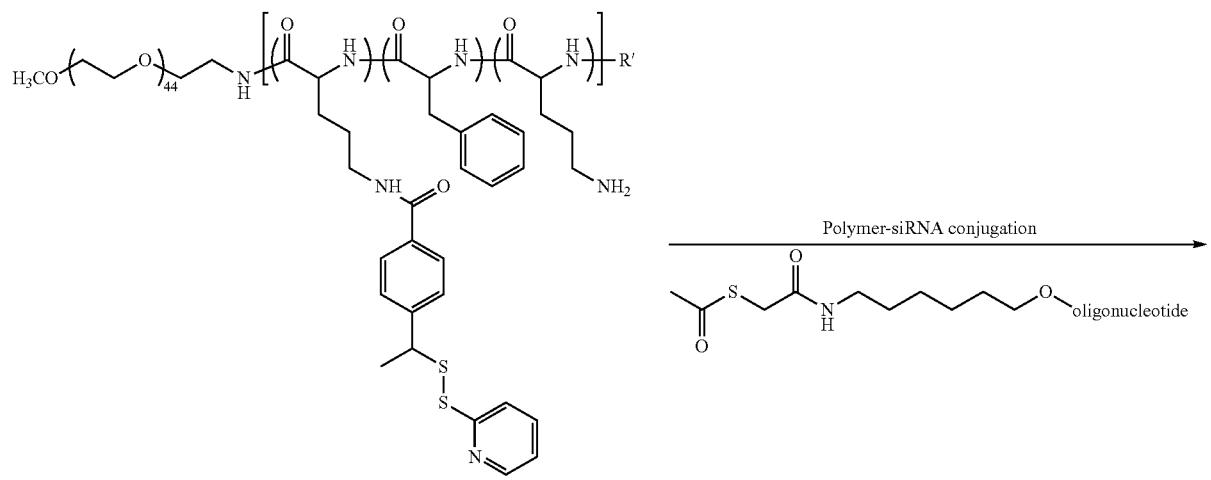
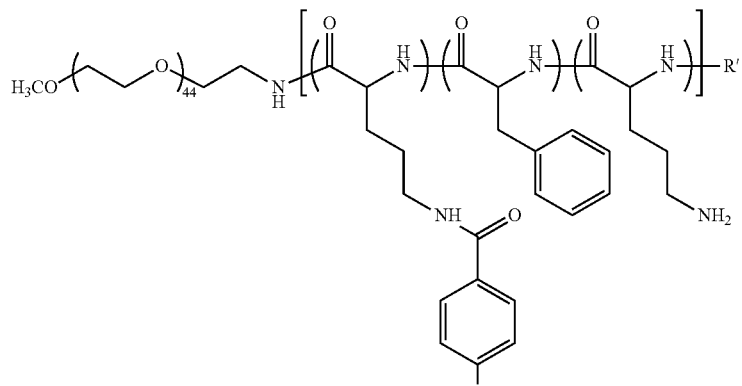

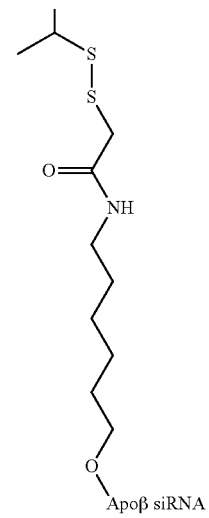
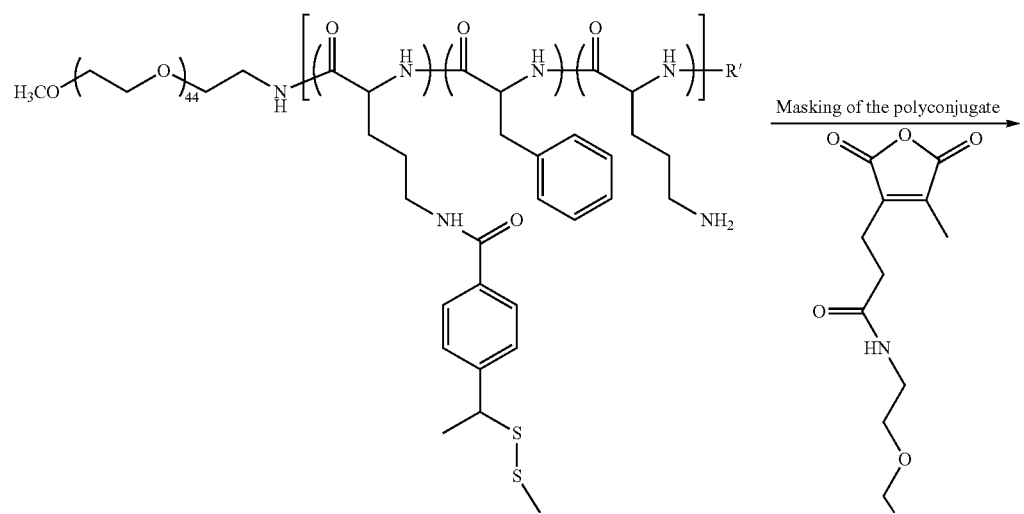
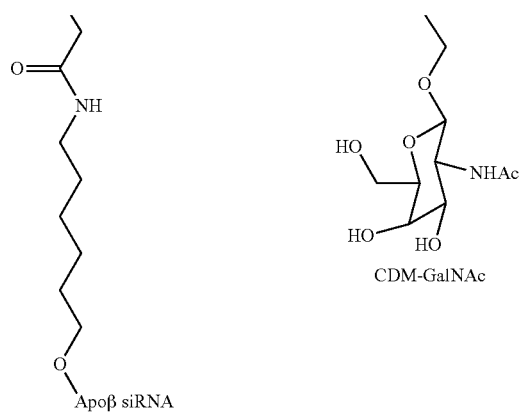

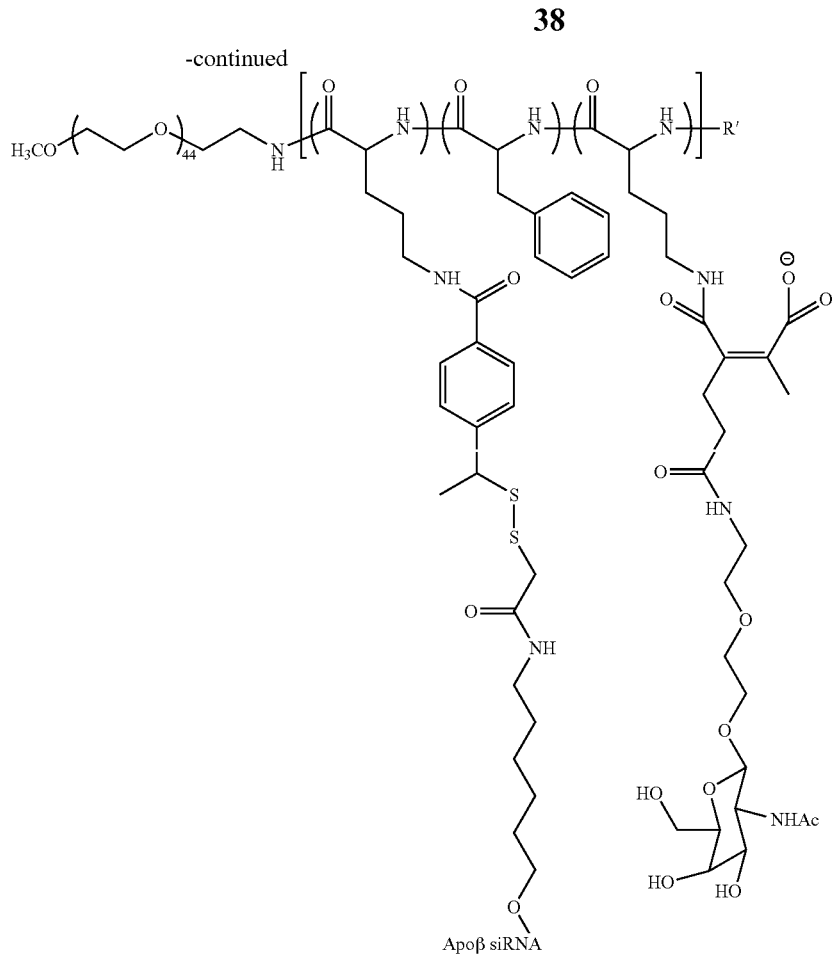

R is an end group selected from a hydrogen or carboxylate.

Polymer 2 (Scheme 4B)

Step 1: Activation of Polymer

Approximately 9.5 g of polymer is added into a 500 mL roundbottom along with 300 mL of DMSO. The solution is heated to 50° C. and mixed until the polymer is completely dissolved (approximately 20 minutes). Next, 13.5 mL of a solution of SMPT in DMSO (1 mg/100 µl) is added (corresponding to 1.5 wt % with respect to the polymer weight).

Step 2: Activation of Oligonucleotide

Oligonucleotide (1 g, 0.0714 mmol) is dissolved in 0.1M sodium bicarbonate buffer (20 ml, 50 mg/mL) in a vial with magnetic stir bar and cooled to 0-5° C. in an ice water bath. In a separate vial, SATA (83 mg, 0.357 mmol, 5 equivalents) is dissolved in 0.78 mL DMSO. The SATA solution is added over 1 min and the clear, colorless reaction mixture stirred at 0-5° C. for 2 h. After 2 h, the reaction mixture is sampled and analyzed by UPLC or HPLC for completion of the conjugation. If >5% oligonucleotide remains unreacted, another charge of SATA in DMSO (2.0 equivalents) is added and the reaction aged at 0-5° C. for completion of the SATA conjugation (confirmation by HPLC or UPLC). When there is <5% unreacted oligonucleotide remaining by UPLC or HPLC, the reaction mixture is purified by TFF dialysis using water (~2 L) or PD10 column to remove any remaining SATA/succinimides. The recovered purified solution is lyophilized to a white fluffy solid. The recovery is typically around 95% and the purity is greater than 70% by UPLC.

Step 3: Polymer-oligonucleotide Conjugation

The activated polymer is diluted with 100 mM TRIS buffer at pH=9 resulting in a final polymer concentration of w 4.5 mg/mL. About 900 mg of oligonucleotide is added to the activated polymer solution and allowed to react at room temperature for one hour.

Step 4: Masking of Polymer Conjugate

In a separate vial, 27.9 g of carboxydimethylmaleic anhydride-N-acetylgalactosamine (CDM-GalNAc) and 14.3 g of carboxydimethylmaleic anhydride poly(ethylene glycol, CDM-PEG) is weighed out, then a 350 mg/mL solution of CDM in DMSO is prepared. The CDM solution (121 mL) is added to the siRNA-polymer conjugate solution and stirred for 10 minutes at room temperature. The polyconjugate solution is stored at −20 ° C. until use.

Step 5: Purification of the Polymer Conjugate (Optional)

Tangential flow filtration (TFF) process was used to purify polymer conjugate formulations of un-incorporated components and to exchange buffer to pharmaceutically acceptable formulation vehicle. The TFF filter material was made of either modified polyethersulfone (PES) or regenerated cellulose. The selection of molecular weight cutoff for these membranes was done with efficiency of purification and retention of polymer conjugate in mind. The processing parameters, including but not limited to feed pressure, retentate pressure, crossflow rate and filtrate flux, were set to allow reproducibility from batch to batch and linear scaling of the process. Using the difiltration mode of TFF, the reaction impurities were filtered out into the permeate and the buffer for the retained polymer conjugate is exchanged. After TFF, the final product was concentrated to 0.4-2.0 mg/mL of siRNA and sterile filtered using a 0.2 µm PBS syringe filter and stored at −20° C. until use.
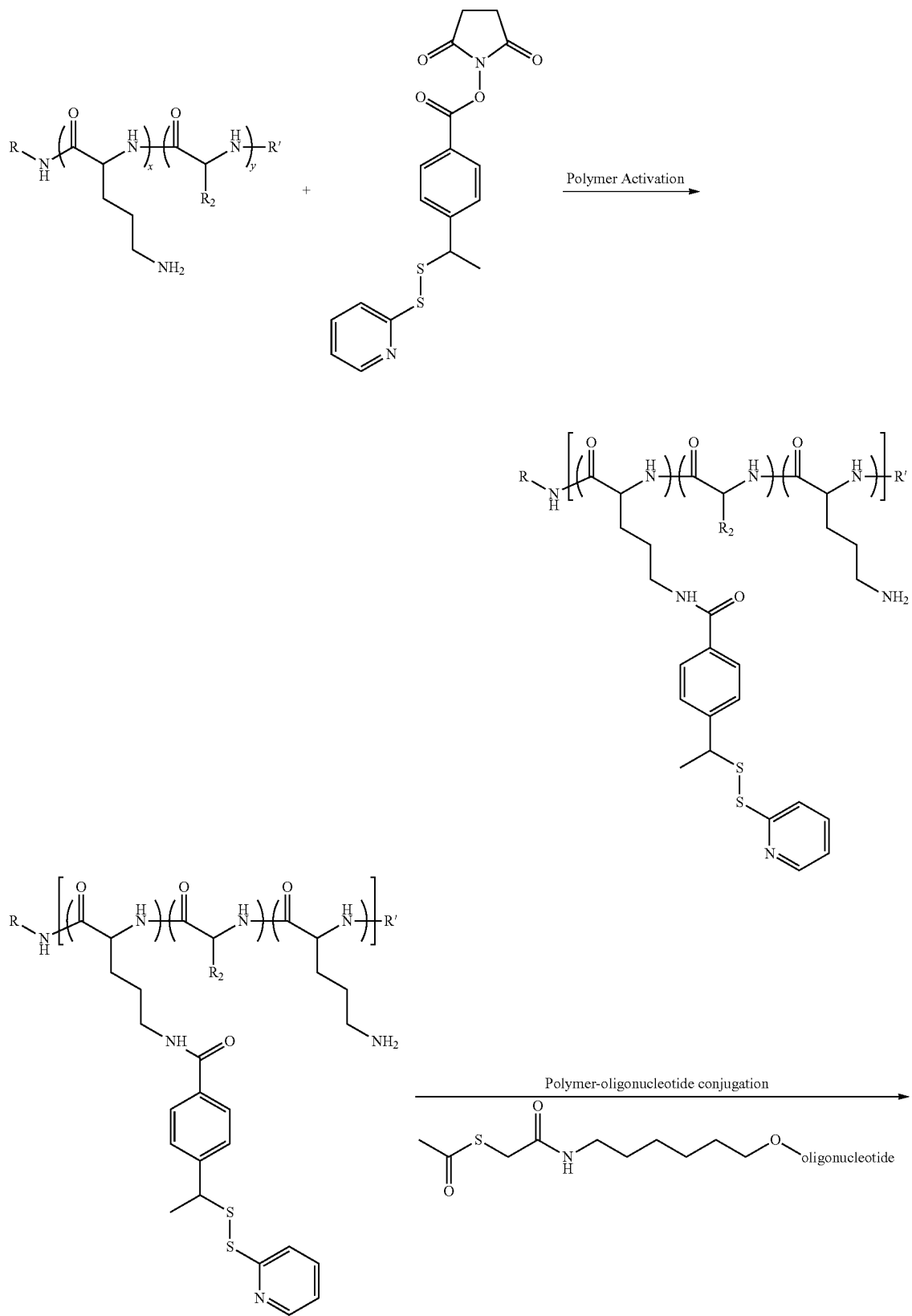

-continued
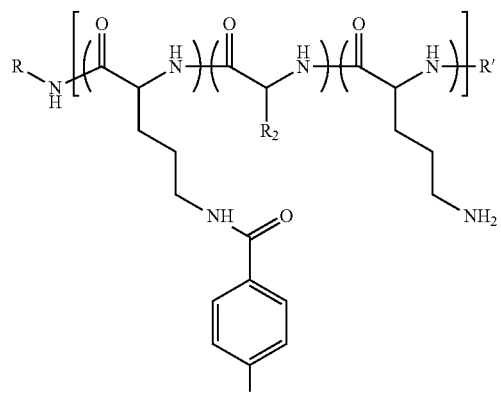
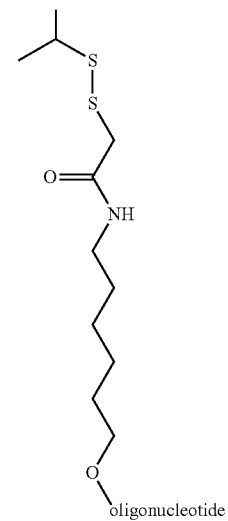
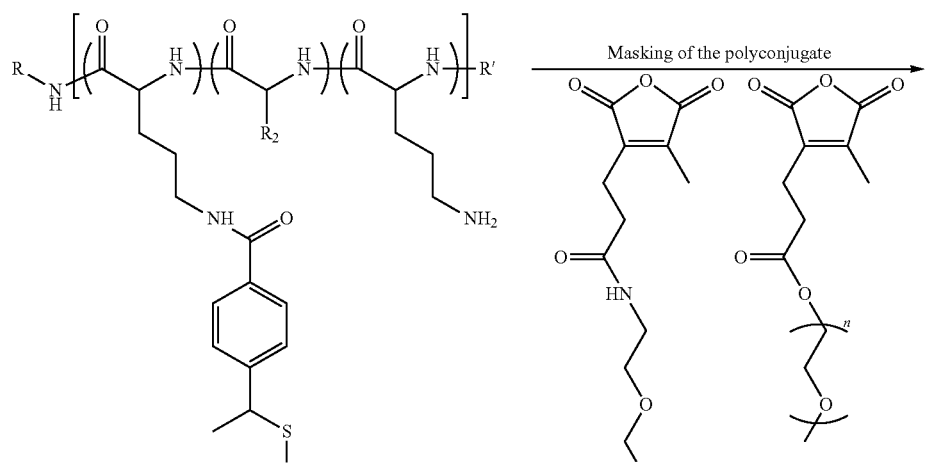
Masking of the polyconjugate

-continued
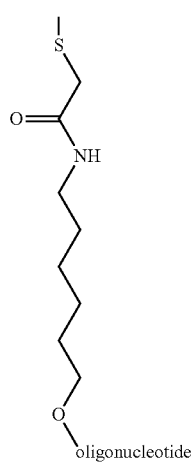
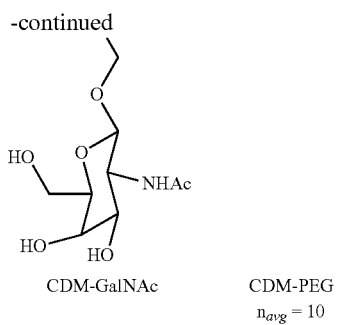
CDM-GalNAc     CDM-PEG $n_{avg} = 10$
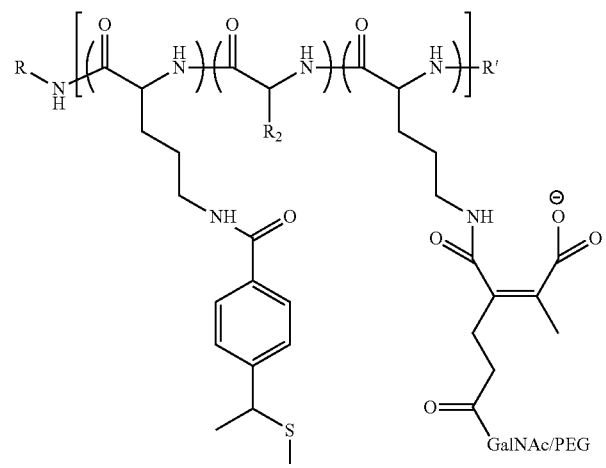
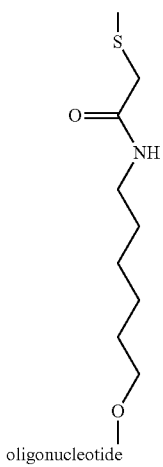

Polymer Conjugate (Scheme 5B)
Exemplary polymer conjugates of the instant invention made by the Scheme above include:
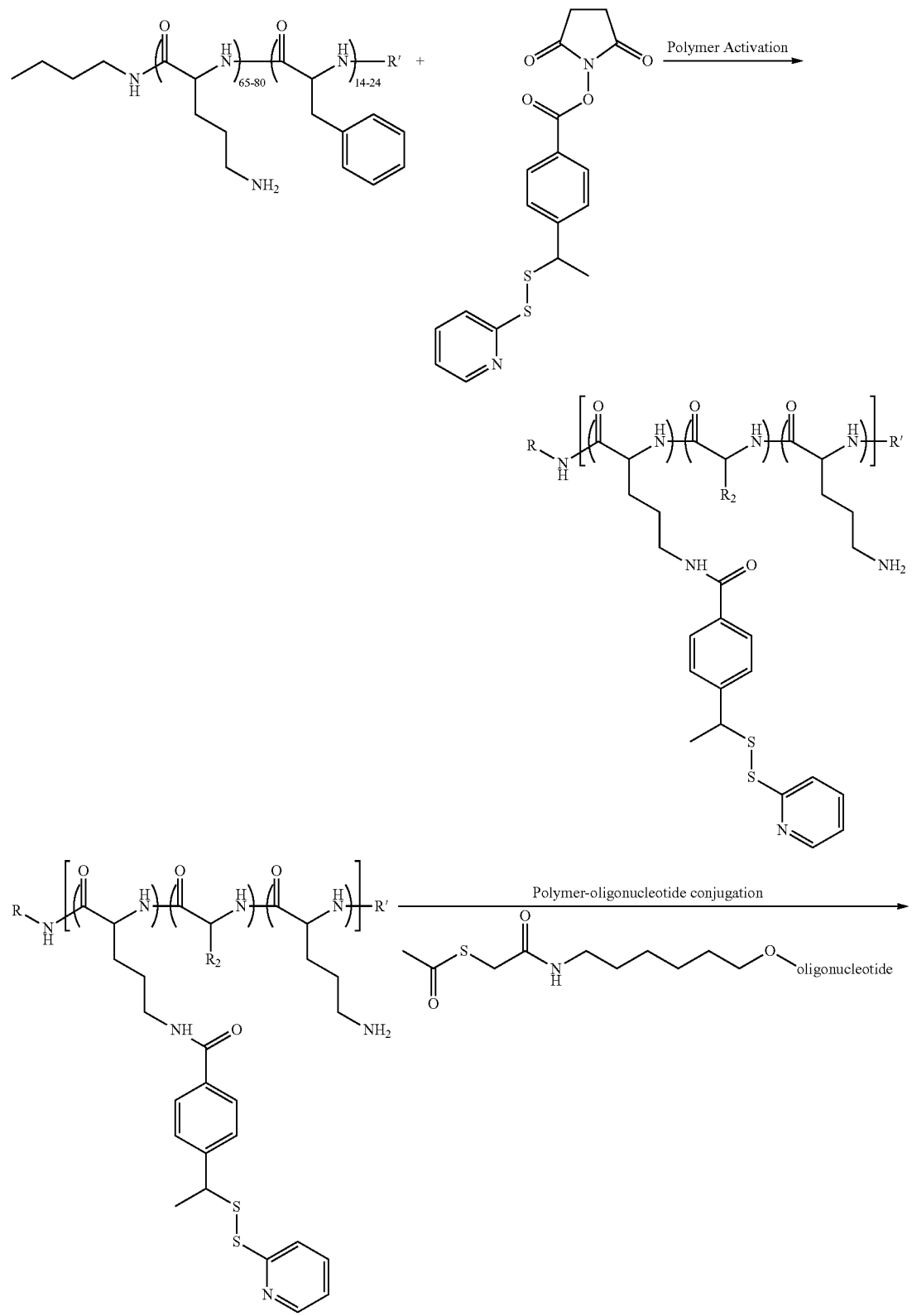

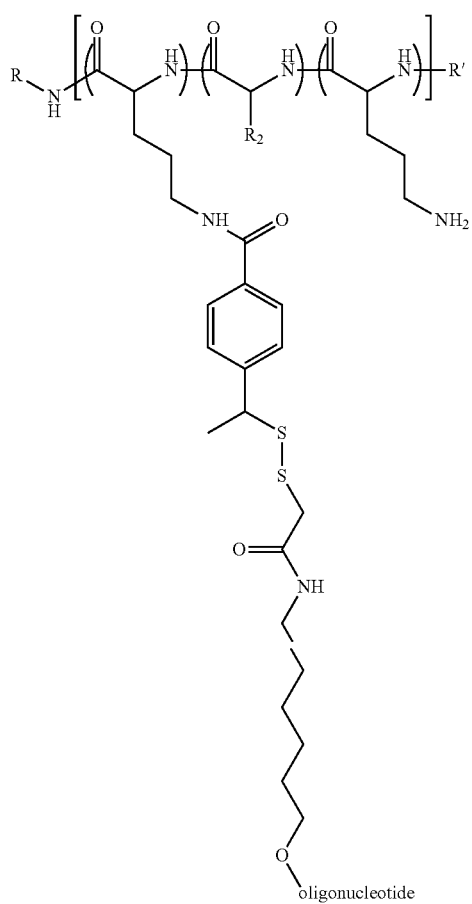
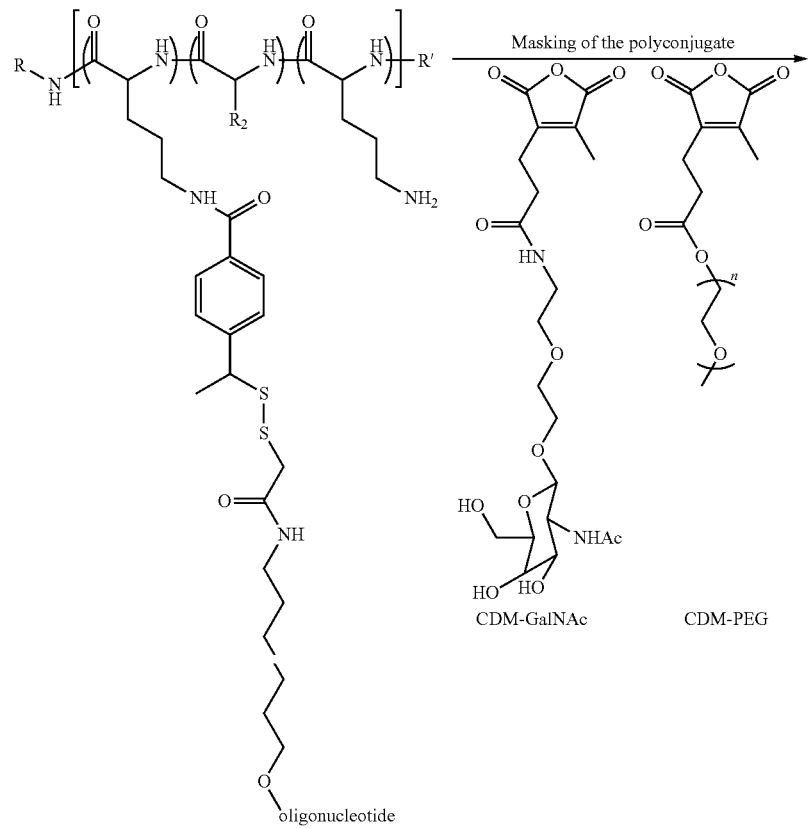

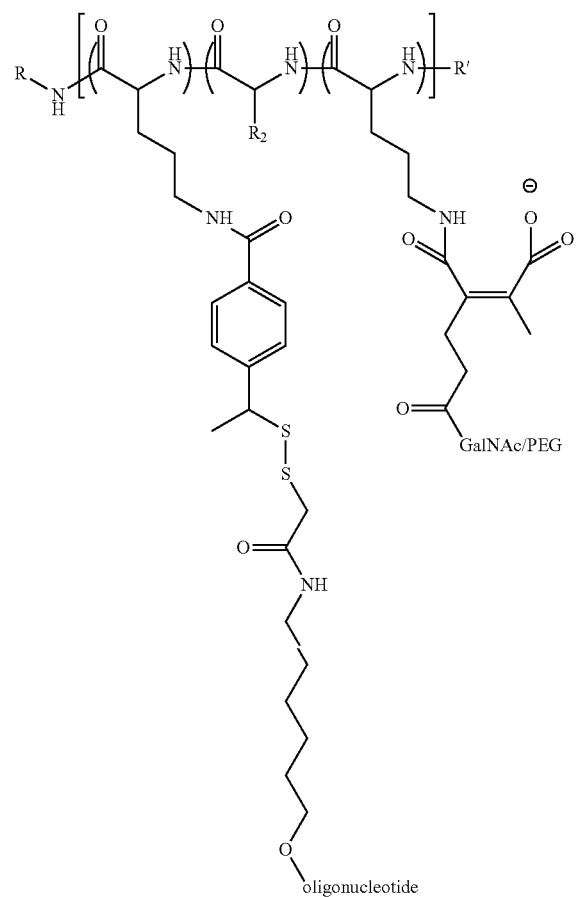
$n_{avg} = 10$
R' is an end group selected from: a hydrogen or carboxylate; and more specifically:
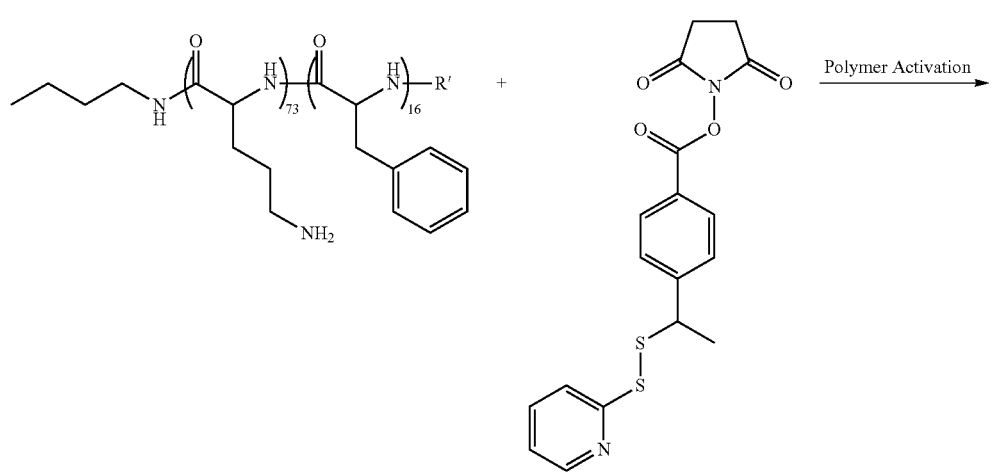

-continued
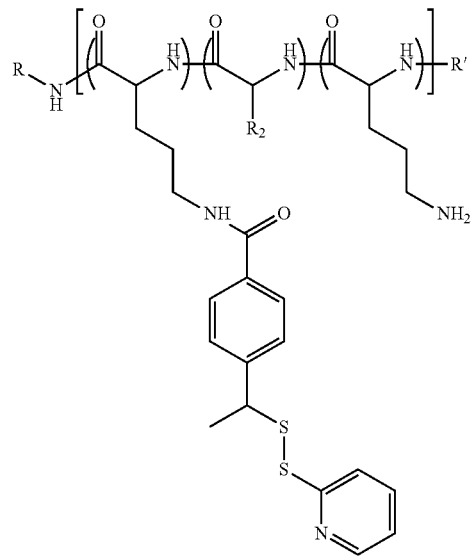
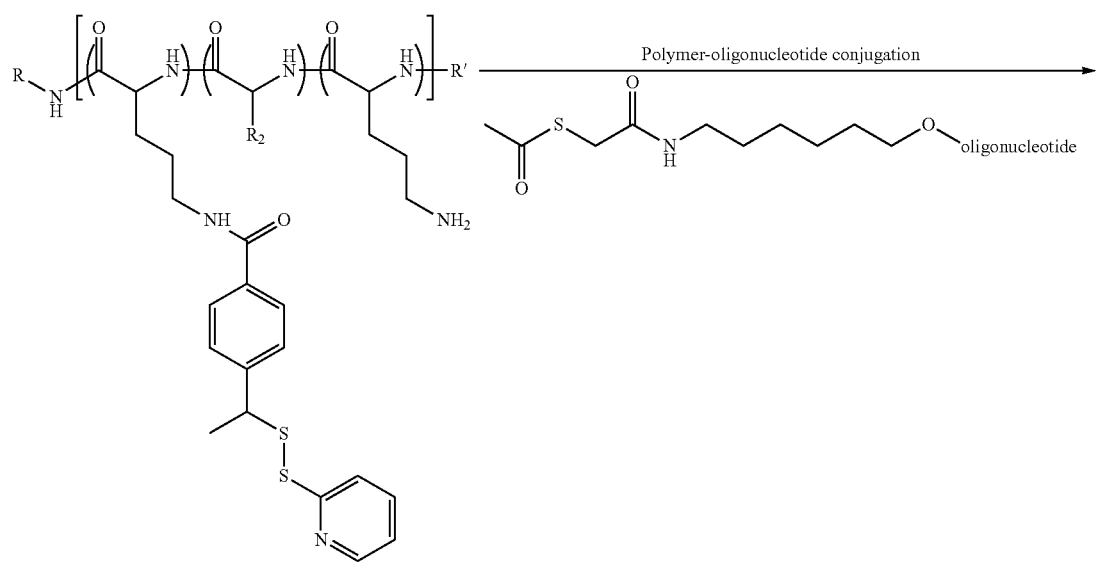

-continued
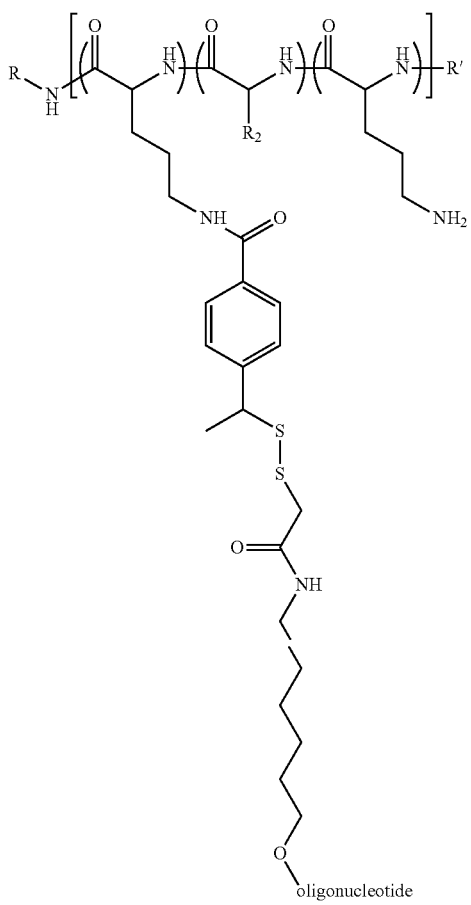
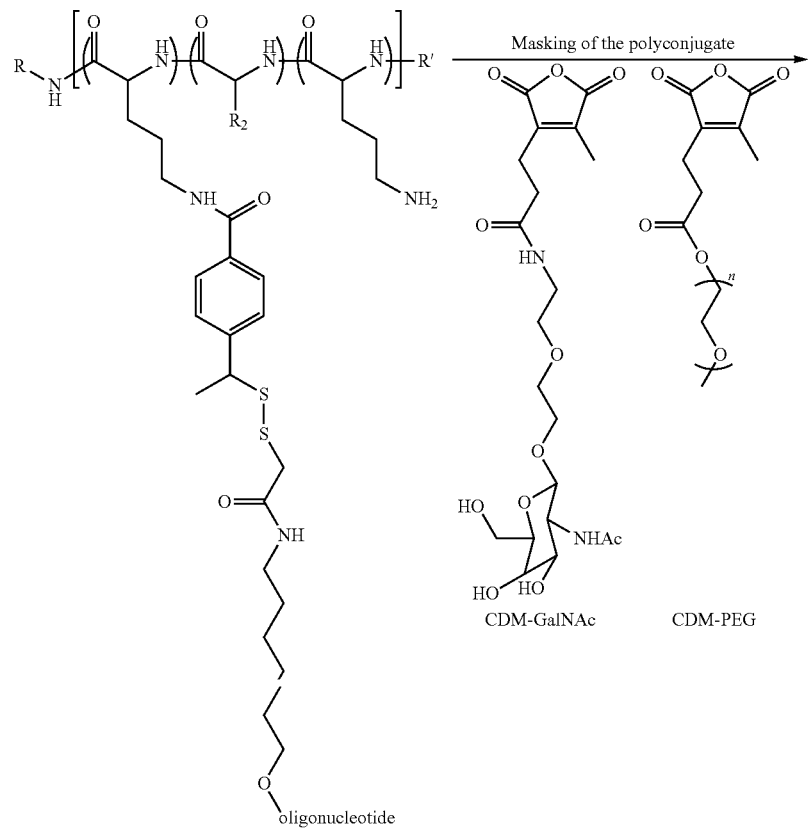
CDM-GalNAc    CDM-PEG

-continued

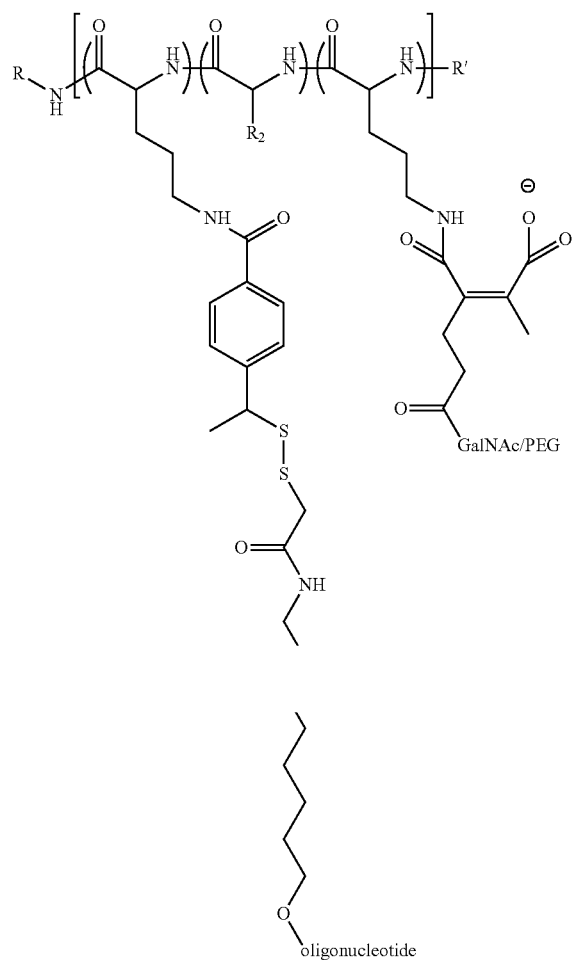

$n_{avg} = 10$

R' is an end group selected from: a hydrogen or carboxylate.

Tables and Data

TABLE 1

Examining the ratio of GalNAc to PEG

| Initiator | Monomer 1 | Monomer 2 | Ratio of Monomers (1:2) | Mn (g/mol) | Polymer Architecture | Masking Strategy | Polymer: siRNA (w/w) | siRNA Dose (mpk) | mRNA KD (%) |
|---|---|---|---|---|---|---|---|---|---|
| n-Bu | L-ORN | L-PHE | 4:1 | 11 | Block | ALL GalNAc | 5 | 1 | 0 |
| n-Bu | L-ORN | L-PHE | 4:1 | 11 | Block | 3:1 GalNAc:PEG | 5 | 1 | 6 |
| n-Bu | L-ORN | L-PHE | 4:1 | 11 | Block | 1:1 GalNAc:PEG | 5 | 1 | 61 |
| n-Bu | L-ORN | L-PHE | 4:1 | 11 | Block | 1:3 GalNAc:PEG | 5 | 1 | 83 |
| n-Bu | L-ORN | L-PHE | 4:1 | 11 | Block | ALL PEG | 5 | 1 | 0 |
| n-Bu | L-ORN | L-PHE | 4:1 | 11 | Block | 3:1 GalNAc:PEG | 2.5 | 1 | 13 |

End point = 5 days
Species = Rat
siRNA = Sci10 ApoB

The conjugation procedure followed was that described in the "conjugation" section, with the following exception:

Step 4: Masking of Polymer Conjugate

In this step, the appropriate amount of CDM-GalNAc and CDM-PEG were weighed out such that the weight ratio was equal to ALL GalNAc, 3:1 GalNAc:PEG, 1:1 GalNAc:PEG, 1:3 GalNAc:PEG, or ALL PEG, respectively. The rest of the conjugation procedure was followed according to what was earlier described.

TABLE 2

Investigating the efficacy of polyconjugates made using different siRNAs

| siRNA Descriptor | Initiator | Monomer 1 | Monomer 2 | Ratio of Monomers | Mn (g/mol) | Polymer Architecture | Masking Strategy | Polymer: siRNA (w/w) | siRNA Dose (mpk) | mRNA KD (%) |
|---|---|---|---|---|---|---|---|---|---|---|
| ApoB | n-Bu | L-ORN | L-PHE | 4:1 | 11 | Block | 1:3 GalNAc:PEG | 5 | 1 | 83 |
| SSB | n-Bu | L-ORN | L-PHE | 5:1 | 11 | Block | 1:3 GalNAc:PEG | 5 | 1 | 82 |

End point = 5 days

Species = Rat

The conjugation procedure followed was that described in the "conjugation" section, with the exception of the siRNA sequence.

SSB Sequence:

[6amiL][iB][fluA][omeC][fluA][fluA][omeC][fluA][fluG][fluA][omeC][omeU][omeU]

[omeU][fluA][fluA][omeU][fluG][omeU][fluA][fluA][dTs]dT[iB]

[fluU][fluU][dA][omeC][fluA][omeU][omeU][fluA][fluA][fluA][fluG][omeU][omeC]

[fluU][fluG][omeU][omeU][fluG][omeU][omeUs][omeU]

TABLE 3

Probing the stereochemistry of the Ornithine monomer

| Initiator | Monomer 1 | Monomer 2 | Ratio of Monomers | Mn (g/mol) | Polymer Architecture | Masking Strategy | Polymer: siRNA (w/w) | siRNA Dose (mpk) | mRNA KD (%) |
|---|---|---|---|---|---|---|---|---|---|
| n-Bu | L-ORN | L-PHE | 4:1 | 11 | Block | 3:1 GalNAc:PEG | 5 | 1 | 44 |
| n-Bu | D-ORN | L-PHE | 4:1 | 10 | Block | 3:1 GalNAc:PEG | 5 | 1 | 59 |

End point = 5 days

Species = Rat siRNA = Sci10 ApoB

The following monomers were synthesized using the same general procedure as above (see monomer synthesis in the examples section), with the exception of the following conditions [stereochemistry of the starting material]:

| Starting Amino Acid | Name | Temp (° C.) | Solvent | Yield (%) |
|---|---|---|---|---|
| [structure] | D-Ornithine | 50 | THF | 82 |

Polymerization and conjugation chemistry followed the same procedure as outlined in the examples section above.

TABLE 4

Changing the targeting group from a pH-reversible group (CDM) to a non-labile group

| Initiator | Monomer 1 | Monomer 2 | Ratio of Monomers | Mn (g/mol) | Polymer Architecture | Masking Strategy | Polymer: siRNA (w/w) | siRNA Dose (mpk) | mRNA KD (%) |
|---|---|---|---|---|---|---|---|---|---|
| n-Bu | L-ORN | L-PHE | 4:1 | 9 | Block | 0.5 mol % non-labile triGalNAc, ALL PEG masking | 5 | 1 | 13 |
| n-Bu | L-ORN | L-PHE | 4:1 | 9 | Block | 1 mol % non-labile triGalNAc, ALL PEG masking | 5 | 1 | 67 |
| n-Bu | L-ORN | L-PHE | 4:1 | 9 | Block | 3 mol % non-labile triGalNAc, ALL PEG masking | 5 | 1 | 64 |
| n-Bu | L-ORN | L-PHE | 4:1 | 9 | Block | 5 mol % non-labile triGalNAc, ALL PEG masking | 5 | 1 | 44 |

End point = 48 hours
Species = Rat
siRNA = Sci10 ApoB

Differences from previously described "conjugation" section include: the use of a non-labile targeting ligand, with ALL PEG masking of the remaining primary amines. For these conjugations, Step 1 involved dissolving the polymer in DMSO at 50° C. for 30 minutes, followed by the addition of the NHS-triGalNAc, which was allowed to stir for 15 minutes. The polymer was then diluted into the appropriate amount of 100 mM TRIS, pH=9 and allowed to mix for 10 minutes. The SMPT was then added, and allowed 10 minutes to react. The remaining of the conjugation was followed according to steps 3 and 4 (although it was CDM-PEG only in step 4) from the above procedure.

The synthesis of the non-labile targeting ligand (triGalNAc-NHS) is described below:

61 62
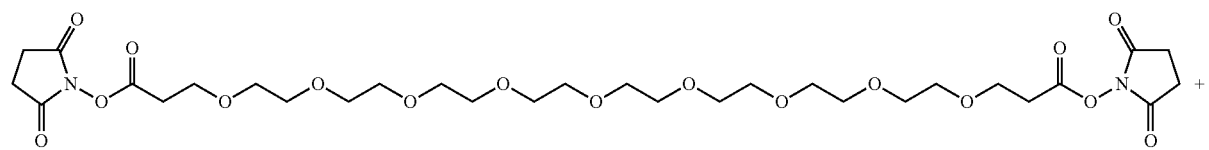
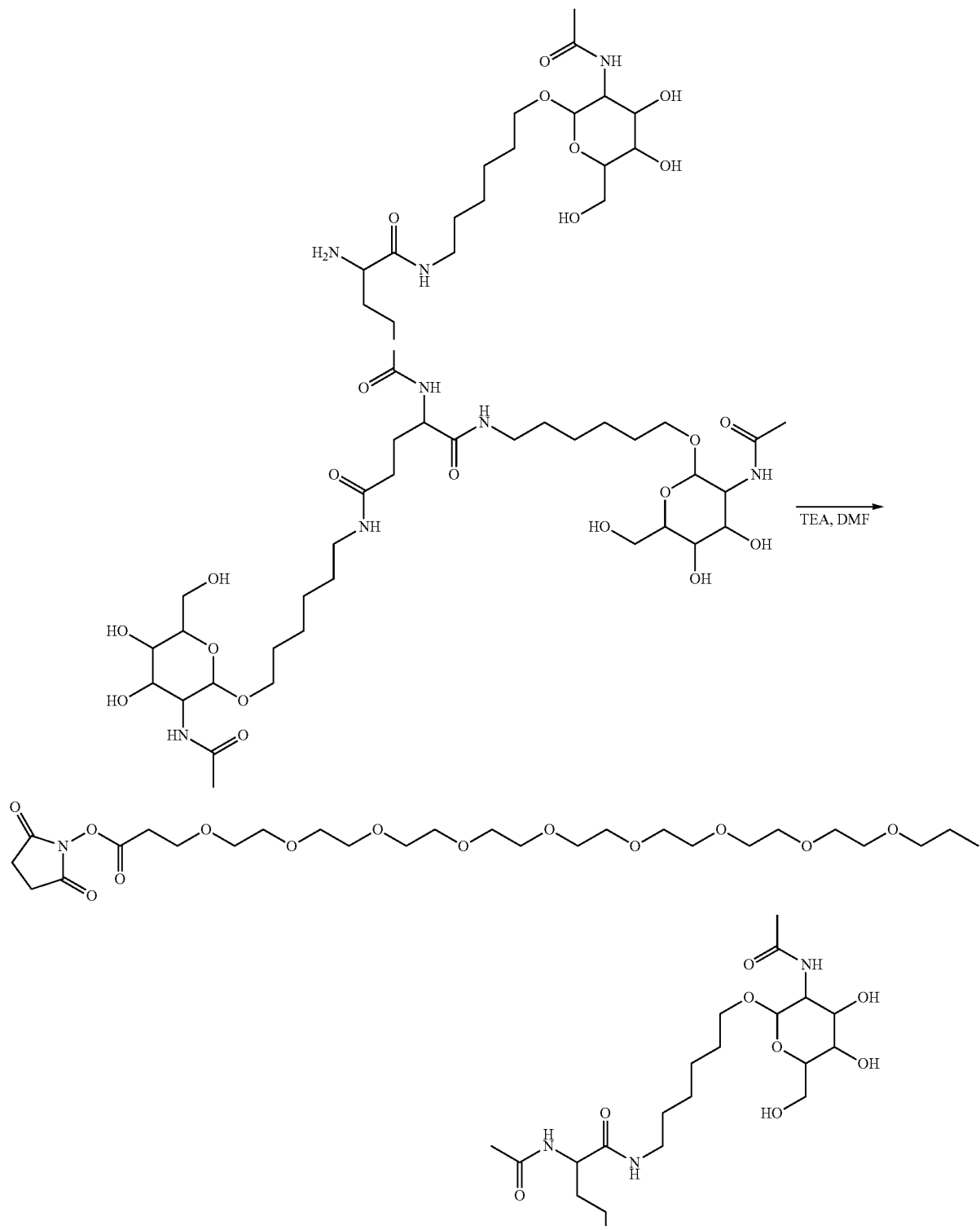

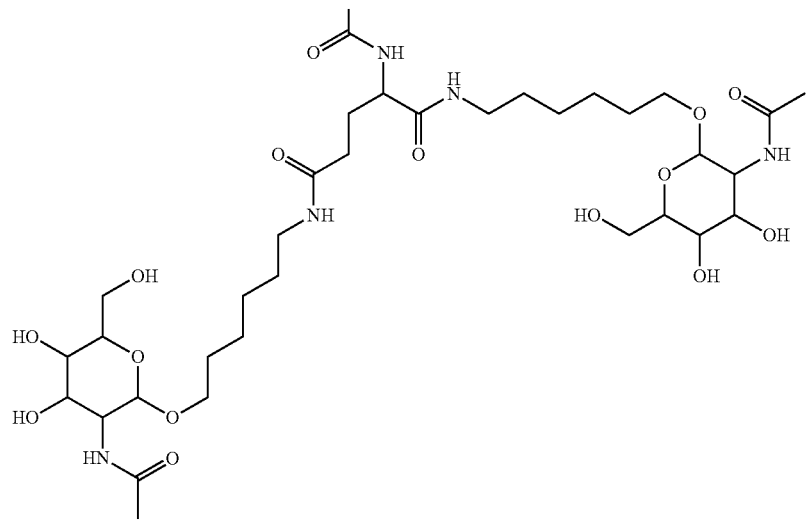

A-1

N-(6-{[2-(acetylamino)-2-deoxy-β-D-galactopyrano-syl]oxy}hexyl)-N2-{31-[(2,5-dioxopyrrolidin-1-yl)oxy]-31-oxo-4,7,10,13,16,19,22,25,28-nonaoxahentriacontan-1-oyl}-L-α-glutaminyl-N1,N5-bis(6-{[2-(acetylamino)-2-deoxy-β-D-galactopyranosyl]oxy}hexyl)-L-glutamamide To 85 mg (0.120 mmol) of Bis-dPEG®9-NHS ester in 0.30 ml of DMSO was added 0.084 ml (0.600 mmol) of triethylamine followed by a solution of 156 mg (0.132 mmol) of EE(GalNAc)3[1] in 0.7 ml of DMSO portionwise over 30 minutes and the mixture was stirred for an additional 60 minutes at room temperature. Crude reaction was quenched by the addition of 1 ml of water containing 0.055 mL (0.007 mmol) of trifluoroacetic acid and purified directly by preparative HPLC on a Waters SunFire C18 OBD 5 μm 30×150 mm column utilizing a gradient of 100% water (0.05% TFA) to 20% water/CH$_3$CN (0.05% TFA). Freeze drying provided A-1 as a white solid. Data for A-1: LC/MS: rt=0.73 min; m/z (M+H)=1778.4 found; 1778.0 required; HRMS (ESI) m/z, (M+H)=1776.9243 found; 1776.9254 required.

(1) Lee, R. T.; Lee, Y. C., *Glycoconjugate J.* 1987, 4, 317-328.

TABLE 5

| | | | | | | | |
|---|---|---|---|---|---|---|---|
| Initiator | Monomer 1 | Mn (g/mol) | Polymer Architecture | Masking Strategy | Polymer: siRNA (w/w) | siRNA Dose (mpk) | mRNA KD (%) |
| C8-Cholesterol | L-ORN | 10 | Block | 1:3 GalNAc:PEG | 5 | 1 | 17 |
| INF7 | L-ORN | 14 | Block | 1:3 GalNAc:PEG | 5 | 1 | 61 |
| DSPE-2kDa | L-ORN | 14 | Block | 1:3 GalNAc:PEG | 5 | 1 | 41 |
| n-heptadecane | L-ORN | 15 | Block | 1:3 GalNAc:PEG | 5 | 1 | 17 |

End point = 48 hours
Species = Rat
siRNA = Sci10 ApoB

Initiator:

INF7 peptides: These peptides were obtained from GenScript with N-terminal modified with 6-aminohexanoic acid (Ahx) as TFA salts. To free base the amine, these peptides were desalted with 50 mM CsOH 10% ACN/H$_2$O solution and dialyzed with 10% trifluoroethanol in water followed by lyophilization.

INF7: Ahx-GLFEAIEGFIENGWEGMIDGWYG

Cholesterol—C8—amine:

Cholesterol—C8—amine was prepared from a literature procedure[1]

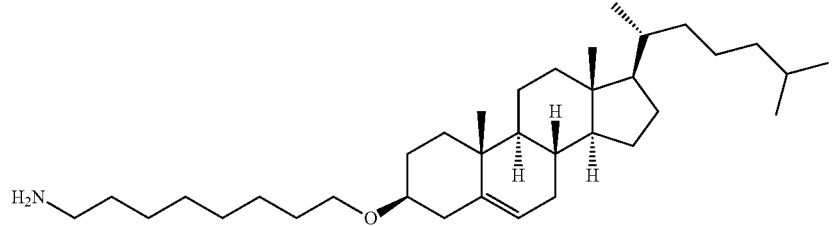

1:Ref A. Zimmer, S. Atmaca-Abdel Aziz, M Gilbert, D. Werner, C. R. Noe European Journal of Pharmaceutics and Biopharmaceutics 47 (1999) 175-478

1,2-distearoyl-sn-glycero-3-phosphoethanolamine-N-[amino(polyethylene glycol)-2000 (DSPE-2K-PEG):

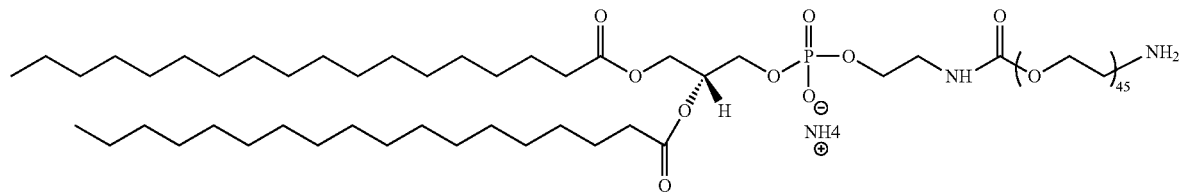

DEPE-2K PEG was purchased from Avanti Polar Lipids.

n-heptadecane;

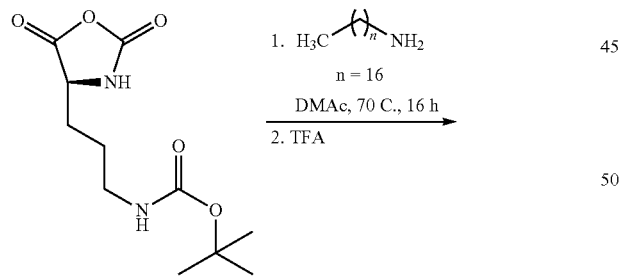

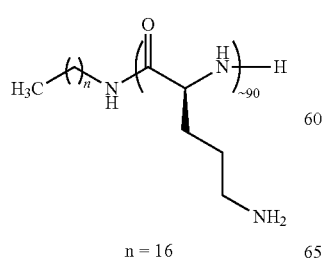

n = 16

Polymerization was carried out using standard polymerization and deprotection conditions (see polymer synthesis section under examples).

TABLE 6

Changing the counterion from the primary amine side chain

| Initiator | Monomer 1 | Monomer 2 | Ratio of Monomers | Mn (g/mol) | Polymer Archit. | Counterion for polymer | Masking Strategy | Polymer: siRNA (w/w) | siRNA Dose (mpk) | mRNA KD (%) |
|---|---|---|---|---|---|---|---|---|---|---|
| n-Bu | L-ORN | L-PHE | 4:1 | 11 | Block | TFA | 3:1 GalNAc: PEG | 5 | 3 | 67 |
| n-Bu | L-ORN | L-PHE | 5:1 | 11 | Block | HBr | 3:1 GalNAc: PEG | 5 | 3 | 79 |

End point = 5 days
Species = Rat
siRNA = Sci10 ApoB

According to the polymerization procedures described in the examples section, the counterion would be TFA. If however, a different protecting group is used to protect the primary amine during polymerization (example: Carbobenzyloxy, or Cbz), a different counterion to the primary amine is obtained once deprotected due to differences in the deprotecting procedure. In this example (line 2), a Cbz protecting group was used to protect the primary amine off the side chain of ornithine, and HBr/HOAc was used to deprotect the amine. The polymerization chemistry was not altered with the alternate protecting groups, therefore only the monomer synthesis and deprotection chemistry was described below;

Monomer Synthesis:
Cbz-L-Ornithine N-Carboxyanhydride (NCA):
Day 1:
At room temperature, 40.0 g of Cbz-L-ornithine was mixed with 400 mL of THF (40 ppm water) in a 1 L round bottom flask equipped with a condenser and overhead stirrer. To the slurry was added triphosgene solid 17.8 g. After 20 min at room temperature, the reaction was aged at 50-55° C. for 3.5 h and monitored by HPLC (see below for details). Upon complete conversion of Cbz-L-ornithine to the Cbz-L-ornithine NCA, at which point the reaction was clear and homogeneous, the mixture was cooled to −10° C., carefully quenched with cold water such that the temperature was kept below or equal to 5° C., then extracted with 400 mL of isopropylacetate (IPAc), washed again with cold water twice (200 mL×2), maintaining the temperature between 0 and 5° C. After separation, the organic layer was kept at 5° C. overnight.

Day 2:
The organic layer was filtered through a silica pad (200 g prewet with THF). The silica was washed with 800 mL of THF. The resulting THF solution was concentrated, switch to IPA concentrating to 140 mL. Hexanes (400 mL) was added over 1 h, and the slurry was aged for 0.5 h, filtered, and the solid was washed with 120 mL of IPAc/Hex (1:2), then dried under vacuum at room temperature overnight.

Day 3:
A white crystalline powder was obtained (35.6 g).
Solid was collected and stored at −20° C. in a sealed bottle.
$^1$H NMR (500 MHz, DMSO-$d_6$): δ 9.08 (s, 1 H); 6.86 (s, 1 H); 4.44 (t, J=6.15 Hz, 1 H); 2.92 (q, J=6.41 Hz, 2 H); 1.75-1.67 (m, 1 H); 1.65-1.57 (m, 1H); 1.51-1.30 (m, 2 H); 1.38 (s, 9 H).

HPLC Analysis:
Ascentis Fused Core C18 column, 100×4.6 mm, 2.7 µm particle, 10% to 95% MeCN/0.1 wt % $H_3PO_4$ in 6 min, hold 2 min, post 2 min, 1.8 mL/min, UV 210 nm, 40° C., sample 2.0 µL, 10 min run. [Orn(Z) @1.87 min, NCA-Orn(Z) @3.40 min]

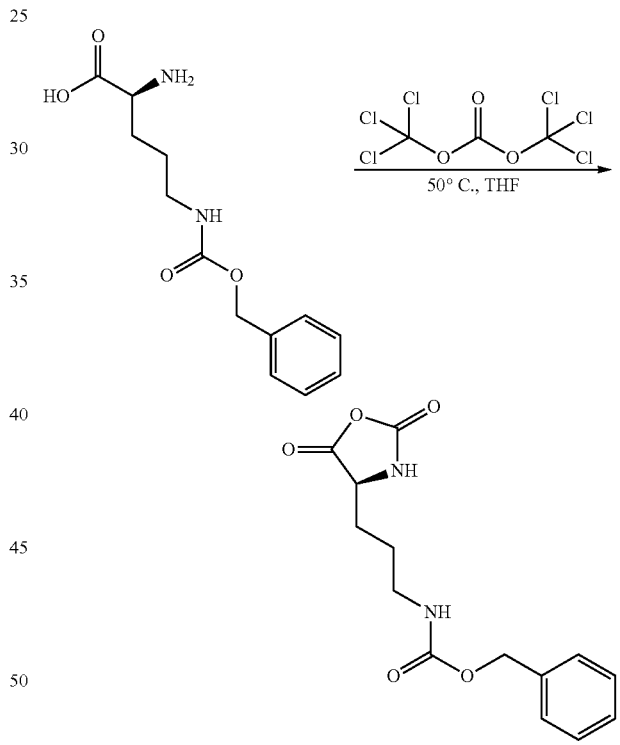

Deprotection of a Cbz-protected Polymer:
The protected polymer (8.90 g) was dissolved in 49 mL of dichloromethane (180 mg/mL polymer). HBr/HOAc (45 mL) was slowly added to the solution at room temperature. The solution was aged for 3 hours. The product was then precipitated by adding the solution into 600 mL of MTBE with vigorous stirring. The original reaction flask was rinsed with 50 mL of MeOH, aged for 0.5 h then the solvent was decanted. The solid left behind in the original reaction flask was slurried in 50 mL of MeOH for 0.5 h, then an additional 500 mL of methyl text-butyl ether (MTBE) was added to the original reaction flask, aged for an additional 0.5 h, filtered, and washed with an additional 500 mL of MTBE.

TABLE 7

Probing the effect of the hydrophobic amino acid monomer

| Initiator | Monomer 1 | Monomer 2 | Ratio of Monomers | Mn (g/mol) | Polymer Architecture | Masking Strategy | Polymer: siRNA (w/w) | siRNA Dose (mpk) | mRNA KD (%) |
|---|---|---|---|---|---|---|---|---|---|
| n-Bu | L-ORN | L-HOMOPHE | 3.2:1 | 23 | Block | 1:3 GalNAc:PEG | 5 | 1 | 88 |
| n-Bu | L-ORN | L-FLPHE | 5:1 | 15 | Block | 1:3 GalNAc:PEG | 5 | 1 | 85 |
| n-Bu | L-ORN | L-FLPHE | 3.5:1 | 15 | Block | 1:3 GalNAc:PEG | 5 | 1 | 88 |
| n-Bu | L-ORN | L-FLPHE | 5:1 | 15 | Block | 1:3 GalNAc:PEG | 5 | 1 | 86 |
| n-Bu | L-ORN | L-FLPHE | 3:1 | 15 | Block | 1:3 GalNAc:PEG | 5 | 1 | 87 |
| n-Bu | L-ORN | L-TYR | 1:1 | 15 | Statistical | 1:3 GalNAc:PEG | 5 | 1 | 0 |
| n-Bu | L-ORN | L-LEU | 5:1 | 11 | Block | 1:3 GalNAc:PEG | 5 | 1 | 92 |
| n-Bu | L-ORN | L-FLPHE | 3:1 | 15 | Block | 1:3 GalNAc:PEG | 2.5 | 1 | 44 |
| TEA | L-ORN | L-LEU | 8:1 | 79 | Block | 1:3 GalNAc:PEG | 2.5 | 1 | 68 |
| TEA | L-ORN | L-LEU | 5:1 | 46 | Statistical | 1:3 GalNAc:PEG | 2.5 | 1 | 83 |
| TEA | L-ORN | L-LEU | 9:1 | 46 | Statistical | 1:3 GalNAc:PEG | 2.5 | 1 | 79 |
| TEA | L-ORN | L-LEU | 19:1 | 63 | Statistical | 1:3 GalNAc:PEG | 2.5 | 1 | 75 |
| n-Bu | L-ORN | L-FLPHE | 4:1 | 12 | Block | 1:3 GalNAc:PEG | 5 | 1 | 93 |
| n-Bu | L-ORN | L-FLPHE | 4:1 | 12 | Block | 1:3 GalNAc:PEG | 2.5 | 1 | 53 |
| n-Bu | L-ORN | L-BIPHE | 20:1 | 11 | Block | 1:3 GalNAc:PEG | 5 | 1 | 3 |
| n-Bu | L-ORN | L-BIPHE | 10:1 | 12 | Block | 1:3 GalNAc:PEG | 5 | 1 | 11 |
| n-Bu | L-ORN | L-2-NAP | 4:1 | 12 | Block | 1:3 GalNAc:PEG | 5 | 1 | 57 |
| n-Bu | L-ORN | L-2-NAP | 7:1 | 8 | Block | 1:3 GalNAc:PEG | 5 | 1 | 35 |
| n-Bu | L-ORN | L-2-NAP | 10:1 | 8 | Block | 1:3 GalNAc:PEG | 5 | 1 | 41 |
| n-Bu | L-ORN | L-2-NAP | 3:1 | 10 | Block | 1:3 GalNAc:PEG | 5 | 1 | 39 |
| n-Bu | L-ORN | L-1-NAP | 15:1 | 10 | Block | 1:3 GalNAc:PEG | 5 | 1 | 0 |
| n-Bu | L-ORN | L-1-NAP | 7.5:1 | 11 | Block | 1:3 GalNAc:PEG | 5 | 1 | 49 |
| n-Bu | L-ORN | L-1-NAP | 5:1 | 12 | Block | 1:3 GalNAc:PEG | 5 | 1 | 43 |
| n-Bu | L-ORN | L-1-NAP | 3.5:1 | 13 | Block | 1:3 GalNAc:PEG | 5 | 1 | 34 |

End point = 48 hours
Species = Rat
siRNA = Sci10 ApoB

The following monomers were synthesized using the same general procedure as above (see monomer synthesis in the examples section):

| Starting Amino Acid | Name | Temp (° C.) | Solvent | Yield (%) |
|---|---|---|---|---|
| (structure) | L-Leucine | 50 | THF | 98 |
| (structure) | L-Homo-phenyl-alanine; (S)-alpha-Amino-benzene-butanoic acid | 50 | THF | 70 |
| (structure) | L-Fluoro-phenyl-alanine | 53 | THF | 82 |
| (structure) | L-4,4'-Biphenyl-alanine | 50 | THF | 38 |
| (structure) | L-2-Naphthyl-alanine | 52 | THF | 92 |
| (structure) | L-1-Naphthyl-alanine | 52 | THF | 85 |

L-homophenylalanine N-carboxyanhydride (NCA)

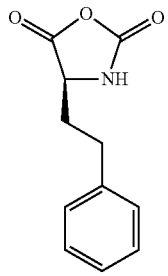 [SMILES: O=C1N[C@@H](CCc2ccccc2)C(=O)O1]

The slurry of L-Homophenylalanine (5 g, 27.5 mmol) in anhydrous THF (93 mL) was heated to 50° C. under $N_2$ atmosphere. Triphosgene (2.9 g, 0.35 eq, 9.76 mmol) was added as solid in one portion to the slurry at 50° C. The resulting mixture was heated at 50° C. under $N_2$. The reaction mixture became lemon yellow and clear in 1 h 10 min. The reaction mixture was cooled to ambient temperature. The majority of the THF was removed under reduced pressure to yield an orange oily residue (~10 mL). The residue was added dropwise to hexane (150 mL) under vigorous stirring. The formed precipitate was filtered and recrystallized a second time from 2-methyltetrahydrofuran:Hexanes=1:20 giving 4 g (70%) of the product as white solid. $^1$H NMR δ (ppm) (DMSO-$d_6$): 9.21 (1 H, s), 7.30 (2 H, t, J=7.42 Hz), 7.25-7.19 (3 H, m), 4.36 (1 H, t, J=6.24 Hz), 2.68 (2 H, t, J7.91 Hz), 2.07-1.93 (2 H, m).

L-Fluorophenylalanine N-carboxyanhydride (NCA)

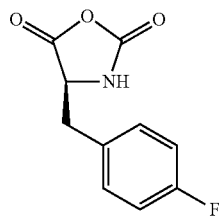 [SMILES: O=C1N[C@@H](Cc2ccc(F)cc2)C(=O)O1]

L-Fluorophenylalanine (5 g, 27.3 mmol) was added to a 250 mL oven-dried flask along with anhydrous THF (85 mL). Triphosgene (3.08 g, 0.38 eq, 10.37 mmol) was dissolved in anhydrous THF (10 mL) and the resulting solution was added to the amino acid solution through an addition funnel. The resulting mixture was heated up to 53° C. under $N_2$ for 1 h then cooled to room temperature. The left over solid was filtered, and the majority of the solvent was evaporated yielding a light orange oil. The oily residue was added dropwise to hexanes (250-300 mL) under vigorous stirring. The resulting mixture was stirred for 10 min, the precipitate was filtered, washed with hexanes, and dried under vacuum giving 4.7 g (82%) of L-Fluorophenylalanine NCA. $^1$H NMR δ (ppm) (DMSO-$d_6$): 9.07 (1 H, s), 7.22 (2 H, dd, J=8.40, 5.60 Hz), 7.16 (2 H, t, J=8.81 Hz), 4.77 (1 H, t, J=5.36 Hz), 3.03 (2 H, d, J=5.35 Hz).

L-4,4'-Biphenylalanine N-carboxyanhydride (NCA)

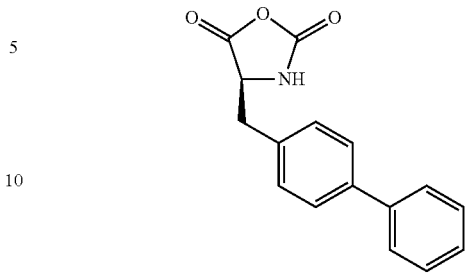

L-4,4'-biphenylalanine (2 g, 8.29 mmol) was charged in a dry 100 mL round bottom flask and anhydrous THF (23 mL) was added to the starting material. The resulting slurry was heated to 50° C. Triphosgene (0.935 g, 0.38 eq, 3.15 mmol) was dissolved in THF (4 mL) and the solution was added dropwise to the solution of amino acid at 46° C. under $N_2$. The resulting mixture was heating at 50° C. under $N_2$ for 1.5 h. The completion of the reaction was monitored by $^1$H NMR. Additional triphosgene (0.05 eq, 120 mg) was added, and the mixture was heated at 50° C. for another 45 min. The reaction mixture was cooled to room temperature and the orange fine slurry was flashed through silica gel packed into a glass funnel (silica gel was wetted with THF before use). The solvent was removed under reduced pressure giving an orange solid. The residue was dissolved in EtOAc (50 mL) and heated up to 60° C. The solution was filtered through celite and was added dropwise to hexanes (100 mL) under stirring. Newly formed white precipitate was filtered and dried on the pump for two days giving 840 mg (38%) of L-4,4'-biphenylalanine NCA. $^1$H NMR δ (ppm)(DMSO-$d_6$): 9.13 (1 H, s), 7.65 (4 H, dd, J=15.69, 7.72 Hz), 7.46 (2 H, t, J=7.51 Hz), 7.36 (1 H, t, J=7.33 Hz), 7.29 (2 H, d, J=7.79 Hz), 4.83 (1 H, t, J=5.29 Hz), 3.08 (2 H, d, J=5.30 Hz).

L-2-Naphthylalanine N-carboxyanhydride (NCA)

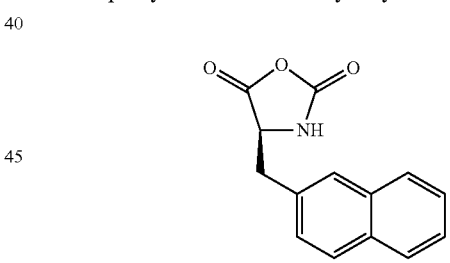

L-Naphthylalanine (3 g, 13.94 mmol) was added to anhydrous THF (40 mL) in a dry 100 mL round bottom flask and kept under $N_2$. The resulting slurry was heated to 50° C. Triphosgene (1.654 g, 0.4 eq, 5.57 mmol) was dissolved in THF (6 mL) in a vial and the resulting solution was added through a syringe to the slurry at 46 ° C. The resulting mixture was continued heating at 50-52 ° C. under $N_2$ for 2 hours, The completion of the reaction was monitored by $^1$H NMR. More triphosgene (75 mg) was added to the mixture and it was heated at 52° C. for additional 30 min. The light orange clear reaction mixture was cooled to room temperature and filtered through filter paper. THF was removed under reduced pressure. The orange oily residue was added dropwise to hexanes (100 mL) giving an oily solid. Hexane was decanted and the residue was dissolved in EtOAc (50 mL), heated up to 60° C., and filtered through celite. Filtered EtOAc solution was added to hexanes (100 mL) under stirring. The mixture with newly formed white precipitate was kept in a fridge for 30 min, the solid was filtered, washed with hexanes, and dried on the pump for two days giving 3.1 g (92%) of the L-Naphthylalanine NCA. ¹H NMR δ (ppm)(DMSO-d₆): 9.14 (1 H, s), 7.92-7.83 (3 H, m), 7.71 (1 H, s), 7.51 (2 t, J=4.54 Hz), 7.36 (1 H, d, J=8.43 Hz), 4.87 (1 H, t, J=5.49 Hz), 3.21 (2H, m).

L-1-Naphthylalanine N-carboxyanhydride (NCA)

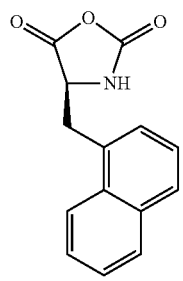 [SMILES: O=C1N[C@@H](Cc2cccc3ccccc23)C(=O)O1]

The L-1-Naphthylalanine NCA was synthesized from. L-1-Naphthylalanine (3 g, 13.94 mmol) and triphosgene (1.73 g, 0.42 eq, 5.83 mmol) in anhydrous THF (46.5 mL) at 52° C. for 2 h using the same procedure as described above for the synthesis of L-2-Naphthylalanine NCA. The sysnthesis gave 2.87 g (85%) of L-1-Naphthylalanine N-carboxyanhydride as white solid.

¹H NMR δ (ppm)(DMSO-d₆): 9.02 (1 H, s), 8.08 (1 H, d, J=8.26 Hz), 7.95 (1 H, d, J=7.93 Hz), 7.86 (1 H, d, J=8.10 Hz), 7.62-7.39 (4 H, m), 4.84 (1 H, t, J=6.25 Hz), 3.59 (1 H, dd, J=14.50, 5.41 Hz), 3.49 (1 H, dd, J=14.54, 7.16 Hz).

Synthesis of Butylamine Initiated Poly(ornithine-homophenylalanine) Block Copolymer

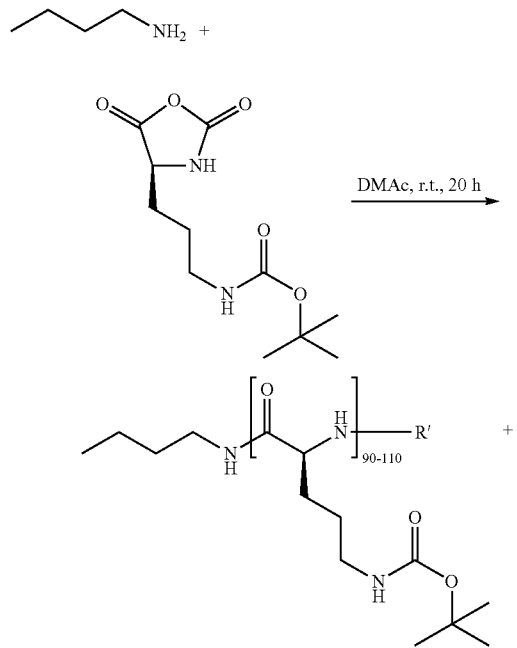

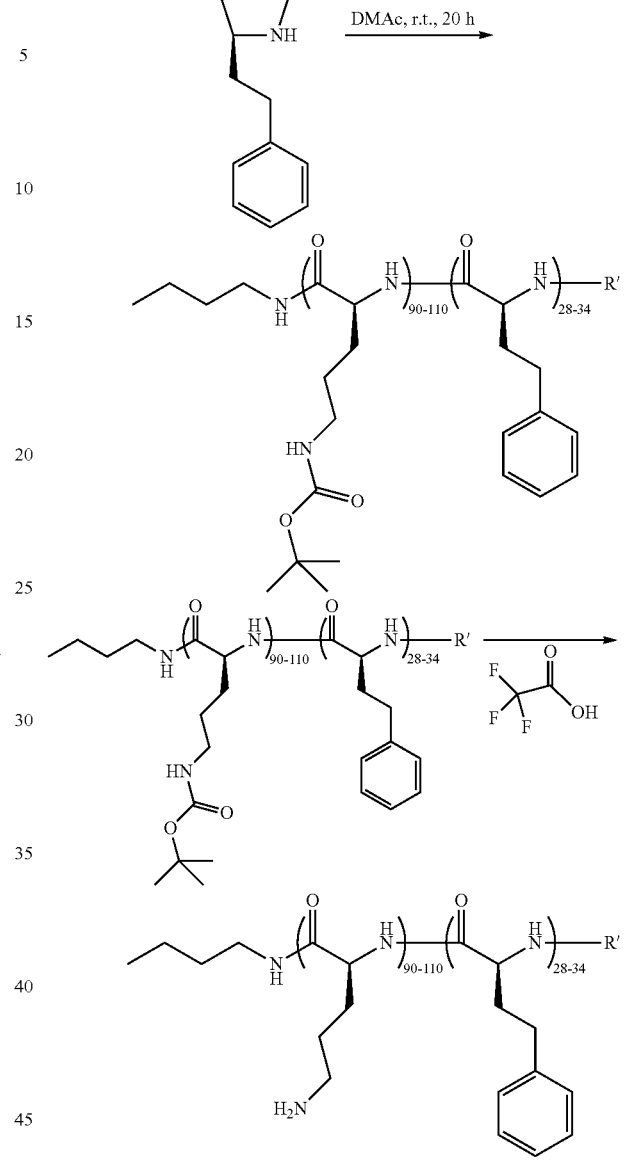

L-Boc-ornithine-N-carboxyanhydride (1.2 g, 4.65 mmol) was placed in a 100 mL round bottom flask and was purged with nitrogen. Next, anhydrous DMA (14.4 mL, 108 ug/ml of water) was added to the same flask. A solution of butylamine (0.5 mL) in DMA (13.5 mL) was prepared and 128.52 µL (0.093 mmol) was added to the solution of L-Boc-ornithine NCA and the mixture was stirred at room temperature for 5 min under N₂. The reaction mixture was then stirred under vacuum at room temperature for 20 h. The sample was collected for gel permeation chromatography, M$_n$=21,400 g/mol, PDI=1.12

L-Homophenylalanine NCA (282 mg, 1.37 mmol) was added to the reaction mixture in one portion, and the mixture was stirred under vacuum at room temperature for 15 h. GPC analysis gave a polymer with Mn=27 kDa ; PDI=1.16.

The reaction mixture was crashed into water (800 mL), stirred for 10-15 min, filtered, washed with additional water, and dried under vacuum over night giving a white solid (1.2 g) of the protected block copolymer.

75

Deprotection

Protected polymer (1.2 g) was deprotected in 100% TFA (7 mL) at an ice bath temperature for 1.5 h. The reaction mixture was crashed into t-butyl methyl ether (TBME) (150 mL). The ether was decanted, the residue was rinsed with TBME, and the left over ether was removed under reduced pressure. The deprotected polymer was dissolved in water (150 mL), the solution was frozen and dried by lyophilization for two days giving a white solid (1 g) of the final polymer. The purity of the polymer was determined by $^1$H NMR in the presence of an internal standard (trimethoxy benzene) and accounted for 66-70% by weight.

Synthesis of Butylamine Initiated Poly(ornithine) Fluorophenylalanine Block Copolymer

76

-continued

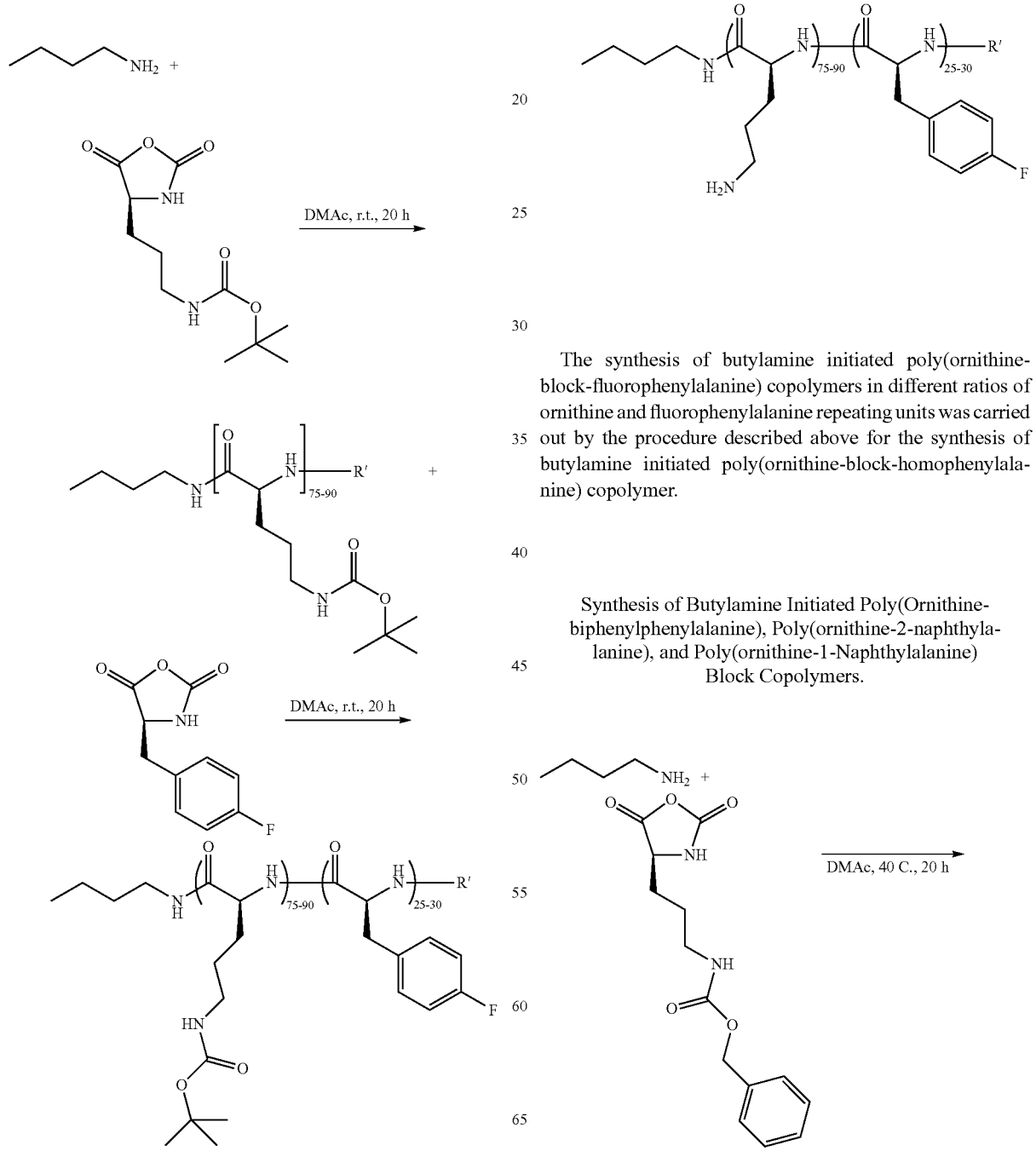

The synthesis of butylamine initiated poly(ornithine-block-fluorophenylalanine) copolymers in different ratios of ornithine and fluorophenylalanine repeating units was carried out by the procedure described above for the synthesis of butylamine initiated poly(ornithine-block-homophenylalanine) copolymer.

Synthesis of Butylamine Initiated Poly(Ornithine-biphenylphenylalanine), Poly(ornithine-2-naphthylalanine), and Poly(ornithine-1-Naphthylalanine) Block Copolymers.

77

-continued

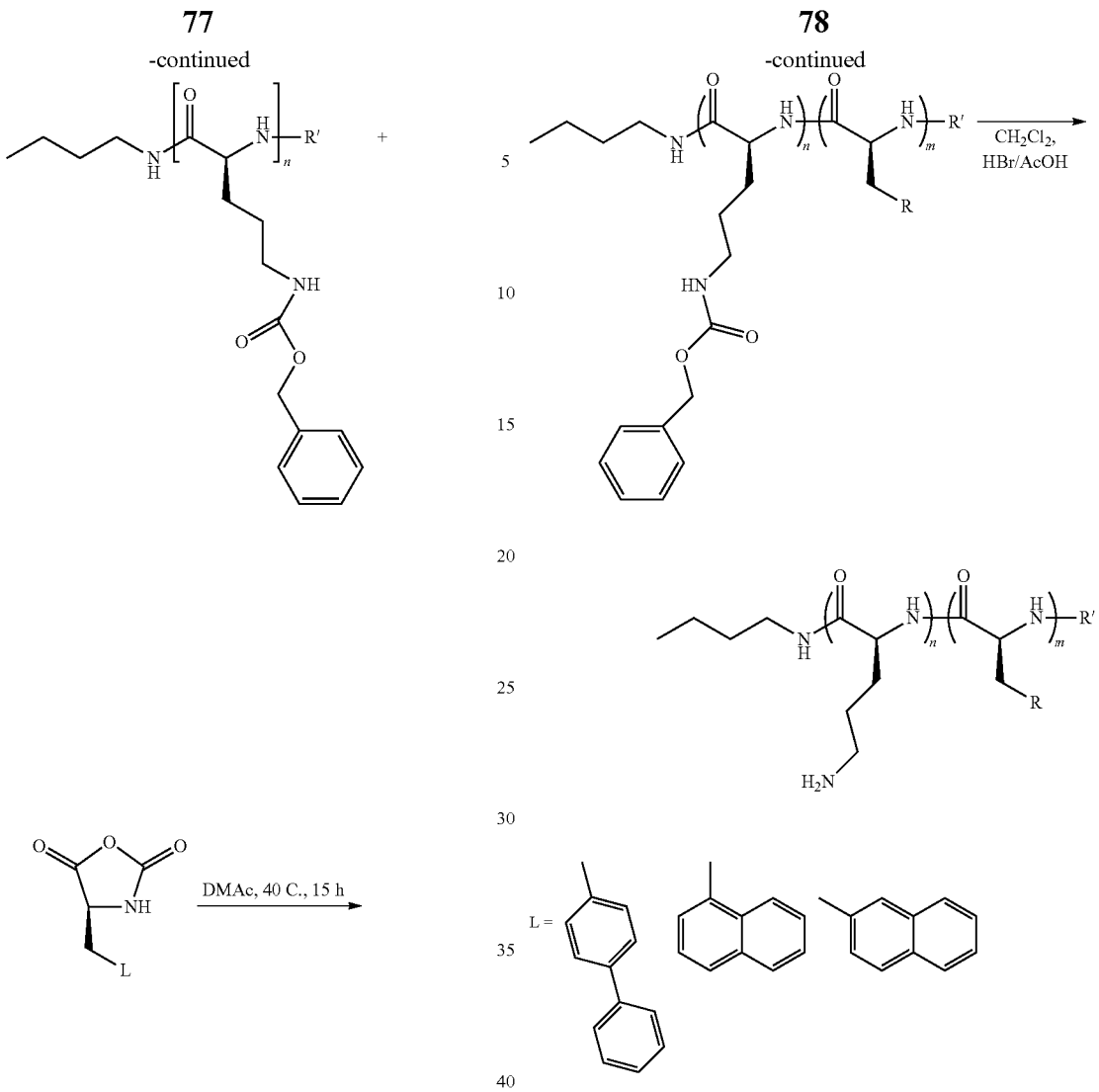

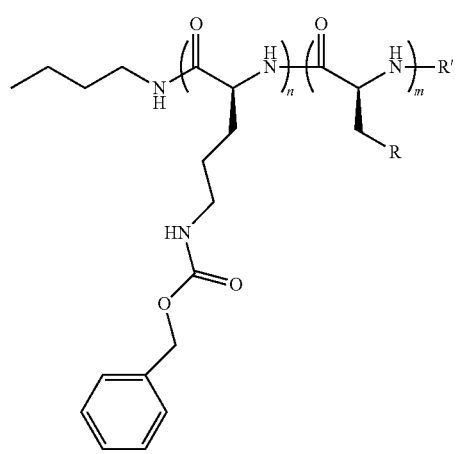

A solution of BuNH$_2$ (0.01-0.02 eq.) in DMA was added to the solution of L-Cbz-ornithine NCA (1 eq) in DMA (0.3 M) at room temperature. The resulting mixture was stirred under N$_2$ for 2 min, and then left to stir under vacuum at 40° C. for 15 hours. A sample (20 μL) was taken for GPC analysis. The second NCA (0.1 to 0.3 eq) was added to the reaction mixture in one portion, and the resulting mixture was heated at 40° C. under vacuum for another 10-15 hours. A sample (20 μL) was removed for GPC analysis. The reaction mixture was crashed into water (20-30×reaction volume), the white precipitate was filtered off, washed with water, and dried under vacuum.

Deprotection

CH$_2$Cl$_2$ (5.5×g of polymer) was added to the polymer at room temperature. HBr/AcOH (5×g of polymer) was added slowly to the methylene chloride solution at room temperature. The reaction mixture was left to age for two hours at room temperature, then precipitated into TBME (20-30×volume of the reaction). The residue was rinsed with MeOH and then precipitated into the same TBME mixture. The TBME was decanted, the residue was crashed into TBME, and solvent was decanted. This precipitation process was repeated again. The final polymer was dried under vacuum.

TABLE 8

Changing the structure of the polymer: mixing new monomers into first or second block of the PA polymer

| Initiator | Monomer 1 | Monomer 2 | Ratio of Monomers | Mn (g/mol) | Polymer Archit. | Masking Strategy | Polymer: siRNA (w/w) | siRNA Dose (mpk) | mRNA KD (%) |
|---|---|---|---|---|---|---|---|---|---|
| n-Bu | L-ORN | L-HIS | 3.8:1 | 15 | Block | 1:3 GalNAc:PEG | 5 | 1 | 11 |
| n-Bu | L-ORN | L-PHE/ L-ORN | 6:1 | 16 | Homo-b-statistical | 1:3 GalNAc:PEG | 5 | 1 | 52 |
| n-Bu | L-ORN | L-PHE/ L-ORN | 11:1 | 14 | Homo-b-statistical | 1:3 GalNAc:PEG | 5 | 1 | 40 |
| n-Bu | L-ORN | L-PHE/ L-ORN | 15:1 | 16 | Homo-b-statistical | 1:3 GalNAc:PEG | 5 | 1 | 42 |
| n-Bu | L-ORN/ L-GLU | L-PHE | [9:1]:[3.5] | 14 | Block | 1:3 GalNAc:PEG | 5 | 1 | 6 |
| n-Bu | L-ORN/ L-GLU | L-PHE | [5:1]:[1.5] | 14 | Block | 1:3 GalNAc:PEG | 5 | 1 | 0 |
| n-Bu | L-ORN | L-GLU/ L-PHE | 8:[1:2] | 18 | Block | 1:3 GalNAc:PEG | 5 | 1 | 75 |
| n-Bu | L-ORN | L-GLU/ L-PHE | 3.5:[1:1] | 18 | Block | 1:3 GalNAc:PEG | 5 | 1 | 82 |
| n-Bu | L-ORN, L-HIS | L-PHE | [76:11.5]:12.4 | 15 | Block | 1:3 GalNAc:PEG | 5 | 1 | 21 |
| n-Bu | L-ORN, L-HIS | L-PHE | [56:31.7]:12.4 | 12 | Block | 1:3 GalNAc:PEG | 5 | 1 | 1 |
| n-Bu | L-ORN | L-HIS, L-PHE | 64.3:[17.9:17.9] | 9 | Block | 1:3 GalNAc:PEG | 5 | 1 | 0.0 |

End point = 48 hours
Species = Rat
siRNA = Sci10 ApoB

The following monomer was synthesized using the same general procedure as above (see monomer synthesis in the examples section), with the exception of the following conditions [temperature, solvent]:

| Starting Amino Acid | Name | Temp (° C.) | Solvent | Yield (%) |
|---|---|---|---|---|
| 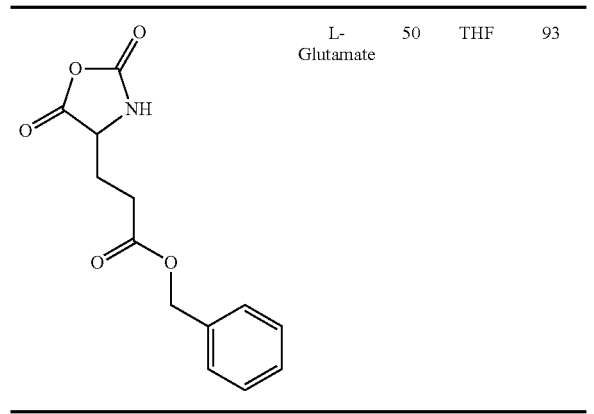 | L-Glutamate | 50 | THF | 93 |

Synthesis of Histidine NCA

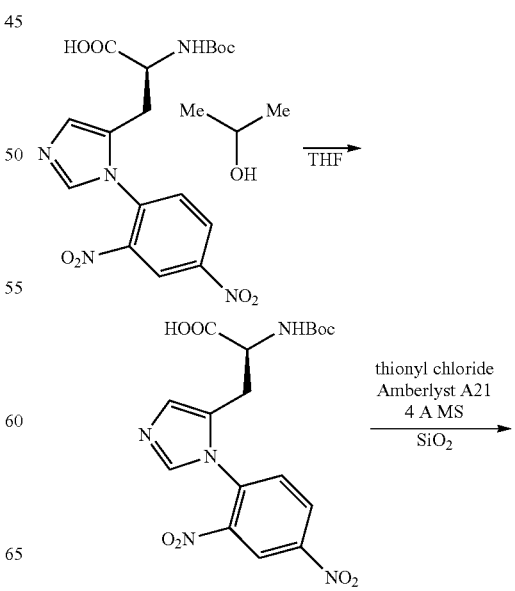

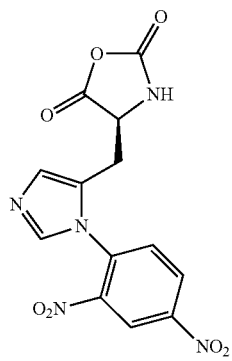

30 min. Next, Amberlyst resin was charged into the flask. Thionyl chloride was added over 1 hr via a syringe fitted with a polypropylene needle to prevent metal contamination. The internal temperature was maintained below 30° C. During the addition the mixture precipitated but the final resulting mixture was a homogeneous dark orange solution. HPLC was used to verify complete consumption of amino acid.

Upon complete reaction a 2 L glass-fitted funnel was loaded with a slurry of silica gel in THF and the layer of gel compacted and drained. The reaction mixture was filtered through the pad of silica gel to capture the sieves and resin. The filter cake was rinsed with THF. The filtrate solution was concentrated in vacuo to 5 L/kg level cf. product (361 mL total volume).

The concentrated THF slurry of NCA was transferred to a 5 L, 3-neck round-bottomed flask fitted with an overhead

| Reagent | MW | Stoic | amount | mmol | notes |
|---|---|---|---|---|---|
| His(DNP)-OH IPA | 481.57 | 1.0 eq | 100 g | 208 | |
| THF (desolvation) | | 4 × 10 L/kg | 4 × 1.00 L | | |
| His(DNP)-OH | 421.36 | 1.0 eq | 88 g | 208 | |
| THF (reaction) | | 10 L/kg | 880 mL | | |
| 4A molecular sieves | | 200 wt % | 176 g | | |
| Amberlyst A-21 resin | | 160 wt % | 141 g | | |
| Thionyl chloride | 118.97 | 1.10 eq | 27.24 g, 16.7 mL | 229 | d = 1.63 g/mL |
| Silica gel | | 100 wt % | 88 g | | |
| THF (rinse) | | 5 L/kg | 440 mL | | |
| MTBE | | 9.1 L/kg | 800 mL | | |
| Heptane | | 18.2 L/kg | 1.60 L | | |
| His(DNP) NCA | 347.24 | 1.0 eq | (72.23 g) | 208 | |

A 2 L, 1-neck round-bottomed flask was charged with amino acid solvate and was dissolved in dry THF. The resulting homogeneous solution was concentrated in vacuo until it precipitated and three additional portions of THF were charged to the flask to dissolve the amino acid and were then concentrated to dryness. The desolvated compound was dried overnight under high vacuum resulting in a dried orange foam. $^1$H NMR analysis showed complete removal of the IPA from the material. Recovery was 98%.

A 3 L, 3-neck round-bottomed flask was fitted with an overhead stirrer, internal thermocouple probe, and nitrogen inlet. This flask was charged with amino acid and dissolved in dry THF where upon molecular sieves were added. Stirred for stirrer, nitrogen inlet, and addition funnel. Solvent level was adjusted to account for any needed rinsing. To the stirred slurry was added MTBE. After 5 min, heptane was added over 20 min. The desired product was isolated by filtration, rinsing with a small amount of 2:1 heptane:MTBE. The orange solid product was dried in the vacuum oven overnight at 25° C. and vacuum better than 25 inHg with nitrogen sweep.

Isolated: 72 g, 66% @ 98.40 wt % (NMR) purity of an orange-brown powder.

Synthesis of Histidine-Containing Polymer (Specifically: Orn, His Statistical Block Followed by Phe Block)

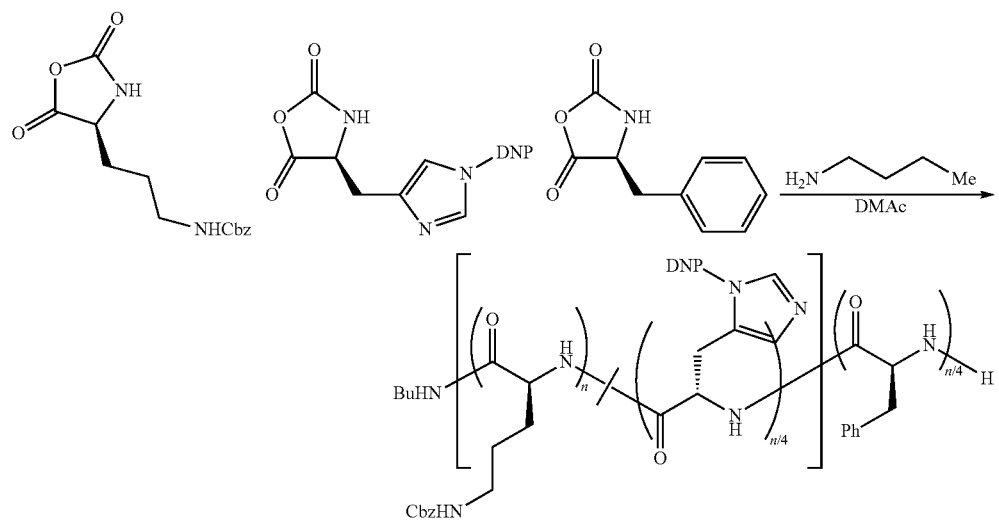

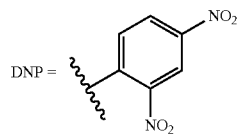

| Reagent | MW | Stoic | amount | mmol | notes |
|---|---|---|---|---|---|
| Orn(Boc) NCA | 292.29 | 1.0 eq | 200 mg | 0.684 | |
| DMAc (Orn) | | 5 mL/g | 1.00 mL | | |
| His(DNP) NCA | 347.24 | 0.25 eq | 59.4 mg | 0.171 | |
| DMAc (His) | | 3.9 mL/g cf. His | 0.23 mL | | |
| Butylamine | 73.14 | 2 mol % | 0.256 mL | 0.014 | 0.05338M in DMAc |
| Phe NCA | 191.18 | 0.25 eq | 32.7 mg | 0.171 | |
| DMAc (Phe) | | 7 mL/g cf. Phe | 0.23 mL | | |
| Water | | 65 mL/g cf. Orn | 13 mL | | |
| Isolated terpolymer | 18 kDa | 1.0 eq | (252 mg) | 0.014 | |

A 40 mL glass vial with septum cap and magnetic stir bar was charged with ornithine NCA and histidine NCA and was dissolved in DMA. A stock solution of butylamine in DMA was made and the appropriate amount of this was added to the reaction vial. The vial was capped and put under $10^{-6}$ mmHg vacuum while heating to 70° C. overnight. Gas evolution was often difficult to observe on small scale. Next, a solution of phenylalanine NCA was added to the reaction mixture which was then capped and subjected to 70° C. and $<10^{-6}$ mmHg overnight.

Isolation may be accomplished by pouring the reaction mixture into 13 mL of rapidly stirred water. The resulting slurry was spun in the centrifuge to pelletize the solid polymer after which the liquors were decanted and the wet polymer dried in vacuo.

-continued

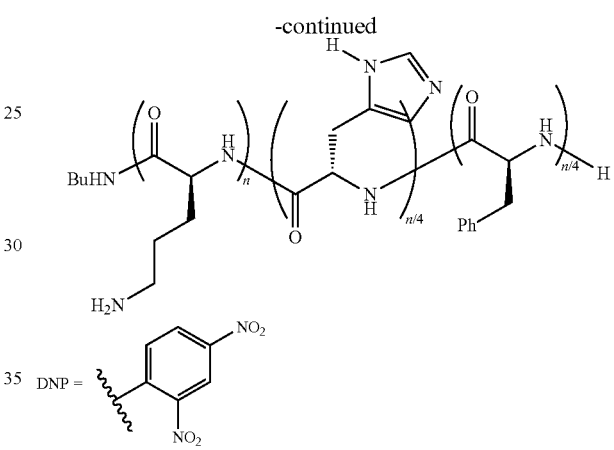

| Reagent | MW | Stoic | amount | mmol | notes |
|---|---|---|---|---|---|
| Polymer | 18 kDa | 1.0 eq | 250 mg | 0.014 | — |
| DMF | — | 16 mL/g | 4.0 mL | — | — |
| 2-Mercaptoethanol | 78.13 | 1000 eq | 1.094 g, | 14.0 | d = 1.114 g/mL |
| DCM | — | 10 mL/g | 2.50 mL | — | — |
| 33% HBr in HOAc | 80.91 | 1000 eq | 3.96 mL | 14.0 | d = 1.49 g/mL |
| MTBE | — | 20 mL/g | 5.0 mL | — | — |
| MeOH | — | 2 mL/g | 0.50 mL | — | — |
| Deprotected polymer | 9 kDa | 1.0 eq | (129 mg) | 0.014 | — |

Deprotection of Histidine-Containing Polymers

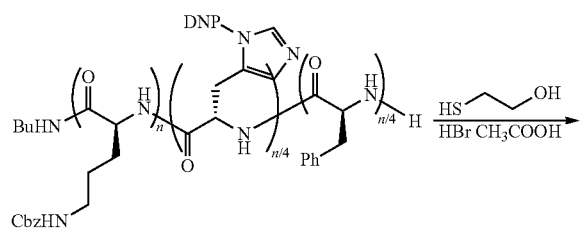

Polymer was dissolved in DMF and charged to a 40 mL glass vial with a septum cap and magnetic stir bar. Added mercaptoethanol and stirred at 25° C. in the capped vial overnight. Removed the solvents in vacuo. The DNP-deprotected polymer was dissolved in DCM and HBr in HOAc was added in one portion and the resulting mixture was stirred at 25° C. overnight under nitrogen.

Isolation and purification methods were often determined by the feed ratio with differing polymers behaving significantly differently. The original procedure was to pour the slurry into rapidly stirred MTBE and MeOH with pelletizing and decanting. An alternative method was to simply evaporate the entire volume of the reaction. This latter method required the use of HBr-compatible equipment and proper exhaust ventilation. Should those techniques fail to work, dialysis using commercially available membrane tubing with appropriately-sized pores (here, 3.5 kDa) was used. The polymer was first dissolved in a mixture of DMSO and 0.5 M TFA and it was then dialyzed against 1:1 DMSO:0.5 M TFA overnight with gentle stirring in the bath. The bath was decanted and was refilled with either 0.5 M TFA alone or 1:1 with DMSO and was stirred again overnight. The resulting polymer could precipitate in the dialysis bag but was always homogeneous at the start. The polymer was then isolated by decanting from the dialysis bag and concentrating in vacuo.

Actual incorporation ratio of monomers was determined by $^1$H NMR. Weight percents of polymer were determined by adding 4-trifluoromethyl-3-nicotinic acid as an internal standard in the NMR sample.

All monomers depicted in this table were described elsewhere (see examples section for L-ORN NCA, L-PHE NCA, and see Table 7 for the L-LEU NCA and Table 8 for the L-GLU NCA as well as the L-HIS NCA). The polymerization chemistry followed the general procedure outlined in the polymer synthesis section of the examples section.

Monomer Synthesis

Boc-L-arginine(Z)2-N-carboxyanhydride (NCA):

To a slurry of boc-L-arginine(Z)2-OH (500 mg, 0.92 mmol) in 20 mL of anhydrous ethyl acetate under nitrogen was charged a solution of triphosgene (109 mg, 0.37 mmol) in 2 mL of ethyl acetate followed by triethylamine (0.14 mL, 1.01 mmol). The reaction was stirred at room temperature for 30 minutes. The remaining solid was removed by filtration, washing with 10 mL of ethyl acetate. The filtrate was concentrated and the residue purified by silica gel chromatography (eluent, 50% 400% ethyl acetate in hexanes) to give 195

TABLE 9

Probing the effect of polymer molecular weight

| Initiator | Monomer 1 | Monomer 2 | Ratio of Monomers | Mn (g/mol) | Polymer Architecture | Masking Strategy | Polymer: siRNA (w/w) | siRNA Dose (mpk) | mRNA KD (%) |
|---|---|---|---|---|---|---|---|---|---|
| n-Bu | L-ORN | L-PHE | 4:1 | 12 | Statistical | 1:3 GalNAc:PEG | 5 | 1 | 3 |
| n-Bu | L-ORN | L-PHE | 4:1 | 17 | Statistical | 1:3 GalNAc:PEG | 5 | 1 | 26 |
| n-Bu | L-ORN | L-PHE | 4:1 | 25 | Statistical | 1:3 GalNAc:PEG | 5 | 1 | 65 |
| n-Bu | L-ORN | L-PHE | 4:1 | 39 | Statistical | 1:3 GalNAc:PEG | 5 | 1 | 68 |

End point = 48 hours

Species = Rat siRNA = Sci10 ApoB

All monomer syntheses, polymerization chemistry, and conjugation chemistry followed the procedures described in the examples section.

mg (45% yield) of product as a waxy solid. $^1$H NMR (500 MHz, DMSO-d$_6$): δ 7.43-7.28 (m, 10H), 5.24 (s, 2H), 5.06 (s, 2H), 4.45 (t, J=7.05 Hz, 1H), 3.87 (m, 2H), 1.75-1.35 (m, 4H).

TABLE 10

Examining the effect of polymer architecture

| Initiator | Monomer 1 | Monomer 2 | Monomer 3 | Ratio of Monomers | Mn (g/mol) | Polymer Archit. | Masking Strategy | Polymer: siRNA (w/w) | siRNA Dose (mpk) | mRNA KD (%) |
|---|---|---|---|---|---|---|---|---|---|---|
| n-Bu | L-ORN | L-LEU | L-ORN | 3:1:3 | 16 | Triblock | 1:3 GalNAc:PEG | 5.0 | 0.25 | 45 |
| n-Bu | L-ORN | L-LEU | L-ORN | 3:1:3 | 16 | Triblock | 1:3 GalNAc:PEG | 5.0 | 0.5 | 64 |
| n-Bu | L-ORN | L-PHE | L-ARG | 10:2:1 | 13 | Triblock | 1:3 GalNAc:PEG | 5 | 1 | 79 |
| n-Bu | L-ORN | L-GLU | L-PHE | 10:1:3 | 18 | Triblock | 1:3 GalNAc:PEG | 5 | 1 | 98 |
| n-Bu | L-ORN | L-HIS | L-PHE | 62.7:16.4:2 0.9 | 9 | Triblock | 1:3 GalNAc:PEG | 5 | 1 | 0 |
| n-Bu | L-ORN | L-PHE | L-HIS | 65.8:19.5:1 4.6 | 9 | Triblock | 1:3 GalNAc:PEG | 5 | 1 | 10 |

End point = 48 hours

Species = Rat siRNA = Sci10 ApoB

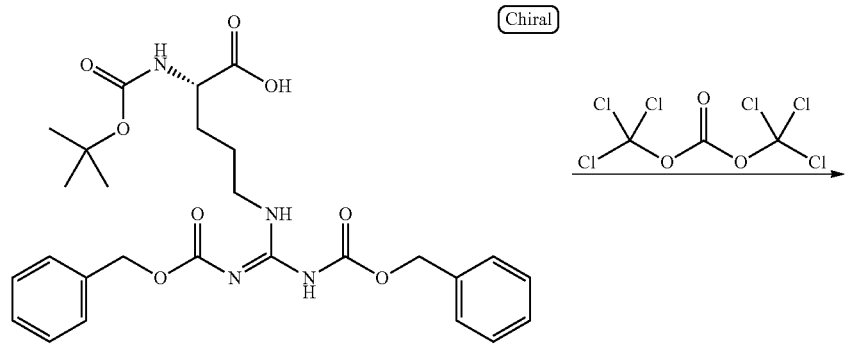

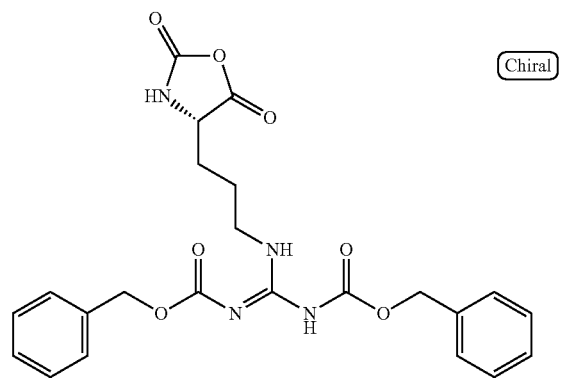

Deprotection (for Polymers Containing Glu or Arg):

The protected polymer was taken up in 33% HBr in acetic acid (100 mg/mL polymer) and the mixture was heated to 50° C. for 90 minutes. The reaction mixture was cooled to room temperature, precipitated in MTBE then filtered to yield the deprotected polymer.

TABLE 11

| | | | | | | Changing the disulfide connection from the siRNA to the polymer side chain | | | | |
|---|---|---|---|---|---|---|---|---|---|---|
| Initiator | Monomer 1 | Monomer 2 | Ratio of Monomers | Mn (g/mol) | Polymer Archit. | Polyconjugate to siRNA bond | Masking Strategy | Polymer: siRNA (w/w) | siRNA Dose (mpk) | mRNA KD (%) |
| n-Bu | L-ORN | L-PHE | 5:1 | 11 | Block | SMPT | 1:3 GalNAc:PEG | 5.0 | 1.0 | 78 |
| n-Bu | L-ORN | L-PHE | 5:1 | 11 | Block | SPDP | 1:3 GalNAc:PEG | 5.0 | 1.0 | 77 |
| n-Bu | L-ORN | L-PHE | 4:1 | 12 | Block | Methyl-CDM linked Sci10 ApoB | 1:3 GalNAc:PEG | 5.0 | 1.0 | 83 |

TABLE 11-continued

Changing the disulfide connection from the siRNA to the polymer side chain

| Initiator | Monomer 1 | Monomer 2 | Ratio of Monomers | Mn (g/mol) | Polymer Archit. | Polyconjugate to siRNA bond | Masking Strategy | Polymer: siRNA (w/w) | siRNA Dose (mpk) | mRNA KD (%) |
|---|---|---|---|---|---|---|---|---|---|---|
| n-Bu | L-ORN | L-PHE | 4:1 | 12 | Block | Ethoxy-CDM linked Sci10 ApoB | 1:3 GalNAc:PEG | 5.0 | 1.0 | 81 |

End point = 48 hours
Species = Rat
siRNA = Sci10 ApoB

The chemistry required for the monomer syntheses, and polymer syntheses followed the general procedure outlined in the examples section. The conjugation chemistry was modified to include an alternative linkage from the siRNA to the polymer backbone.

Table 11, entries 1-2;
Modification of Polymer Conjugation Procedure:
Step 1: Activation of polymer: A polymer sample (203 mg) in DMSO (5 mL) was heated to 50 ° C. for 15 min with stirring. After cooling to RT, a solution of SPDP in DMSO (1 mg/100 uL) was added (816 uL, 5.4 eq relative to RNA) and the reaction was stirred at RT until dilution with buffer and SATA-RNA addition.

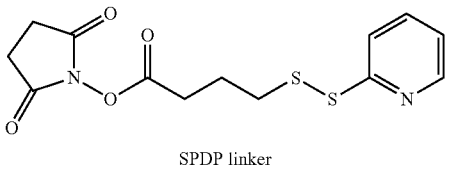 [SMILES: O=C(CCCSSc1ccccn1)ON1C(=O)CCC1=O]

SPDP linker

Table 11, entries 3-4;
Passenger Strand TEAA Salt
The oligonucleotide passenger strand (75 mg) was taken up in 200 mM TEAA buffer (15 mL) and subjected to centrifugal dialysis (3 kDa cut-off membrane). The process was repeated two times with TEAA buffer, then three times with water. The resulting solution was concentrated, frozen, and lyophilized overnight to yield product as a white fluffy solid.

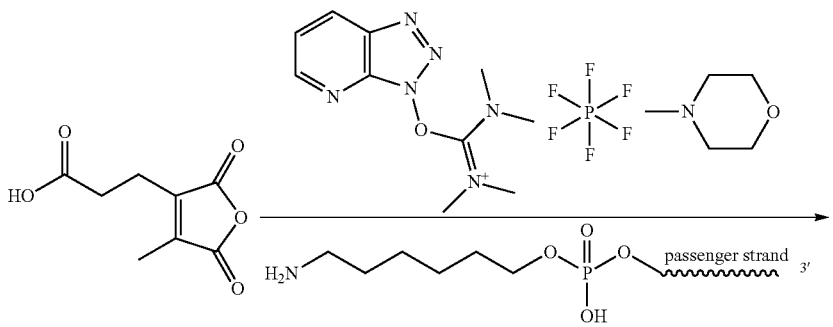

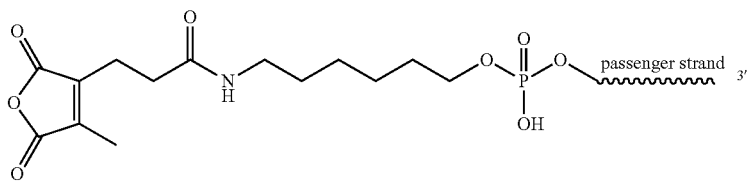

CDM Linked Passenger Strand
The carboxy dimethylmaleic anhydride (CDM) acid (27 µmol) was dissolved in DMSO (250 µL). HATU (41 µmol) and N-methylmorpholine (82 µmol) were added and the mixture was vortexed, then allowed stand at room temperature for 15 minutes. The mixture was then added to a solution of the oligonucleotide passenger strand TEAA salt (6.9 µmol) in DMSO (1 mL). The mixture was vortexed, then allowed to stand at RT for 30 minutes. The reaction mixture was diluted with 0.05% TFA (13 mL) and subjected to centrifugal dialysis (3 kDa cut-off membrane). This process was repeated two times. The resulting solution was concentrated, frozen, and lyophilized overnight to yield product as a white fluffy solid. LC/MS confirms product.

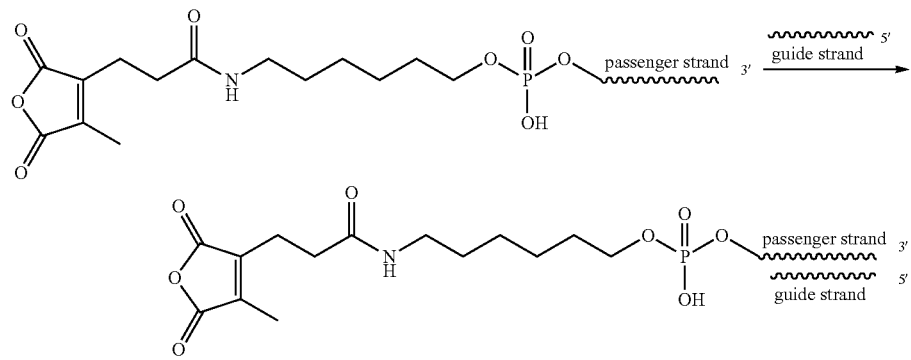

Duplex Formation

Equal masses of the CDM linked passenger strand and the corresponding guide strand were dissolved in DMSO (20 total mg/mL) and heated to 90° for one minute. The reaction mixture was cooled and diluted with 0.05% TFA (15 mL) and subjected to spin dialysis (3 K membrane) three times. The resulting concentrated solution (~1.5 mL) was lyophilized overnight to yield product as a white fluffy solid. LC/MS confirms product.

TABLE 12

Investigating the effect of molecular weight and ORN:PHE ratio

| Initiator | Monomer 1 | Monomer 2 | Ratio of Monomers | Mn (g/mol) | Polymer Architecture | Masking Strategy | Polymer: siRNA (w/w) | siRNA Dose (mpk) | mRNA KD (%) |
|---|---|---|---|---|---|---|---|---|---|
| n-Be | L-ORN | L-PHE | 2.6:1 | 12 | Block | 1:3 GalNAc:PEG | 2.5 | 1 | 14 |
| n-Bu | L-ORN | L-PHE | 4:1 | 12 | Block | 1:3 GalNAc:PEG | 2.5 | 1 | 56 |
| n-Bu | L-ORN | L-PHE | 7.3:1 | 12 | Block | 1:3 GalNAc:PEG | 2.5 | 1 | 7 |
| n-Bu | L-ORN | L-PHE | 9.2:1 | 12 | Block | 1:3 GalNAc:PEG | 2.5 | 1 | 36 |
| n-Bu | L-ORN | L-PHE | 1.5:1 | 14 | Block | 1:3 GalNAc:PEG | 2.5 | 1 | 8 |
| n-Be | L-ORN | L-PHE | 1.9:1 | 14 | Block | 1:3 GalNAc:PEG | 2.5 | 1 | 29 |
| n-Bu | L-ORN | L-PHE | 5.5:1 | 17 | Block | 1:3 GalNAc:PEG | 2.5 | 1 | 74 |
| n-Bu | L-ORN | L-PHE | 7.5:1 | 17 | Block | 1:3 GalNAc:PEG | 2.5 | 1 | 39 |
| n-Bu | L-ORN | L-PHE | 4.2:1 | 20 | Block | 1:3 GalNAc:PEG | 2.5 | 1 | 47 |
| n-Bu | L-ORN | L-PHE | 8.9:1 | 19 | Block | 1:3 GalNAc:PEG | 2.5 | 1 | 15 |
| n-Bu | L-ORN | L-PHE | 2.8:1 | 26 | Block | 1:3 GalNAc:PEG | 2.5 | 1 | 54 |
| n-Be | L-ORN | L-PHE | 4.0:1 | 27 | Block | 1:3 GalNAc:PEG | 2.5 | 1 | 56 |
| n-Bu | L-ORN | L-PHE | 4.4:1 | 25 | Block | 1:3 GalNAc:PEG | 2.5 | 1 | 53 |
| n-Bu | L-ORN | L-PHE | 2.5:1 | 24 | Block | 1:3 GalNAc:PEG | 2.5 | 1 | 49 |
| n-Bu | L-ORN | L-PHE | 3.1:1 | 29 | Block | 1:3 GalNAc:PEG | 2.5 | 1 | 45 |
| n-Bu | L-ORN | L-PHE | 10.3:1 | 29 | Block | 1:3 GalNAc:PEG | 2.5 | 1 | 43 |

TABLE 12-continued

Investigating the effect of molecular weight and ORN:PHE ratio

| Initiator | Monomer 1 | Monomer 2 | Ratio of Monomers | Mn (g/mol) | Polymer Architecture | Masking Strategy | Polymer: siRNA (w/w) | siRNA Dose (mpk) | mRNA KD (%) |
|---|---|---|---|---|---|---|---|---|---|
| n-Bu | L-ORN | L-PHE | 4.8:1 | 45 | Block | 1:3 GalNAc:PEG | 2.5 | 1 | 74 |
| n-Bu | L-ORN | L-PHE | 2.5:1 | 43 | Block | 1:3 GalNAc:PEG | 2.5 | 1 | 72 |
| n-Bu | L-ORN | L-PHE | 9.6:1 | 38 | Block | 1:3 GalNAc:PEG | 2.5 | 1 | 55 |
| n-Bu | L-ORN | L-PHE | 24.0:1 | 38 | Block | 1:3 GalNAc:PEG | 2.5 | 1 | 72 |

End point = 48 hours
Species = Rat
siRNA = Sci10 ApoB

All monomer syntheses, polymer syntheses and conjugation chemistry followed the same general procedure as outlined in the examples section.

TABLE 13

Modifying a certain percent of the amine side chains

| Initiator | Monomer 1 | Monomer 2 | Ratio of Monomers | Mn (g/mol) | Polymer Architecture | Masking Strategy | Polymer: siRNA (w/w) | siRNA Dose (mpk) | mRNA KD (%) |
|---|---|---|---|---|---|---|---|---|---|
| n-Bu | L-ORN with 18.1% 1m2i | L-PHE | 4:1 | 12 | Block | 1:3 GalNAc:PEG | 5 | 1 | 76 |
| n-Bu | L-ORN with 27.3% 1m2i | L-PHE | 4:1 | 12 | Block | 1:3 GalNAc:PEG | 5 | 1 | 79 |

End point = 48 hours
Species = Rat
siRNA = Sci10 ApoB

Monomer synthesis, polymer synthesis, as well as the conjugation chemistry followed the detailed procedure described in the examples section, with the exception of a post-polymerization modification (described below).

Polymer Modification

Modification of Amine Side Chains with 1-Methyl-2-Imidazolecarboxaldehyde

4:1 L-Ornithine:L-phenylalanine deprotected block copolymer (Mn=10,500; PDI=1.1; TFA salt; 2.237 g polymer; 56 weight percent) was added to a glass jar with screw cap lid equipped with a stir bar. Anhydrous methanol (37.5 mL, water ppm=100) was added and the solution was heated to 50° C. with stirring for 30 minutes to dissolve solid polymer. The solution was removed from heating and triethylamine (1.8 mL) was added followed by a solution of 1-methyl-2-imidazolecarboxaldehyde (1.8 mL solution; 0.1 mg/uL solution in methanol, 181.5 mg aldehyde). The reaction mixture was heated to 50° C. with stirring for 2 hours. The reaction mixture was removed from heat and sodium borohydride was added to the reaction as a solid (417.6 mg). The reaction mixture was stirred at room temperature for 1 hour. The reaction mixture was diluted with a 1:1 v:v mixture of water:methanol (40 mL) and transferred to regenerated cellulous dialysis tubing (Spectrum Laboratories, spectra/por 1, nominal MWCO=6-8 kD) and dialyzed against 1:1 v:v water:methanol (3 L each cycle, 2 cycles) followed by dialysis against 0.5 M aqueous TFA solution (3 L each cycle, 1 cycle), followed by water (3 L each cycle, 1 cycle) for a minimum of 12 hours of equilibration per dialysis cycle. The polymer retentate solution was removed from the dialysis tubing, placed in plastic falcon tubing, frozen and lyophilized overnight to afford white solid polymer (2.4 grams; 61.8 weight percent). Proton NMR analysis showed that 18.1% of the ornithine amines were modified with 1-methyl-2-imidazole.

A similar procedure was followed for the polymer with 27.3% modification with 1-methyl-2-imidazolecarboxaldehyde.

TABLE 14

Examining the effect of PEG length

| Initiator | Monomer 1 | Monomer 2 | Ratio of Monomers | Mn (g/mol) | Polymer Architecture | Polyconjugate to siRNA bond | Masking Strategy | Polymer: siRNA (w/w) | siRNA Dose (mpk) | mRNA KD (%) |
|---|---|---|---|---|---|---|---|---|---|---|
| n-Bu | L-ORN | L-PHE | 5.3:1 | 11 | Block | disulfide | 1:3 GalNAc:PEG 0.5 kDa | 5 | 0.5 | 66 |

TABLE 14-continued

Examining the effect of PEG length

| Initiator | Monomer 1 | Monomer 2 | Ratio of Monomers | Mn (g/mol) | Polymer Architecture | Polyconjugate to siRNA bond | Masking Strategy | Polymer:siRNA (w/w) | siRNA Dose (mpk) | mRNA KD (%) |
|---|---|---|---|---|---|---|---|---|---|---|
| n-Bu | L-ORN | L-PHE | 5.3:1 | 11 | Block | disulfide | 1:3 GalNAc:PEG 2 kDa | 5 | 0.5 | 68 |

End point = 48 hours
Species = Rat
siRNA = Sci10 ApoB

All monomer syntheses, polymerization chemistry, and conjugation chemistry followed the procedures described in the examples section with the exception of the CDM-PEG masking step where two different PEG lengths were used. The general protocol uses a CDM-PEG 0.5 kDa. The synthesis of the CDM-PEG 2 kDa was described before.

posed of 100mM Tris with 2M NaCl, pH 8.4. Total RNA (both free and bound) was determined by using Inductively Coupled Plasma (ICP) spectroscopy. Since the RNA is the only phosphorus containing species in the formulations, determining the total phosphorus content can be used to directly determine the total RNA concentration. Once the free

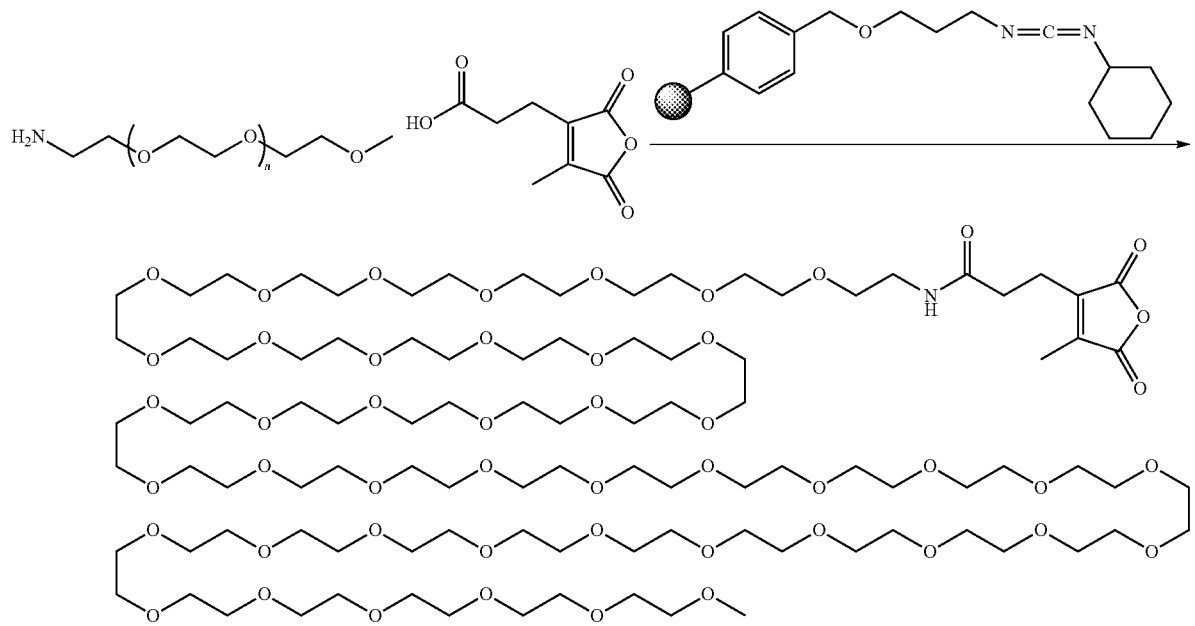

CDM-PEG 2 kDa Amide

The carboxy dimethylmaleic anhydride (CDM) acid (2.7 mmol) was dissolved in dichloromethane (27 mL). PS-Carbodiimide resin (5.4 mmol) was added and the mixture was shaken at room temperature for 30 minutes. A solution of 2K mPEG amine (2.7 mmol) in dichloromethane (8 mL) was added and the reaction was shaken at room temperature overnight. The mixture was filtered and the resin washed with dichloromethane. The filtrate was concentrated and the residue purified by reverse phase prep HPLC (95:5 to 20:80-water:ACN, each with 0.1% TFA) to give 4.2 g of product (71%). $^1$H NMR (500 MHz, CDCl$_3$): δ 3.86-3.36 (m, 183H), 2.79 (t, J=7.1 Hz, 2H), 2.55 (t, J=7.1 Hz, 2H), 2.12 (s, 3H).

Example 1 siRNA Conjugation Efficiency:

Free RNA duplex as well as free RNA duplex-dimer was determined by aqueous SEC using a GE Heathsciences Superdex 75HR 10/300 column. The mobile phase was com- RNA (duplex and duplex-dimer) and total RNA is determined, the amount of RNA conjugated to the polymer can be calculated (i.e. conjugation efficiency).

Figures 10A, 10B:
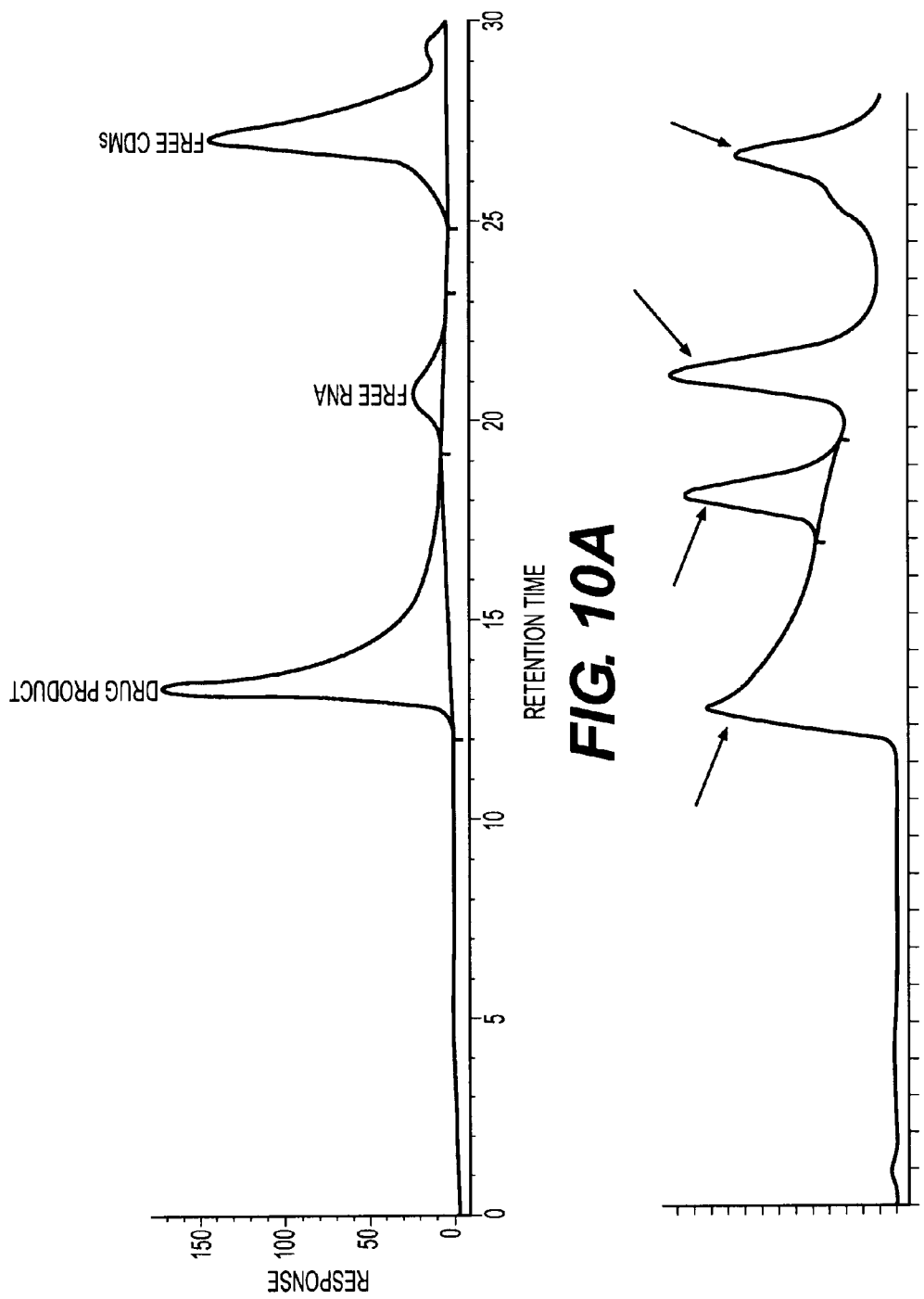
FIG. 10A. An example of a SEC chromatogram of a masked polymer conjugate.
FIG. 10B. An example of a SEC chromatogram of a masked polymer conjugate with a siRNA dimer present.

Example SEC chromatogram of a masked polymer conjugate is shown in FIG. 10A.

Example SEC chromatogram of a masked polymer conjugate with siRNA dimer present is shown in FIG. 10B.

Masking Efficiency:

Total concentrations of CDM-GALNAC and CDM-PEG were determined using reverse-phase HPLC with mobile phases of 0.1% TFA in water and 0.1% TFA in 70/30 methanol:acetonitrile. Rapid demasking of the polymer after injection onto the column allows quantitation of CDMs with the polymer removed using a C 18 guard column to prevent chromatographic interference. Free (i.e. unbound) CDM-GALNAC and CDM-PEG is analyzed by first filtering through a 10K centrifuge filter followed by analysis using the same reverse-phase HPLC method. Masking Efficiency can be calculated by first calculating the bound RNA, CDM-GALNAC and CDM-PEG. The polymer molecular weight in combination with the total amines available for conjugation is then used with the bound ligands to calculate masking efficiency.

Figure 10C:
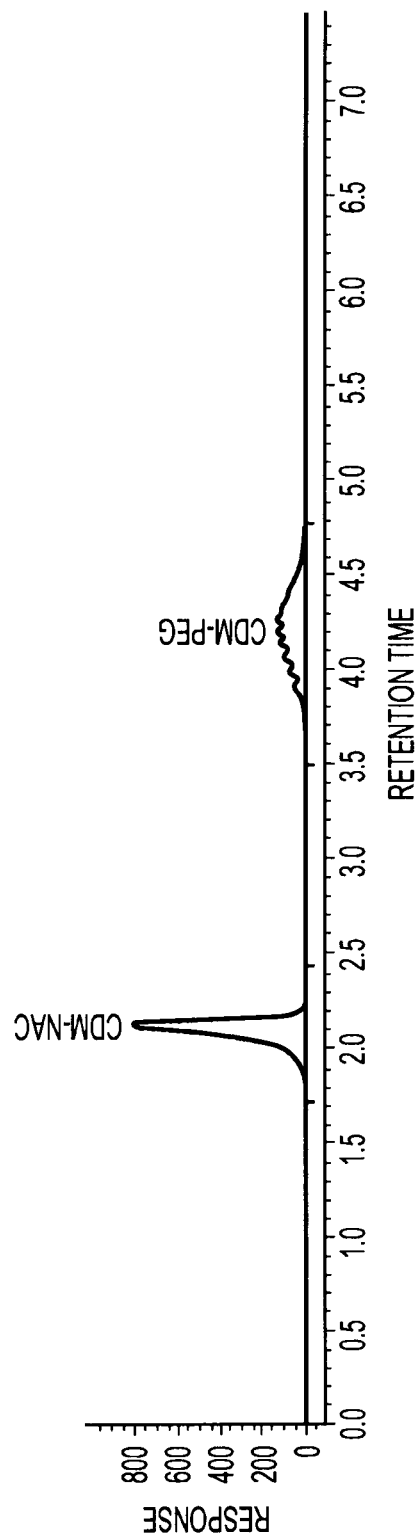
FIG. 10C An example of a chromatogram of CDM-GAL-NAC and CDM-PEG.

Example chromatogram of CDM-GALNAC and CDM-PEG is shown in FIG. 10C.

Figure 1B:
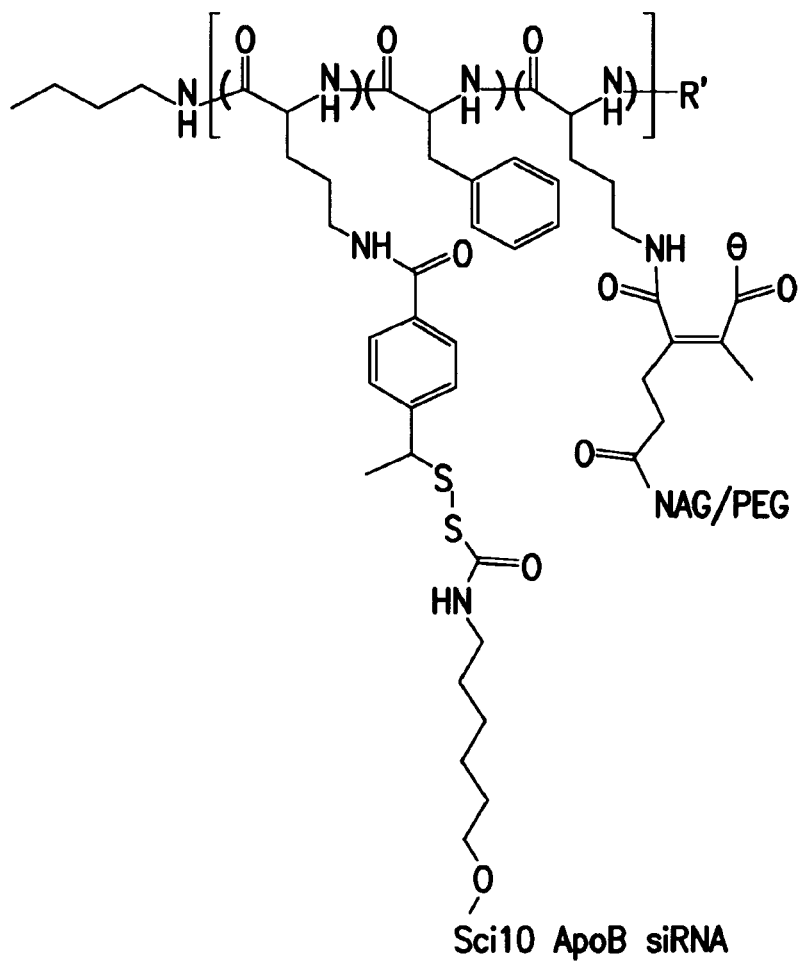
Figure 2B:
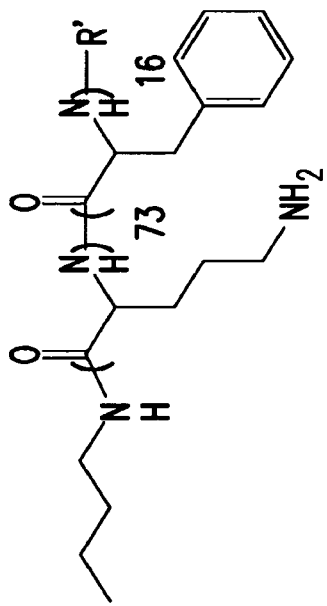
FIG. 2. RBC Hemolysis Data of Polymers 1 and 2.
Figure 2A:
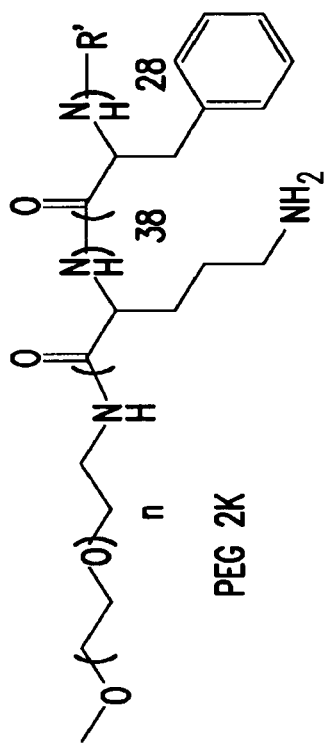
Figure 2C:
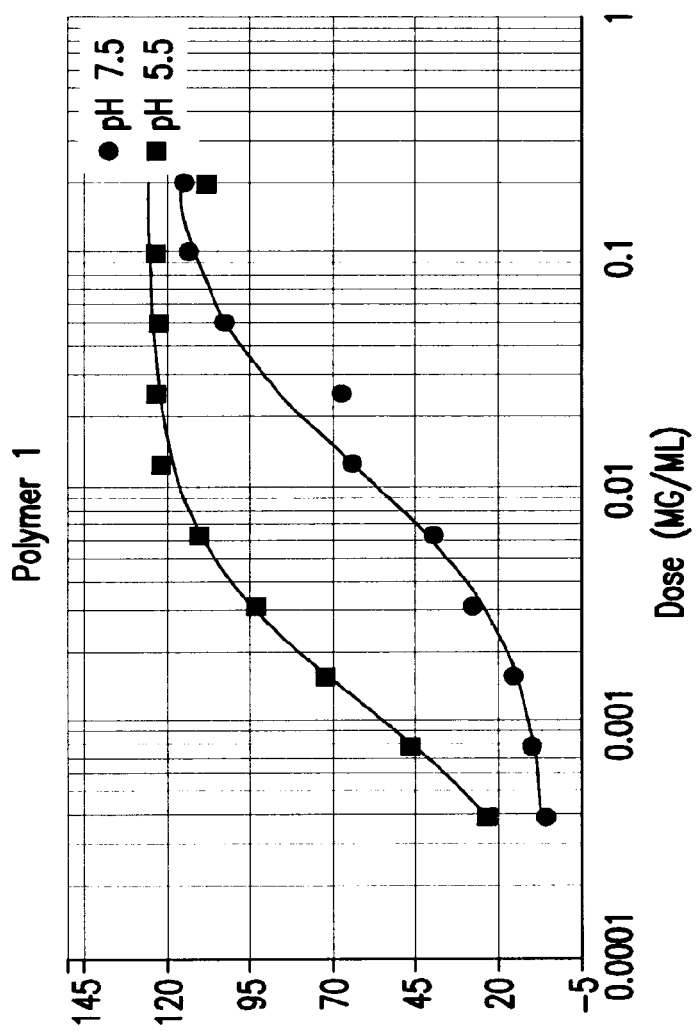
Figure 2D:
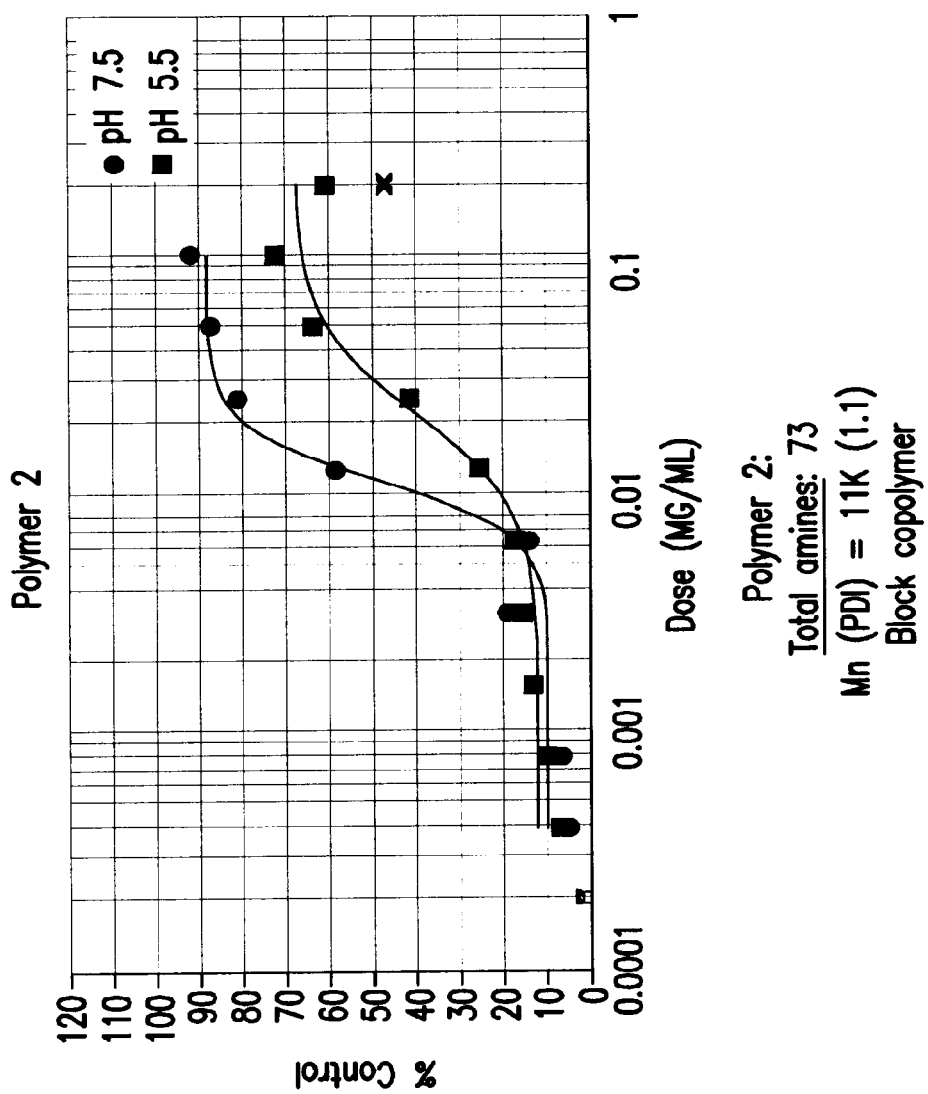

As shown in FIG. 1, the siRNA conjugation efficiencies are >85% for both polyconjugate 1 and 2, and the masking efficiencies are ~42% and 59% for polyconjugate 1 and polyconjugate 2, respectively.

Example 2

RBC Hemolysis Assay:

Human blood was collected in 10 ml EDTA Vacutainer tubes. A small aliquot was assessed for evidence of hemolysis by centrifugation at 15000 RCF for 2 min and non-hemolyzed samples were carried forward into the assay. Red blood cells (RBCs) were washed three times in either 150 mM NaCl /20 mM MES, pH 5.4, or 150 mM NaCl/20 mM HEPES, pH 7.5 by centrifuging at 1700×g for 3 min and resuspending in the same buffer to yield the initial volume. RBCs were then diluted in appropriate pH buffer to yield $10^8$ cells in suspension. A 10× stock concentration of the polymer was prepared and a 10 point, 2-fold dilution was performed in appropriate pH buffers. The diluted test agents were added to the RBCs in appropriate pH buffers in Costar 3368 flat-bottom 96 well plates. Solutions were mixed 6 to 8 times and the microtiter plate was covered with a low evaporation lid and incubated in a 37° C. warm room or incubator for 30 minutes to induce hemolysis. The plate was then centrifuged at 1700×g for 5 min and 150 µl supernatants were transferred to a Costar 3632 clear bottom 96 well plate. Hemoglobin absorbance was read at 541 nM using a Tecan Safire plate reader and percent hemolysis was calculated assuming 100% lysis to be measured by the hemoglobin released by RBCs in 1% Triton X-100.

As shown in FIG. 2, the data demonstrate that the polymers are lytic at endosomal pH 5.4.

Figure 3A:
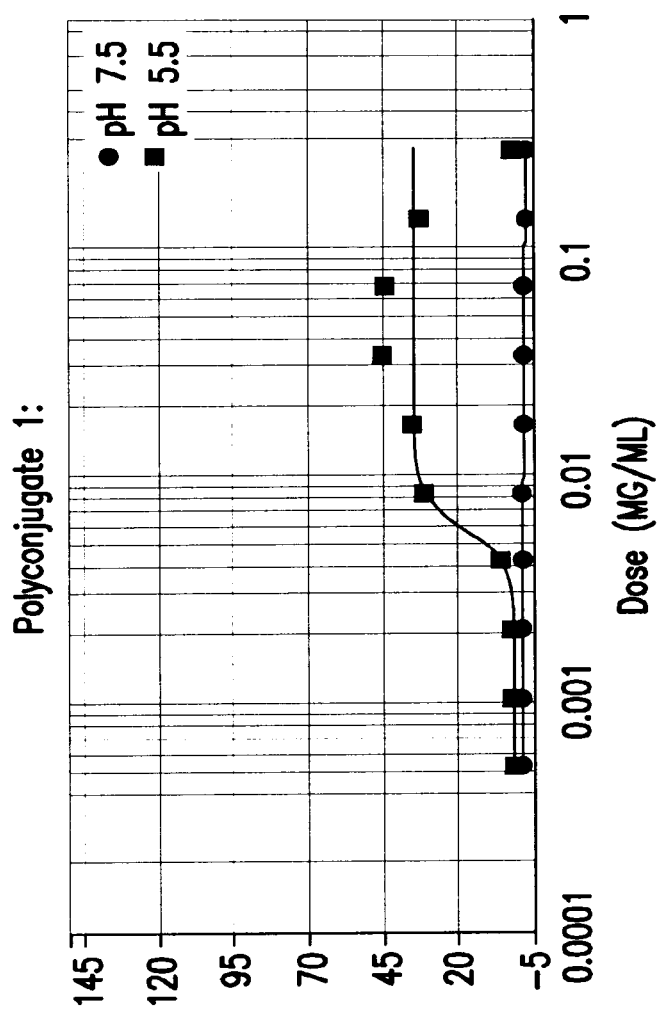
FIG. 3. RBC Hemolysis Data of Masked Polyconjugates from Polymers 1 and 2.
Figure 3B:
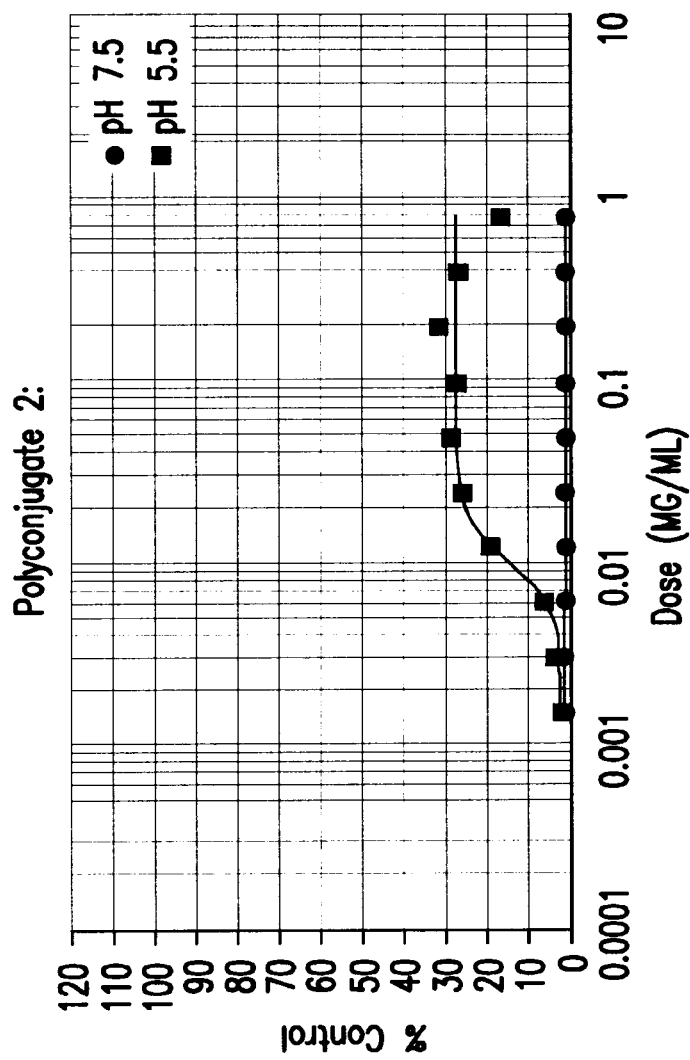

As shown in FIG. 3, the data demonstrates that in extracellular environment at pH 7.5, the polymers are masked with CDM and do not have any lytic activity. At endosomal pH 5.4, after the demasking of CDM, the polymers retain their lytic properties.

Example 3

HepG2 Gene Silencing and Toxicity Data:

HepG2 cells were plated in 96-well microtiter plates at 6000 cells/well and incubated overnight at 37 ° C. to allow cell adherence. 10×stock of PCs (polyconjugates) were prepared in media and 20 µl 10× PC was added to 180 µl media already in wells resulting in 1× final treatment and a 300-0 nM 10-point half log titration, based on siRNA concentration. Cells were incubated with PCs in 37 degrees $CO_2$ incubator for 24 -72h. MTS Toxicity Assay was performed on 24 h-72 h treated cells and cytotoxicity was assessed by CellTiter 96 Aqueous One Solution Cell Proliferation Assay (Promega #G3581, Madison, Wisc.). 40 µl MTS Solution was added, incubated in 37 degrees $CO_2$ incubator 1 hour, absorbance at 490 nm was read on Tecan Safire. Cells were then washed 3× in PBS and 150 µl/well bDNA DLM Lysis Buffer (Panomics "Quantigene" 1.0 bDNA kit #QG0002, Fremont, Calif.) was added. Plate was then incubated at 37 degrees in Warm Room 30 min. Lysates were removed and frozen at −70 degrees C. overnight. The next day, all cell lysates were thawed at RT and 20 µl of each lysate was removed and used for determination of total protein using Micro BCA Protein Assay kit (Pierce #23235, through Thermo Scientific, Rockford, Ill.). Absorbance was measured on Tecan Safire: Wavelength=562 nM, Plate=Costar96 ft, Number of Reads=100, Time between Reads=5. 50 µl each lysate was also used to determine mRNA expression levels in cells treated with SSB siRNA.

Apolipoprotein B (ApoB) mRNA knockdown was determined using Quantigene 1.0 bDNA Assay (Panomics # QG0002 Lot # 51CW36, Fremont, Calif.), a kit designed to quantitate RNA using a set of target-specific oligonucleotide probes.

Oligonucleotide synthesis is well known in the art. (See U.S. patent applications: U.S. 2006/0083780, U.S. 2006/0240554, U.S. 2008/0020058, U.S. 2009/0263407 and U.S. 2009/0285881 and PCT patent applications: WO 2009/086558, WO2009/127060, WO2009/132131, WO2010/042877, WO2010/054384, WO2010/054401, WO2010/054405 and WO2010/054406). The siRNAs disclosed and utilized in the Examples were synthesized via standard solid phase procedures.

Sci 10 ApoB siRNA was utilized in the experiments.

| Sci10 ApoB siRNA |
| --- |
| 5'-iB-CUUUAACAAUUCCUGAAAUTsT-iB-3' (SEQ ID NO.: 1) |
| 3'-UsUGAAAUUGUUAAGGACUsUsUsA-5' (SEQ ID NO.: 2) |

U - Ribose
iB - Inverted deoxy abasic
AGU - 2' Fluoro
T - 2' Deoxy
CU - 2' OCH₃
s - phophorothioate linkage Low Hex 9 siRNA was utilized in the experiments as a control siRNA.

| Low Hex 9 siRNA |
| --- |
| 5'-amil-iB-CUAGCUGGACACGUCGAUATsT-iB-3' (SEQ ID NO.: 3) |
| 3'-UsUGAUCGACCUGUGCAGCUAU-5' (SEQ ID NO.: 4) | amil - amino linker
iB - Inverted deoxy abasic
CU - 2'-Fluoro (F)
AGT - 2'-Deoxy
UGA - 2'-Methoxy (OMe)
AU - Ribose
s - phosphorothioate linkage Day 1

Make diluted lysis mixture (DLM) by mixing 1 volume of lysis mixture with 2 volumes of Nuclease Free water (Ambion cat # AM9930). Aspirate (PBS) from plate. Add 1500 DLM to each well and mix. (Include Column 1 as Buffer Alone Background). Incubate at 37° C. for 30 minutes. (After heating, Lysates can be placed in the −70° C. freezer until analysis is performed. If lysates are frozen, thaw at Room Temperature and incubate at 37° C. for 30 minutes and mix well before adding the samples to the capture plate.) Bring all reagents to Room Temperature before use, including the capture plates. Dilute CE, LE and BL probe set components: 0.10/well each into DLM. Add (100-X) µl diluted probe set/well. Add (X) µl cell lysate/well. Cover with foil plate sealer. Incubate at 53° C. for 16-20 hrs. Note: If assay contains multiple plates, perform steps 7, 8, 9 on 2-3 plates at a time and place at 53° C. before going on to next 2-3 plates.

Day 2

Bring Amplifier, Label Probe and Substrate to Room Temperature. Vortex and briefly centrifuge the tubes of Amplifier and Label Probe to bring the contents to the bottom of the tube. Prepare Wash buffer: add 3 ml Component 1 and 5 ml Component 2 to 1 L distilled water. (Wash Buffer is stable at Room Temperature for up to 6 months)

Prepare as needed: Amplifier Working solution, Label Probe Working Solution, and Substrate Working Solution:

Amplifier Working Solution—1:1000 dilution into Amplifier/Label Probe diluent.

Label Probe Working solution—1:1000 dilution into Amplifier/Label Probe diluent.

Substrate Working Solution—1:333 dilution of 10% Lithium Lauryl Sulfate Substrate into Substrate Solution (protect from light).

Add 2000 µl/well of wash buffer to overnight hybridization mixture. Repeat washes 3× with 300 µl of Wash Buffer. *Do not let the capture plates stand dry for longer than 5 minutes. Add 100 µl/well of Amplifier Working Solution. Seal plate with clear seal and incubate at 53° C. for 30 minutes. Wash plate 3× with 300 µl of Wash Buffer. Add 100 µl/well of Label Probe Working Solution. Seal plate with clear seal and incubate at 53° C. for 30 minutes. Wash plate 3× with 300 µl of Wash Buffer. Add 100 µl/well Substrate Working Solution. Seal plate with foil seal and incubate at 53° C. for 15 minutes. Let plate stand at Room Temperature for 10 minutes. Read in luminometer with integration time set to 0.2 seconds. bDNA data was normalized to protein and graphed using GraphPad Prism® Program using non-linear regression curve fit analysis.

As shown in FIG. 4, the data demonstrate the lack of in vitro toxicity for Polymer 1 and knockdown of ApoB mRNA in vitro for Polymer 2 with no measurable in vitro toxicites (via the MTS assay).

In Vivo Evaluation of Efficacy

CD1 mice were tail vein injected with the siRNA containing polymer conjugates at a dose of 3, and 6 mg/kg. In the case of rat studies, Sprague-Dawley rats were used. Rats were dosed at 0.25, 0.5, 1, 3, 6, 9, and 12 mg/kg.

Five days post dose, mice were sacrificed and liver tissue samples were immediately preserved in RNALater (Ambion). Preserved liver tissue was homogenized and total RNA isolated using a Qiagen bead mill and the Qiagen miRNA-Easy RNA isolation kit following the manufacturer's instructions. Liver ApoB mRNA levels were determined by quantitative RT-PCR. Message was amplified from purified RNA utilizing primers against the mouse ApoB mRNA (Applied Biosystems Cat. No. Mm01545156_ml). The PCR reaction was run on an ABI 7500 instrument with a 96-well Fast Block. The ApoB mRNA level is normalized to the housekeeping PPIB mRNA and GAPDH. PPIB and GAPDH mRNA levels were determined by RT-PCR using a commercial probe set (Applied Biosytems Cat. No. Mm00478295_ml and Mm4352339E_ml). Results are expressed as a ratio of ApoB mRNA/PPIB/GAPDH mRNA. All mRNA data is expressed relative to the vehicle control.

Alanine aminotransferanse (ALT) was measured using the ADVIA Chemistry Systems Alanine Aminotransferase (ALT) method, 03815151, Rev. A., according to the following reference, Clinical and Laboratory Standards Institute. *Laboratory Documents: Development and Control; Approved Guideline—Fifth Edition*: CLSI document GP2-A5 [ISBN 1-56238-600-X]. Clinical and Loboratory Standards Institute, 940 West Valley Road, Suite 1400, Wayne, Pa., 19807-1898 USA, 2006.

Figure 5A:
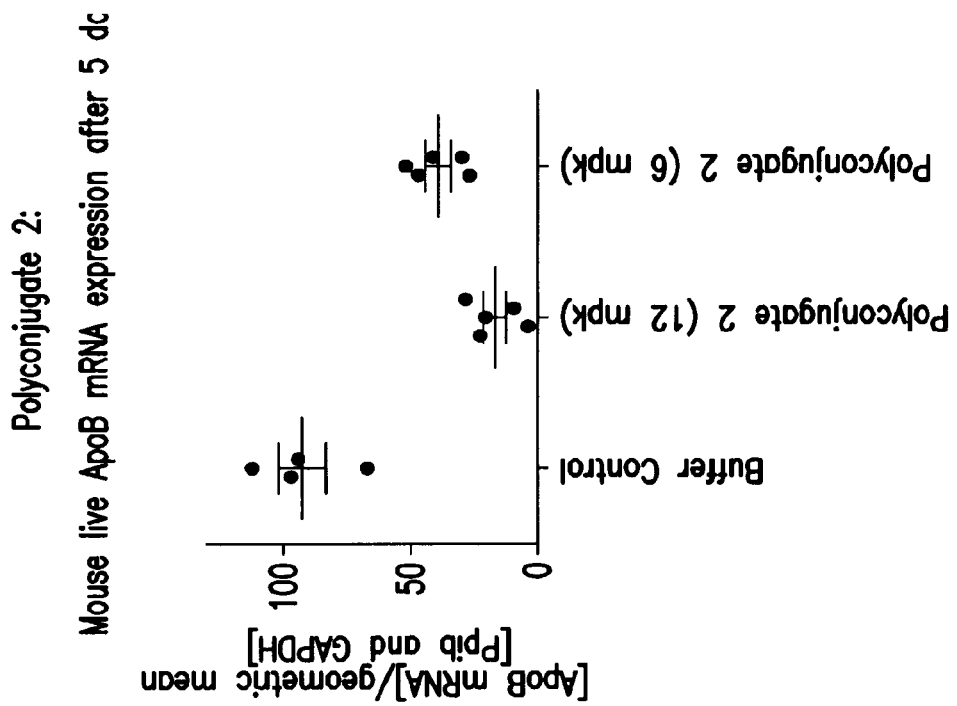
FIG. 5. Mouse In Vivo Data of Masked Polyconjugates from Polymers 1 and 2.
Figure 5B:
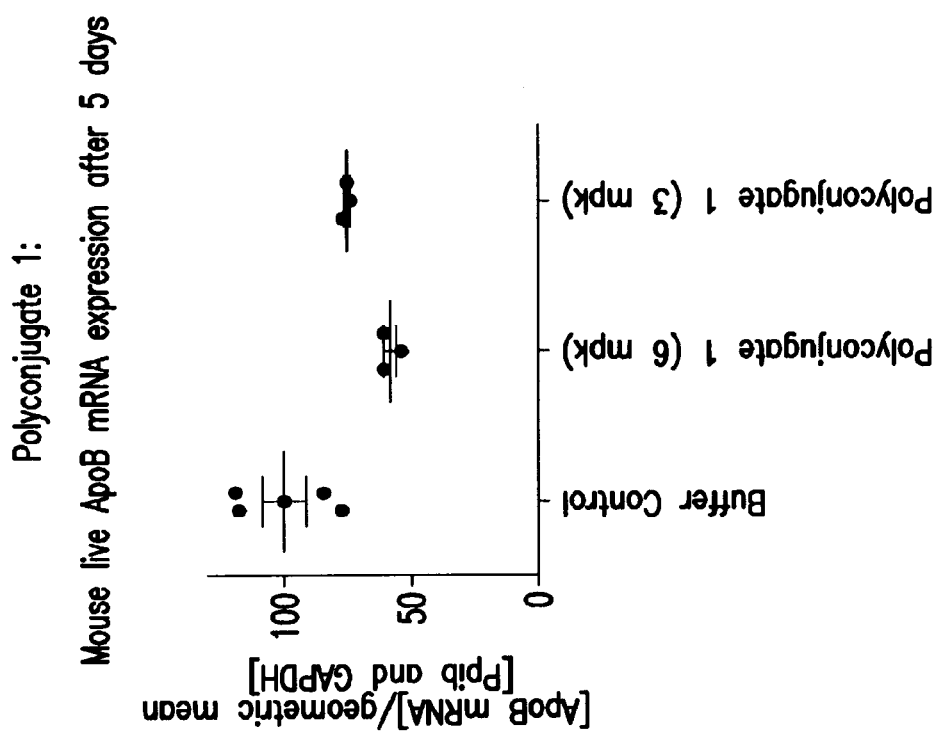
Figure 6B:
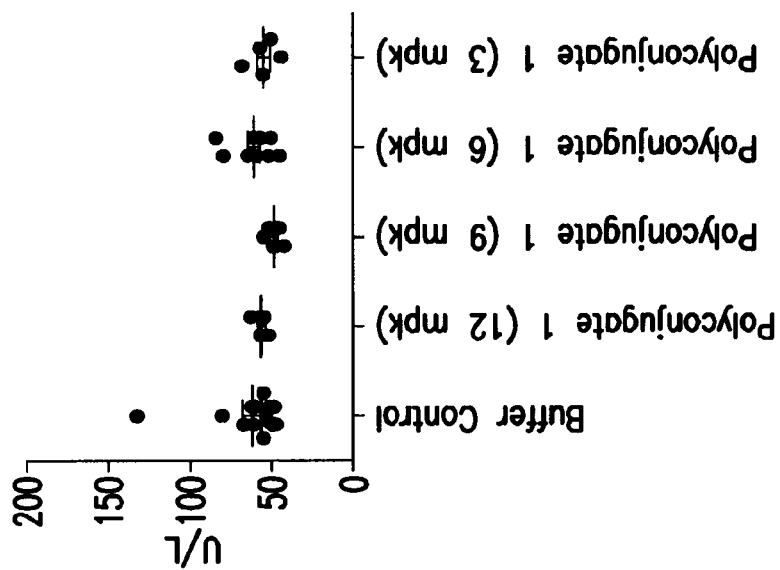
FIG. 6. Rat In Vivo Data of Masked Polyconjugates from Polymers 1 and 2.
Figure 6A:
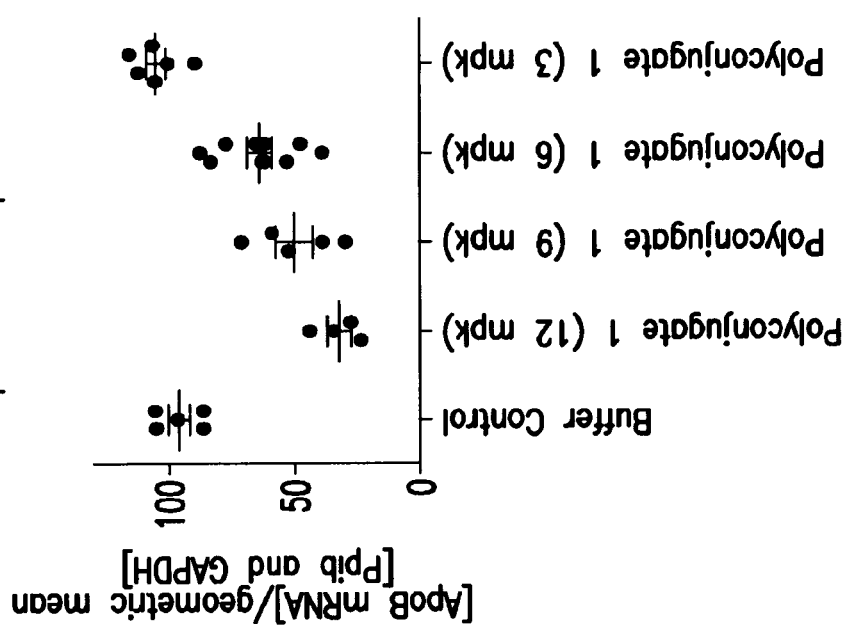
Figure 6D:
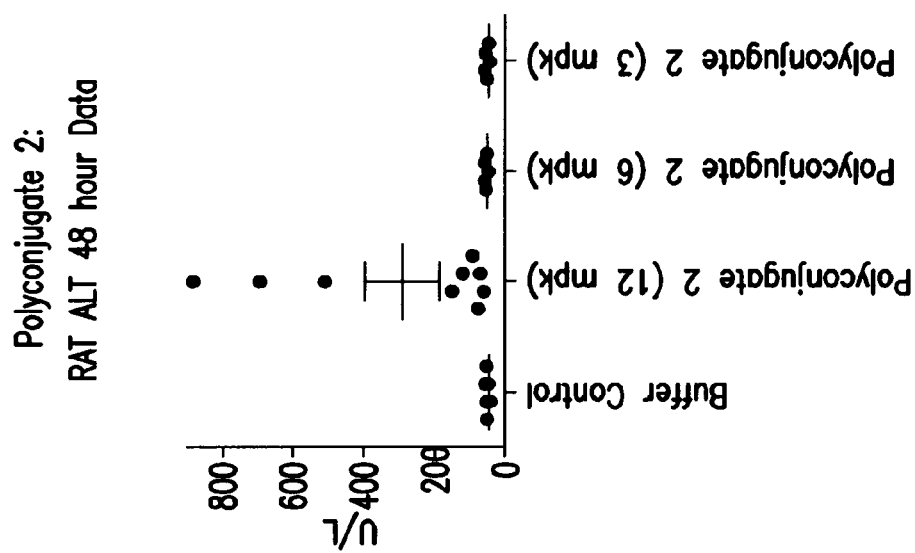
Figure 6C:
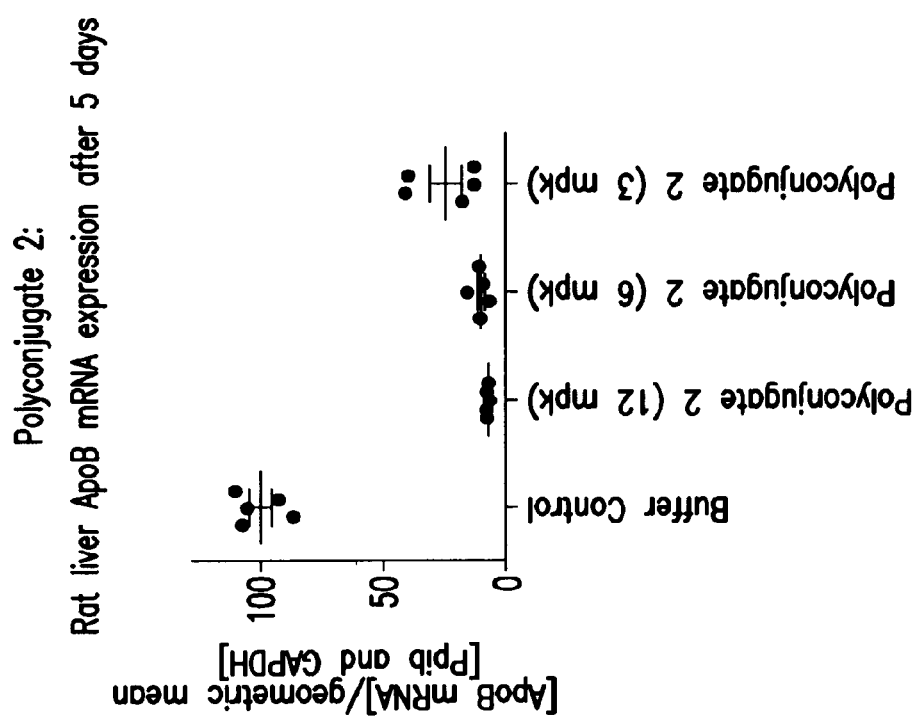

As shown in FIGS. 5 and 6, the data demonstrate that the polyconjugates of the instant invention can deliver siRNA in vivo to both mice and rat. Polymer 1 shows ~40% knockdown of ApoB with a 6 mg/kg dose in mice, and ~70% knockdown of ApoB at the 12 mpk dose in rats with no increase in liver or kidney toxicity markers. Polymer 2 shows ~60% knockdown of ApoB with a 6 mg/kg dose in mice, and ~90% knockdown of ApoB at a 6 mpk dose in rats with no increase in liver or kidney toxicity markers.

---

What is claimed is:

1. A polymer comprising Formula Z:

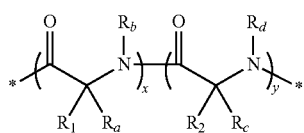

Z wherein:
x is 2 to 1000;
y is 2 to 1000;
$R_1$ is a cationic component;
$R_2$ is an aliphatic component selected from the group consisting of ethyl, propyl, hexyl, heptyl, octyl, nonyl, decyl, undecyl, dodecyl, tridecyl, tetradecyl, pentadecyl, hexadecyl, heptadecyl, octadecyl, cholesterol, lipid chains, benzyl, benzyl propanoate, benzyl acetate, isopropyl, 2-methylpropane, 2-methylbutane, isobutyl, 2-n-butyl, benzyl, 4-methyl phenol, ethylbenzene, 1-fluoro-4-methylbenzene, 4-methylbiphenyl, 2-methylnaphthalene, 1-methylnaphthalene, 5-ethyl-1-H-imidazole, 4-methyl imidazole, and 2-methyl indole;
$R_a$ is independently selected from $R_1$ and $R_2$;
$R_b$ is independently selected from $R_1$ and $R_2$;
$R_c$ is independently selected from $R_1$ and $R_2$; and
$R_d$ is independently selected from $R_1$ and $R_2$;
or stereoisomer thereof.

2. A polymer according to claim 1 comprising Formula Z':

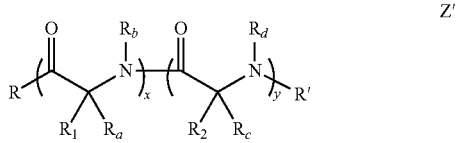

wherein:
x is 2 to 1000;
y is 2 to 1000;
R is an initiator;
R' is an end group;
$R_1$ is a cationic component;
$R_2$ is an aliphatic component selected from the group consisting of ethyl, propyl, hexyl, heptyl, octyl, nonyl, decyl, undecyl, dodecyl, tridecyl, tetradecyl, pentadecyl, hexadecyl, heptadecyl, octadecyl, cholesterol, lipid chains, benzyl, benzyl propanoate, benzyl acetate, isopropyl, 2-methylpropane, 2-methylbutane, isobutyl, 2-n-butyl, benzyl, 4-methyl phenol, ethylbenzene, 1-fluoro-4-methylbenzene, 4-methylbiphenyl, 2-methylnaphthalene, 1-methylnaphthalene, 5-ethyl-1-H-imidazole, 4-methyl imidazole, and 2-methyl indole;
$R_a$ is independently selected from $R_1$ and $R_2$;
$R_b$ is independently selected from $R_1$ and $R_2$;
$R_c$ is independently selected from $R_1$ and $R_2$; and
$R_d$ is independently selected from $R_1$ and $R_2$;
or stereoisomer thereof.

3. A polymer according to claim 2 comprising Formula Z":

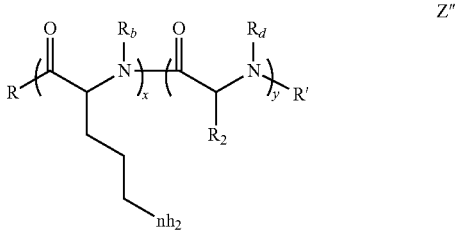

wherein:
x is 2 to 250;
y is 2 to 250;
R is an initiator;
R' is an end group; and
$R_2$ is an aliphatic component selected from the group consisting of ethyl, propyl, hexyl, heptyl, octyl, nonyl, decyl, undecyl, dodecyl, tridecyl, tetradecyl, pentadecyl, hexadecyl, heptadecyl, octadecyl, cholesterol, lipid chains, benzyl, benzyl propanoate, benzyl acetate, isopropyl, 2-methylpropane, 2-methylbutane, isobutyl, 2-n-butyl, benzyl, 4-methyl phenol, ethylbenzene, 1-fluoro-4-methylbenzene, 4-methylbiphenyl, 2-methylnaphthalene, 1-methylnaphthalene, 5-ethyl-1-H-imidazole, 4-methyl imidazole, and 2-methyl indole;
or stereoisomer thereof.

4. A polymer conjugate composition comprising the polymer of Formula Z of claim 1, a linker and an oligonucleotide.

5. The polymer conjugate composition of claim 4 further comprising a masking agent.

6. The polymer conjugate composion of claim 4 further comprising a targeting ligand.

7. A polymer conjugate composition of claim 4 further comprising a masking agent and a targeting ligand.

8. A polymer conjugate composition made by the 1) synthesis of an activated polymer comprising Formula Z of claim 1; 2) synthesis of an activated oligonucleotide; and 3) conjugation of the activated polymer with the activated oligonucleotide; optionally including the addition of a masking agent and/or a targeting ligand.

9. A polymer according to claim 1, wherein $R_1$ is independently an amine or a nitrogen heterocycle.

10. A polymer according to claim 1, wherein $R_1$ is selected from the group consisting of methyl amine, ethyl amine, propyl amine, butylamine, pentyl amine, hexyl amine, heptyl amine, octyl amine, nonyl amine, decyl amine, undecyl amine, dodecyl amine, tridecyl amine, tetradecyl amine, pentadecyl amine, hexadecyl amine, heptadecyl amine, octadecyl amine, 2-(2-aminoethoxy)ethyl, 2-(1H-imidazol-4-yl) ethyl, 2-[2-(2-aminoethoxy)ethoxy]ethyl, 3-amino-2-hydroxypropyl, 2-aminoethyl, 4-aminobutyl, 6-aminohexyl, 8-aminooctyl, 10-aminodecyl, and 1-methyl-2-imidazole modified ornithine.

11. A polymer according to claim 1, wherein $R_2$ is selected from the group consisting of isopropyl, benzyl, 4-methyl phenol, 4-methyl imidazole, and 2-methyl indole.

12. A polymer according to claim 2, wherein $R_1$ is an amine or a nitrogen heterocycle.

13. A polymer according to claim 2, wherein $R_1$ is selected from the group consisting of methyl amine, ethyl amine, propyl amine, butylamine, pentyl amine, hexyl amine, heptyl amine, octyl amine, nonyl amine, decyl amine, undecyl amine, dodecyl amine, tridecyl amine, tetradecyl amine, pentadecyl amine, hexadecyl amine, heptadecyl amine, octadecyl amine, 2-(2-aminoethoxy)ethyl, 2-(1H-imidazol-4-yl) ethyl, 2-[2-(2-aminoethoxy)ethoxy]ethyl, 3-amino-2-hydroxypropyl, 2-aminoethyl, 4-aminobutyl, 6-aminohexyl, 8-aminooctyl, 10-aminodecyl, and 1-methyl-2-imidazole modified ornithine.

14. A polymer according to claim 2, wherein $R_2$ is selected from the group consisting of isopropyl, benzyl, 4-methyl phenol, 4-methyl imidazole, and 2-methyl indole.

15. A polymer according to claim 2, wherein R is an amine, alcohol, water, alkali halide, alkoxide, hydroxide, or a transition metal initiator.

16. A polymer according to claim 2, wherein R' is hydrogen or carboxylate.

17. A polymer according to claim 3, wherein R is n-butylamine or mPEG-amine.

18. A polymer according to claim 3, wherein $R_2$ is selected from the group consisting of:

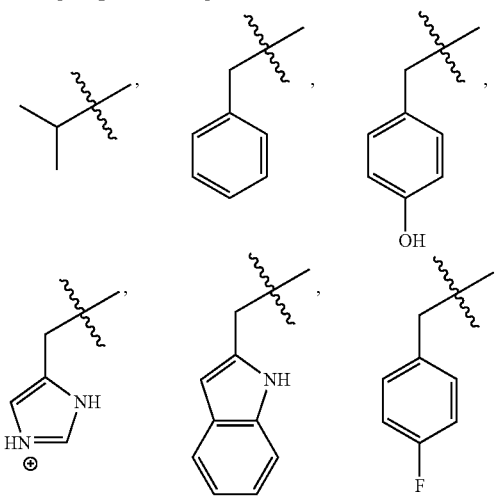

-continued
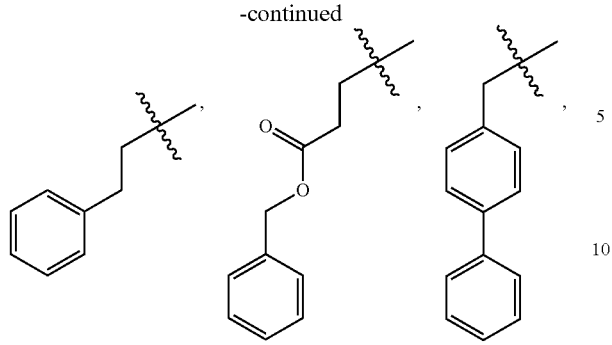
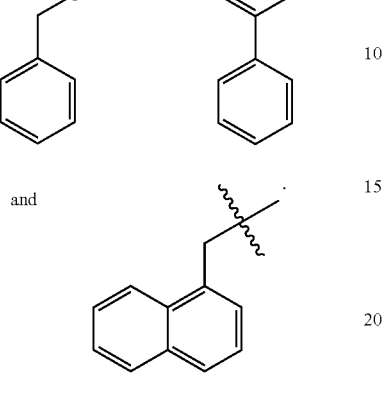
* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(4)
<223> OTHER INFORMATION: 2' O-methyl
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (5)..(6)
<223> OTHER INFORMATION: 2' fluoro
<220> FEATURE:
<221> NAME/KEY: misc_feature
<222> LOCATION: (7)..(7)
<223> OTHER INFORMATION: 2' O-methyl
<220> FEATURE:
```

-continued

```
<221> NAME/KEY: misc_feature
<222> LOCATION: (8)..(9)
<223> OTHER INFORMATION: 2' fluoro
<220> FEATURE:
<221> NAME/KEY: misc_feature
<222> LOCATION: (10)..(14)
<223> OTHER INFORMATION: 2' O-methyl
<220> FEATURE:
<221> NAME/KEY: misc_feature
<222> LOCATION: (15)..(18)
<223> OTHER INFORMATION: 2' fluoro
<220> FEATURE:
<221> NAME/KEY: misc_feature
<222> LOCATION: (19)..(19)
<223> OTHER INFORMATION: 2' O-methyl
<220> FEATURE:
<221> NAME/KEY: misc_feature
<222> LOCATION: (20)..(21)
<223> OTHER INFORMATION: 2' deoxy
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted deoxy abasic

<400> SEQUENCE: 1
cuuuaacaau uccugaaaut t                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: phosphorotioate linkage
<220> FEATURE:
<221> NAME/KEY: misc_feature
<222> LOCATION: (5)..(5)
<223> OTHER INFORMATION: 2' O-methyl
<220> FEATURE:
<221> NAME/KEY: misc_feature
<222> LOCATION: (6)..(10)
<223> OTHER INFORMATION: 2' fluoro
<220> FEATURE:
<221> NAME/KEY: misc_feature
<222> LOCATION: (11)..(12)
<223> OTHER INFORMATION: 2' O-methyl
<220> FEATURE:
<221> NAME/KEY: misc_feature
<222> LOCATION: (13)..(14)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(19)
<223> OTHER INFORMATION: 2' fluoro
<220> FEATURE:
<221> NAME/KEY: misc_feature
<222> LOCATION: (20)..(21)
<223> OTHER INFORMATION: 2' O-methyl
<220> FEATURE:
<221> NAME/KEY: misc_feature
<222> LOCATION: (20)..(21)
<223> OTHER INFORMATION: phosphorothioate linkage
```

<400> SEQUENCE: 2
auuucaggaa uuguuaaagu u                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: amino linker
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(2)
<223> OTHER INFORMATION: 2' fluoro
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (3)..(4)
<223> OTHER INFORMATION: 2' deoxy
<220> FEATURE:
<221> NAME/KEY: misc_feature
<222> LOCATION: (5)..(6)
<223> OTHER INFORMATION: 2' fluoro
<220> FEATURE:
<221> NAME/KEY: misc_feature
<222> LOCATION: (7)..(9)
<223> OTHER INFORMATION: 2' deoxy
<220> FEATURE:
<221> NAME/KEY: misc_feature
<222> LOCATION: (10)..(10)
<223> OTHER INFORMATION: 2' fluoro
<220> FEATURE:
<221> NAME/KEY: misc_feature
<222> LOCATION: (11)..(11)
<223> OTHER INFORMATION: 2' deoxy
<220> FEATURE:
<221> NAME/KEY: misc_feature
<222> LOCATION: (12)..(12)
<223> OTHER INFORMATION: 2' fluoro
<220> FEATURE:
<221> NAME/KEY: misc_feature
<222> LOCATION: (13)..(13)
<223> OTHER INFORMATION: 2' deoxy
<220> FEATURE:
<221> NAME/KEY: misc_feature
<222> LOCATION: (14)..(15)
<223> OTHER INFORMATION: 2' fluoro
<220> FEATURE:
<221> NAME/KEY: misc_feature
<222> LOCATION: (16)..(17)
<223> OTHER INFORMATION: 2' deoxy
<220> FEATURE:
<221> NAME/KEY: misc_feature
<222> LOCATION: (18)..(18)
<223> OTHER INFORMATION: 2' fluoro
<220> FEATURE:
<221> NAME/KEY: misc_feature
<222> LOCATION: (19)..(21)
<223> OTHER INFORMATION: 2' deoxy
<220> FEATURE:
<221> NAME/KEY: misc_feature
<222> LOCATION: (21)..(21)
<223> OTHER INFORMATION: inverted deoxy abasic

```
<400> SEQUENCE: 3
cuagcuggac acgucgauat t                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2' fluoro
<220> FEATURE:
<221> NAME/KEY: misc_feature
<222> LOCATION: (5)..(6)
<223> OTHER INFORMATION: 2' O-methyl
<220> FEATURE:
<221> NAME/KEY: misc_feature
<222> LOCATION: (7)..(7)
<223> OTHER INFORMATION: 2' fluoro
<220> FEATURE:
<221> NAME/KEY: misc_feature
<222> LOCATION: (8)..(8)
<223> OTHER INFORMATION: 2' O-methyl
<220> FEATURE:
<221> NAME/KEY: misc_feature
<222> LOCATION: (9)..(9)
<223> OTHER INFORMATION: 2' fluoro
<220> FEATURE:
<221> NAME/KEY: misc_feature
<222> LOCATION: (10)..(10)
<223> OTHER INFORMATION: 2' O-methyl
<220> FEATURE:
<221> NAME/KEY: misc_feature
<222> LOCATION: (11)..(13)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(17)
<223> OTHER INFORMATION: 2' fluoro
<220> FEATURE:
<221> NAME/KEY: misc_feature
<222> LOCATION: (18)..(21)
<223> OTHER INFORMATION: 2' O-methyl
<220> FEATURE:
<221> NAME/KEY: misc_feature
<222> LOCATION: (20)..(21)
<223> OTHER INFORMATION: phosphorothioate linkage

<400> SEQUENCE: 4
uaucgacgug uccagcuagu u                                              21
```